US009873895B2

(12) United States Patent
Marliere

(10) Patent No.: US 9,873,895 B2
(45) Date of Patent: Jan. 23, 2018

(54) PRODUCTION OF 1,3-DIENES BY ENZYMATIC CONVERSION OF 3-HYDROXYALK 4-ENOATES AND/OR 3-PHOSPHONOXYALK-4-ENOATES

(71) Applicant: Scientist of Fortune S.A., Luxembourg (LU)

(72) Inventor: Philippe Marliere, Mouscron (BE)

(73) Assignee: Scientist of Fortune S.A., Luxembourg (LU)

( * ) Notice: Subject to any disclaimer, the term of this patent is extended or adjusted under 35 U.S.C. 154(b) by 107 days.

(21) Appl. No.: 14/367,686

(22) PCT Filed: Dec. 18, 2012

(86) PCT No.: PCT/EP2012/075921
§ 371 (c)(1),
(2) Date: Jun. 20, 2014

(87) PCT Pub. No.: WO2013/092567
PCT Pub. Date: Jun. 27, 2013

(65) Prior Publication Data
US 2014/0370565 A1    Dec. 18, 2014

Related U.S. Application Data

(60) Provisional application No. 61/578,058, filed on Dec. 20, 2011.

(30) Foreign Application Priority Data

Dec. 20, 2011 (EP) ..................................... 11194704

(51) Int. Cl.
C12P 5/02 (2006.01)
C12N 9/02 (2006.01)
C12N 9/16 (2006.01)
C12N 9/12 (2006.01)
C12P 5/00 (2006.01)

(52) U.S. Cl.
CPC ............ *C12P 5/026* (2013.01); *C12N 9/1217* (2013.01); *C12P 5/007* (2013.01); *C12Y 207/01036* (2013.01); *C12Y 402/03027* (2013.01)

(58) Field of Classification Search
CPC ........ C12P 5/026; C12P 5/007; C12N 9/1217; C12Y 402/03027
USPC .................................................. 435/166, 146
See application file for complete search history.

(56) References Cited

U.S. PATENT DOCUMENTS 9,102,952 B2 * 8/2015 Marliere ................. C12P 5/007

FOREIGN PATENT DOCUMENTS

| WO | 2009076676 A2 | 6/2009 |
|---|---|---|
| WO | WO 2009/076676 | 6/2009 |
| WO | WO 2010/001078 | 1/2010 |
| WO | 2010001078 | 9/2010 |
| WO | 2010132845 A1 | 11/2010 |
| WO | WO 2011/076261 | 6/2011 |
| WO | 2011140171 A2 | 11/2011 |
| WO | WO 2011/140171 | 11/2011 |
| WO | 2012018624 A2 | 2/2012 |
| WO | WO 2012/052427 | 4/2012 |
| WO | WO 2013/082542 | 6/2013 |

OTHER PUBLICATIONS

Devos et al.,(Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Dewick et al. (The Royal Soc. Chem. 2002, 19, 181-222.*
International Search Report received in PCT/EP2012/075921, 2012.
Written Opinion received in PCT/EP2012/075921, 2012.
Kuzuyama, Tomohisa, "Mevalonate and Nonmevalonate Pathways for the Biosynthesis of Isoprene Units," Biosci. Biotechnol. Biochem. (2002) vol. 66, No. 8, pp. 1619-1627.
Sharkey, Thomas D. et al., "Evolution of the Isoprene Biosynthetic Pathway in Kudzu," Plant Physiology (2005) 137: 700-712.
Gogerty, David S. and Bobik, Thomas A., "Formation of Isobutene from 3-Hydroxy-3-Methylbutyrate by Diphosphomevalonate Decarboxylase," Applied and Environmental Microbiology (2010) vol. 76, No. 24, pp. 8004-8010.
Lindberg, Pia et al., "Engineering a Platform for Photosynthetic Isoprene Production in Cyanobacteria, Using Synechocystis as the Model Organism," Metabolic Engineering (2010) 12: 70-79.
Office Action dated Jan. 12, 2015 and received in U.S. Appl. No. 13/002,504.
Final Office Action dated Jun. 10, 2015 and received in U.S. Appl. No. 13/002,504.
Office Action dated Sep. 22, 2014 and received in U.S. Appl. No. 13/880,042.
Office Action dated Apr. 22, 2014 and received in U.S. Appl. No. 13/880,042.
Final Office Action dated Aug. 26, 2015 and received in U.S. Appl. No. 13/880,042.
Office Action dated Mar. 14, 2014 and received in U.S. Appl. No. 13/518,146.
Office Action dated Oct. 8, 2014 and received in U.S. Appl. No. 13/518,146.
Restriction Requirement dated Apr. 23, 2015 and received in U.S. Appl. No. 14/390,774.
Office Action dated Jul. 15, 2015 and received in U.S. Appl. No. 14/390,774.

(Continued)

*Primary Examiner* — Robert B Mondesi
*Assistant Examiner* — Mohammad Y Meah
(74) *Attorney, Agent, or Firm* — Michele M. Wales.; InHouse Patent Counsel, LLC

(57) ABSTRACT

The present invention relates to a method for generating 1,3-diene compounds through a biological process. More specifically, the invention relates to a method for producing 1,3-diene compounds (for example butadiene or isoprene) from molecules of the 3-hydroxyalk-4-enoate type or from 3-phosphonoxyalk-4-enoates.

24 Claims, 6 Drawing Sheets

(56) References Cited

OTHER PUBLICATIONS

Japanese Office Action English translation dated Dec. 2, 2016.
Lindberg et al., "Engineering a Platform for Photosynthetic Isoprene Production incyanobacteria,using Synechocystis as the Model Organism," Metabolic Engineering, 12 (2010) 70-79.
Patent & Utility Model Number Search dated Dec. 27, 2016 (translated document included).
Sharkey et al., "Evolution of the Isoprene Biosynthetic Pathway in Kudzu", Plant Physiology, Feb. 2005, vol. 137, pp. 700-712.

* cited by examiner

SEQUENCE LISTING

```
<160> NUMBER OF SEQ ID NOS: 30

<210> SEQ ID NO 1
<211> LENGTH: 400
<212> TYPE: PRT
<213> ORGANISM: Homo sapiens

<400> SEQUENCE: 1

Met Ala Ser Glu Lys Pro Leu Ala Ala Val Thr Cys Thr Ala Pro Val
1               5                   10                  15

Asn Ile Ala Val Ile Lys Tyr Trp Gly Lys Arg Asp Glu Glu Leu Val
            20                  25                  30
```

```
Leu Pro Ile Asn Ser Ser Leu Ser Val Thr Leu His Gln Asp Gln Leu
            35                  40                  45

Lys Thr Thr Thr Thr Ala Val Ile Ser Lys Asp Phe Thr Glu Asp Arg
 50                  55                  60

Ile Trp Leu Asn Gly Arg Glu Glu Asp Val Gly Gln Pro Arg Leu Gln
 65                  70                  75                  80

Ala Cys Leu Arg Glu Ile Arg Cys Leu Ala Arg Lys Arg Arg Asn Ser
                 85                  90                  95

Arg Asp Gly Asp Pro Leu Pro Ser Ser Leu Ser Cys Lys Val His Val
                100                 105                 110

Ala Ser Val Asn Asn Phe Pro Thr Ala Ala Gly Leu Ala Ser Ser Ala
            115                 120                 125

Ala Gly Tyr Ala Cys Leu Ala Tyr Thr Leu Ala Arg Val Tyr Gly Val
        130                 135                 140

Glu Ser Asp Leu Ser Glu Val Ala Arg Arg Gly Ser Gly Ser Ala Cys
145                 150                 155                 160

Arg Ser Leu Tyr Gly Gly Phe Val Glu Trp Gln Met Gly Glu Gln Ala
                165                 170                 175

Asp Gly Lys Asp Ser Ile Ala Arg Gln Val Ala Pro Glu Ser His Trp
            180                 185                 190

Pro Glu Leu Arg Val Leu Ile Leu Val Val Ser Ala Glu Lys Lys Leu
        195                 200                 205

Thr Gly Ser Thr Val Gly Met Arg Ala Ser Val Glu Thr Ser Pro Leu
210                 215                 220

Leu Arg Phe Arg Ala Glu Ser Val Val Pro Ala Arg Met Ala Glu Met
225                 230                 235                 240

Ala Arg Cys Ile Arg Glu Arg Asp Phe Pro Ser Phe Ala Gln Leu Thr
                245                 250                 255

Met Lys Asp Ser Asn Gln Phe His Ala Thr Cys Leu Asp Thr Phe Pro
            260                 265                 270

Pro Ile Ser Tyr Leu Asn Ala Ile Ser Trp Arg Ile Ile His Leu Val
        275                 280                 285

His Arg Phe Asn Ala His His Gly Asp Thr Lys Val Ala Tyr Thr Phe
            290                 295                 300

Asp Ala Gly Pro Asn Ala Val Ile Phe Thr Leu Asp Asp Thr Val Ala
305                 310                 315                 320

Glu Phe Val Ala Ala Val Trp His Gly Phe Pro Pro Gly Ser Asn Gly
                325                 330                 335

Asp Thr Phe Leu Lys Gly Leu Gln Val Arg Pro Ala Pro Leu Ser Ala
            340                 345                 350

Glu Leu Gln Ala Ala Leu Ala Met Glu Pro Thr Pro Gly Gly Val Lys
        355                 360                 365

Tyr Ile Ile Val Thr Gln Val Gly Pro Gly Pro Gln Ile Leu Asp Asp
        370                 375                 380

Pro Cys Ala His Leu Leu Gly Pro Asp Gly Leu Pro Lys Pro Ala Ala
385                 390                 395                 400

<210> SEQ ID NO 2
<211> LENGTH: 396
<212> TYPE: PRT
<213> ORGANISM: Saccharomyces cerevisiae

<400> SEQUENCE: 2

Met Thr Val Tyr Thr Ala Ser Val Thr Ala Pro Val Asn Ile Ala Thr
```

```
                1               5                        10                      15
            Leu Lys Tyr Trp Gly Lys Arg Asp Thr Lys Leu Asn Leu Pro Thr Asn
                               20                      25                      30
            Ser Ser Ile Ser Val Thr Leu Ser Gln Asp Asp Leu Arg Thr Leu Thr
                               35                      40                      45
            Ser Ala Thr Ala Pro Glu Phe Glu Arg Asp Thr Leu Trp Leu Asn
                               50                      55                      60
            Gly Glu Pro His Ser Ile Asp Asn Glu Arg Thr Gln Asn Cys Leu Arg
             65                      70                      75                      80
            Asp Leu Arg Gln Leu Arg Lys Glu Met Glu Ser Lys Asp Ala Ser Leu
                               85                      90                      95
            Pro Thr Leu Ser Gln Trp Lys Leu His Ile Val Ser Glu Asn Asn Phe
                              100                     105                     110
            Pro Thr Ala Ala Gly Leu Ala Ser Ser Ala Ala Gly Phe Ala Ala Leu
                              115                     120                     125
            Val Ser Ala Ile Ala Lys Leu Tyr Gln Leu Pro Gln Ser Thr Ser Glu
                              130                     135                     140
            Ile Ser Arg Ile Ala Arg Lys Gly Ser Gly Ser Ala Cys Arg Ser Leu
            145                     150                     155                     160
            Phe Gly Gly Tyr Val Ala Trp Glu Met Gly Lys Ala Glu Asp Gly His
                              165                     170                     175
            Asp Ser Met Ala Val Gln Ile Ala Asp Ser Ser Asp Trp Pro Gln Met
                              180                     185                     190
            Lys Ala Cys Val Leu Val Val Ser Asp Ile Lys Lys Asp Val Ser Ser
                              195                     200                     205
            Thr Gln Gly Met Gln Leu Thr Val Ala Thr Ser Glu Leu Phe Lys Glu
                              210                     215                     220
            Arg Ile Glu His Val Val Pro Lys Arg Phe Glu Val Met Arg Lys Ala
            225                     230                     235                     240
            Ile Val Glu Lys Asp Phe Ala Thr Phe Ala Lys Glu Thr Met Met Asp
                              245                     250                     255
            Ser Asn Ser Phe His Ala Thr Cys Leu Asp Ser Phe Pro Pro Ile Phe
                              260                     265                     270
            Tyr Met Asn Asp Thr Ser Lys Arg Ile Ile Ser Trp Cys His Thr Ile
                              275                     280                     285
            Asn Gln Phe Tyr Gly Glu Thr Ile Val Ala Tyr Thr Phe Asp Ala Gly
                              290                     295                     300
            Pro Asn Ala Val Leu Tyr Tyr Leu Ala Glu Asn Glu Ser Lys Leu Phe
            305                     310                     315                     320
            Ala Phe Ile Tyr Lys Leu Phe Gly Ser Val Pro Gly Trp Asp Lys Lys
                              325                     330                     335
            Phe Thr Thr Glu Gln Leu Glu Ala Phe Asn His Gln Phe Glu Ser Ser
                              340                     345                     350
            Asn Phe Thr Ala Arg Glu Leu Asp Leu Glu Leu Gln Lys Asp Val Ala
                              355                     360                     365
            Arg Val Ile Leu Thr Gln Val Gly Ser Gly Pro Gln Glu Thr Asn Glu
                              370                     375                     380
            Ser Leu Ile Asp Ala Lys Thr Gly Leu Pro Lys Glu
            385                     390                     395

<210> SEQ ID NO 3
<211> LENGTH: 404
<212> TYPE: PRT
<213> ORGANISM: Aspergillus niger
```

<400> SEQUENCE: 3

```
Met Ala Ala Ser Ala Asp Ser Gln Val Phe Arg Ala Thr Thr Thr Ala
1               5                   10                  15

Pro Val Asn Ile Ala Val Ile Lys Tyr Trp Gly Lys Arg Asp Ala Val
            20                  25                  30

Leu Asn Leu Pro Thr Asn Ser Ser Leu Ser Val Thr Leu Ser Gln Arg
        35                  40                  45

Ser Leu Arg Thr Leu Thr Thr Ala Ser Cys Ala Pro Phe Tyr Pro Ala
    50                  55                  60

Lys Asp Glu Leu Thr Leu Asn Gly Lys Pro Gln Asp Ile Gln Ser Ser
65                  70                  75                  80

Lys Arg Thr Leu Ala Cys Leu Ala Ser Leu Arg Ala His Arg Arg Glu
                85                  90                  95

Leu Glu Asp Ala Asn Pro Ser Leu Pro Lys Leu Ser Ser Phe Pro Leu
            100                 105                 110

Arg Ile Val Ser Glu Asn Asn Phe Pro Thr Ala Ala Gly Leu Ala Ser
        115                 120                 125

Ser Ala Ala Gly Phe Ala Ala Leu Val Arg Ala Val Ala Asp Leu Tyr
    130                 135                 140

Gln Leu Pro Gln Ser Pro Arg Asp Leu Ser Arg Ile Ala Arg Gln Gly
145                 150                 155                 160

Ser Gly Ser Ala Cys Arg Ser Leu Met Gly Gly Tyr Val Ala Trp Arg
                165                 170                 175

Ala Gly Ser Leu Glu Asp Gly Ser Asp Ser Leu Ala Glu Glu Val Ala
            180                 185                 190

Pro Gln Ser His Trp Pro Glu Met Arg Ala Leu Ile Leu Val Val Ser
        195                 200                 205

Ala Ala Lys Lys Asp Val Pro Ser Thr Glu Gly Met Gln Thr Thr Val
    210                 215                 220

Ala Thr Ser Asn Leu Phe Ala Thr Arg Ala Ser Thr Val Val Pro Glu
225                 230                 235                 240

Arg Met Ala Ala Ile Glu Thr Ala Ile Gln Asn Arg Asp Phe Pro Ala
                245                 250                 255

Phe Ala Glu Ile Thr Met Arg Asp Ser Asn Ser Phe His Ala Thr Cys
            260                 265                 270

Leu Asp Ser Trp Pro Pro Ile Phe Tyr Met Asn Asp Val Ser Arg Ala
        275                 280                 285

Ala Val Arg Leu Val His Asp Ile Asn Arg Ala Ile Gly Arg Thr Val
    290                 295                 300

Cys Ala Tyr Thr Tyr Asp Ala Gly Pro Asn Ala Val Ile Tyr Tyr Leu
305                 310                 315                 320

Glu Lys Asp Thr Glu Leu Val Ala Gly Thr Val Lys Ala Ile Leu Gly
                325                 330                 335

Glu Lys Thr Glu Gly Trp Glu Gly Pro Phe Tyr Thr Pro Leu Lys Asp
            340                 345                 350

Val Thr Thr Pro Gly Val Ser Leu Asp Glu Ile Asp Pro Arg Thr Val
        355                 360                 365

Glu Ser Leu Lys Asp Gly Val Ser Arg Val Ile Leu Thr Gly Val Gly
    370                 375                 380

Glu Gly Pro Ile Ser Val Asp Gln His Leu Val Ser Glu Lys Gly Asp
385                 390                 395                 400

Ile Leu Ser Ala
```

<210> SEQ ID NO 4
<211> LENGTH: 325
<212> TYPE: PRT
<213> ORGANISM: Lactobacillus plantarum

<400> SEQUENCE: 4

Met Lys Thr Val Thr Ala Lys Ala His Thr Asn Ile Ala Leu Val Lys
1               5                   10                  15

Tyr Trp Gly Lys Lys Asp Ala Ala Leu Met Leu Pro Gln Asn Gly Ser
            20                  25                  30

Ile Ser Leu Thr Leu Asp His Phe Tyr Thr Gln Thr Ser Val Thr Phe
        35                  40                  45

Asp Glu His Leu Asp Thr Asp Gln Ile Tyr Phe Asn His Gln His Leu
    50                  55                  60

Pro Thr Gly Lys Ser Ala Arg Ile Ser Gln Phe Leu Asp Leu Ile Arg
65                  70                  75                  80

Gln Arg Ser Gly Gln Thr Asn Tyr Ala Thr Val Lys Thr Glu Asn His
                85                  90                  95

Val Pro Thr Ser Ala Gly Leu Ala Ser Ser Ala Ser Gly Phe Ala Ala
            100                 105                 110

Leu Ala Gly Ala Ala Ser Arg Ala Ala Gly Leu Gln Leu Asp Ala Ala
        115                 120                 125

Asp Leu Ser Arg Leu Ala Arg Arg Gly Ser Gly Ser Ala Thr Arg Ser
    130                 135                 140

Ile Phe Gly Gly Phe Val Glu Trp His Ala Gly His Asp Asp Gln Ser
145                 150                 155                 160

Ser Tyr Ala Glu Val Leu Gln Asp Pro Val Asp Trp Asp Ile Gln Met
                165                 170                 175

Ile Ala Val Val Leu Lys Ala Thr Lys Lys Thr Ile Ser Ser Thr Asp
            180                 185                 190

Gly Met Ala Arg Val Val Ala Thr Ser Pro Tyr Tyr Pro Ala Trp Ile
        195                 200                 205

Thr Thr Ala Glu Thr Asp Leu Lys Arg Met Arg Gln Ala Ile Ala Asp
    210                 215                 220

Arg Asp Leu Thr Thr Val Gly Gln Ile Ala Glu Thr Asn Ala Met Arg
225                 230                 235                 240

Met His Ala Leu Asn Leu Ser Ala Glu Pro Ala Phe Asn Tyr Phe Thr
                245                 250                 255

Ala Asp Thr Leu Thr Ala Ile Gln Ala Val Asn Asp Leu Arg Ser His
            260                 265                 270

Gly Ile Asn Cys Tyr Tyr Thr Leu Asp Ala Gly Pro Asn Val Lys Ile
        275                 280                 285

Ile Cys Ala Gly Gln Asp Thr Asp Thr Ile Met Thr Gly Leu Gln Gln
    290                 295                 300

His Phe Asp Ala Asp Gln Leu Ile Val Ala Lys Pro Gly Pro Gly Ile
305                 310                 315                 320

Thr Ile Thr Glu Lys
                325

<210> SEQ ID NO 5
<211> LENGTH: 314
<212> TYPE: PRT
<213> ORGANISM: Streptococcus pyogenes

<400> SEQUENCE: 5

Met Asp Pro Asn Val Ile Thr Val Thr Ser Tyr Ala Asn Ile Ala Ile
1               5                   10                  15

Ile Lys Tyr Trp Gly Lys Glu Asn Gln Ala Lys Met Ile Pro Ser Thr
            20                  25                  30

Ser Ser Ile Ser Leu Thr Leu Glu Asn Met Phe Thr Thr Thr Ser Val
        35                  40                  45

Ser Phe Leu Pro Asp Thr Ala Thr Ser Asp Gln Phe Tyr Ile Asn Gly
    50                  55                  60

Ile Leu Gln Asn Asp Glu His Thr Lys Ile Ser Ala Ile Ile Asp
65              70                  75                  80

Gln Phe Arg Gln Pro Gly Gln Ala Phe Val Lys Met Glu Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asp Gln Leu Phe Asp Thr Gln Leu Asp Gln
        115                 120                 125

Lys Ala Leu Ala Gln Lys Ala Lys Phe Ala Ser Gly Ser Ser Ser Arg
130                 135                 140

Ser Phe Phe Gly Pro Val Ala Ala Trp Asp Lys Asp Ser Gly Ala Ile
145                 150                 155                 160

Tyr Lys Val Glu Thr Asp Leu Lys Met Ala Met Ile Met Leu Val Leu
                165                 170                 175

Asn Ala Ala Lys Lys Pro Ile Ser Ser Arg Glu Gly Met Lys Leu Cys
            180                 185                 190

Arg Asp Thr Ser Thr Thr Phe Asp Gln Trp Val Glu Gln Ser Ala Ile
        195                 200                 205

Asp Tyr Gln His Met Leu Thr Tyr Leu Lys Thr Asn Asn Phe Glu Lys
210                 215                 220

Val Gly Gln Leu Thr Glu Ala Asn Ala Leu Ala Met His Ala Thr Thr
225                 230                 235                 240

Lys Thr Ala Asn Pro Pro Phe Ser Tyr Leu Thr Lys Glu Ser Tyr Gln
                245                 250                 255

Ala Met Glu Ala Val Lys Glu Leu Arg Gln Glu Gly Phe Ala Cys Tyr
            260                 265                 270

Phe Thr Met Asp Ala Gly Pro Asn Val Lys Val Leu Cys Leu Glu Lys
        275                 280                 285

Asp Leu Ala Gln Leu Ala Glu Arg Leu Gly Lys Asn Tyr Arg Ile Ile
290                 295                 300

Val Ser Lys Thr Lys Asp Leu Pro Asp Val
305                 310

<210> SEQ ID NO 6
<211> LENGTH: 324
<212> TYPE: PRT
<213> ORGANISM: Picrophilus torridus
<220> FEATURE:
<221> NAME/KEY: misc_feature
<223> OTHER INFORMATION: DSM 9790

<400> SEQUENCE: 6

Met Glu Asn Tyr Asn Val Lys Thr Arg Ala Phe Pro Thr Ile Gly Ile
1               5                   10                  15

Ile Leu Leu Gly Gly Ile Ser Asp Lys Lys Asn Arg Ile Pro Leu His
            20                  25                  30

Thr Thr Ala Gly Ile Ala Tyr Thr Gly Ile Asn Asn Asp Val Tyr Thr

```
                  35                  40                  45
Glu Thr Lys Leu Tyr Val Ser Lys Asp Glu Lys Cys Tyr Ile Asp Gly
 50                  55                  60

Lys Glu Ile Asp Leu Asn Ser Asp Arg Ser Pro Ser Lys Val Ile Asp
 65                  70                  75                  80

Lys Phe Lys His Glu Ile Leu Met Arg Val Asn Leu Asp Asp Glu Asn
                 85                  90                  95

Asn Leu Ser Ile Asp Ser Arg Asn Phe Asn Ile Leu Ser Gly Ser Ser
                100                 105                 110

Asp Ser Gly Ala Ala Ala Leu Gly Glu Cys Ile Glu Ser Ile Phe Glu
                115                 120                 125

Tyr Asn Ile Asn Ile Phe Thr Phe Glu Asn Asp Leu Gln Arg Ile Ser
130                 135                 140

Glu Ser Val Gly Arg Ser Leu Tyr Gly Gly Leu Thr Val Asn Tyr Ala
145                 150                 155                 160

Asn Gly Arg Glu Ser Leu Thr Glu Pro Leu Leu Glu Pro Glu Ala Phe
                165                 170                 175

Asn Asn Phe Thr Ile Ile Gly Ala His Phe Asn Ile Asp Arg Lys Pro
                180                 185                 190

Ser Asn Glu Ile His Glu Asn Ile Ile Lys His Glu Asn Tyr Arg Glu
                195                 200                 205

Arg Ile Lys Ser Ala Glu Arg Lys Ala Lys Leu Glu Glu Leu Ser
                210                 215                 220

Arg Asn Ala Asn Ile Lys Gly Ile Phe Glu Leu Ala Glu Ser Asp Thr
225                 230                 235                 240

Val Glu Tyr His Lys Met Leu His Asp Val Gly Val Asp Ile Ile Asn
                245                 250                 255

Asp Arg Met Glu Asn Leu Ile Glu Arg Val Lys Glu Met Lys Asn Asn
                260                 265                 270

Phe Trp Asn Ser Tyr Ile Val Thr Gly Gly Pro Asn Val Phe Val Ile
                275                 280                 285

Thr Glu Lys Lys Asp Val Asp Lys Ala Met Glu Gly Leu Asn Asp Leu
                290                 295                 300

Cys Asp Asp Ile Arg Leu Leu Lys Val Ala Gly Lys Pro Gln Val Ile
305                 310                 315                 320

Ser Lys Asn Phe

<210> SEQ ID NO 7
<211> LENGTH: 319
<212> TYPE: PRT
<213> ORGANISM: Lactobacillus delbrueckii
<220> FEATURE:
<221> NAME/KEY: misc_feature
<223> OTHER INFORMATION: subsp. bulgaricus

<400> SEQUENCE: 7

Met Ser Lys Thr Ala Arg Ala His Thr Asn Ile Ala Leu Ile Lys Tyr
  1               5                  10                  15

Trp Gly Lys Lys Asp Ala Lys Leu Arg Leu Pro Leu Met Ser Ser Leu
                 20                  25                  30

Ser Met Thr Leu Asp Ala Phe Tyr Ser Asp Thr Lys Ile Ser Asp Ser
                 35                  40                  45

Glu Gln Met Ser Phe Lys Leu Asn Gly Gln Ala Val Ser Gly Pro Ala
 50                  55                  60

Ala Asp Arg Val Phe Ala Tyr Leu Arg Ala Met Gln Asp Arg Phe Gly
```

```
                65                  70                  75                  80
Val Lys Gly Asn Leu Ala Val Glu Ser Val Asn Gln Val Pro Thr Ala
                    85                  90                  95

Ala Gly Leu Ala Ser Ser Ser Ala Phe Ala Met Ala Ala Ala
                100                 105                 110

Phe Ala Asp His Tyr Gln Leu Gly Val Asp Arg Gln Glu Leu Ser Arg
                115                 120                 125

Met Ala Arg Met Gly Ser Gly Ser Ala Ser Arg Ser Val Phe Gly Gly
            130                 135                 140

Phe Ser Val Trp Gln Lys Gly Asp Ser Asp Gln Thr Ser Tyr Ala Tyr
145                 150                 155                 160

Pro Leu Asp Glu Glu Pro Asp Met Asp Leu Arg Leu Ala Val Glu
                165                 170                 175

Ile Asn Asp Gln Glu Lys Lys Ile Ser Ser Thr Lys Gly Met Glu Met
                180                 185                 190

Ser Lys Ser Ser Pro Phe Tyr Gln Val Trp Leu Asp Arg Asn Asp Ser
                195                 200                 205

Glu Ile Lys Glu Met Glu Ala Ile Lys Gln Ala Asp Phe Ser Lys
            210                 215                 220

Leu Gly Ser Leu Ala Glu Leu Asn Ala Ser Glu Met His Thr Leu Thr
225                 230                 235                 240

Phe Thr Ala Val Pro Gly Phe Thr Tyr Phe Glu Pro Asn Thr Ile Lys
                245                 250                 255

Ala Ile Lys Leu Val Gln Asp Leu Arg Gln Gln Gly Leu Glu Cys Tyr
                260                 265                 270

Tyr Thr Ile Asp Ala Gly Pro Asn Val Lys Val Leu Cys Gln Gly Lys
            275                 280                 285

Asn Ser Lys Asp Ile Ile Asn Cys Phe Glu Ser Phe Asp Arg Val
                290                 295                 300

Lys Ile Ile Glu Ala Gly Phe Gly Pro Gly Val Thr Leu Leu Asp
305                 310                 315

<210> SEQ ID NO 8
<211> LENGTH: 324
<212> TYPE: PRT
<213> ORGANISM: Haloquadratum walsbyi
<220> FEATURE:
<221> NAME/KEY: misc_feature
<223> OTHER INFORMATION: DSM 16790

<400> SEQUENCE: 8

Met Lys Ala Thr Ala Arg Ala His Pro Ile Gln Gly Leu Ile Lys Tyr
1               5                   10                  15

His Gly Met Arg Asp Ser Asp Lys Arg Tyr Pro Tyr His Asp Ser Ile
                20                  25                  30

Ser Val Cys Thr Ala Pro Ser Ala Thr Thr Thr Val Glu Phe Gln
                35                  40                  45

Ser Asp Ala Ser Gly Asp Val Tyr Ile Ile Asp Asn Glu Arg Val Asp
            50                  55                  60

Gly Arg Ala Ala Glu Arg Ile Asp Ala Val Val Glu His Val Arg Glu
65                  70                  75                  80

Arg Thr Gly Ile Arg Asp Pro Val Arg Leu Val Ser Thr Asn Ser Phe
                85                  90                  95

Pro Ser Asn Ile Gly Phe Gly Ser Ser Ser Gly Phe Ala Ala Ala
                100                 105                 110
```

```
Ala Met Ala Leu Val Thr Ala Ala Gly Glu Glu Leu Thr His Pro Glu
            115                 120                 125

Ile Ser Thr Ile Ala Arg Arg Gly Ser Ser Ala Ala Arg Ala Val
130                 135                 140

Thr Gly Ala Phe Ser Gln Leu Tyr Ser Gly Met Asn Asp Thr Asp Cys
145                 150                 155                 160

His Ala Glu Arg Ile Glu Thr Asp Leu Asp Ala Thr Val Arg Thr Val
                165                 170                 175

Ala Ala His Val Pro Ala Tyr Lys Glu Thr Glu Ala His Arg Glu
            180                 185                 190

Ala Ala Gln Ser His Met Phe Asp Ala Arg Leu Ala His Val His His
            195                 200                 205

Gln Ile Asp Ala Met Arg Asp Ala Leu Tyr Asn Ala Asp Phe Asp Arg
210                 215                 220

Ile Phe Glu Leu Ala Glu His Asp Ser Leu Ser Leu Thr Ala Ala Thr
225                 230                 235                 240

Met Thr Gly Pro Ala Gly Trp Val Tyr Trp Gln Pro Gln Thr Ile Ala
                245                 250                 255

Val Phe Asn Thr Val Arg Glu Leu Arg Glu Arg Glu Ser Ile Pro Val
            260                 265                 270

Tyr Phe Ser Thr Asp Thr Gly Ala Ser Val Tyr Val Asn Thr Thr Ala
        275                 280                 285

Ala His Val Asp Thr Val Glu Ser Ala Ile Ser Asp Ile Gly Ile Asp
    290                 295                 300

Thr Asp Ile Trp Thr Val Gly Gly Pro Ala Thr Val Leu Ser Ala Ser
305                 310                 315                 320

Asp Ser Leu Phe

<210> SEQ ID NO 9
<211> LENGTH: 322
<212> TYPE: PRT
<213> ORGANISM: Lactobacillus salivarius
<220> FEATURE:
<221> NAME/KEY: misc_feature
<223> OTHER INFORMATION: subsp. salivarius (strain UCC118)

<400> SEQUENCE: 9

Met Ser Asn His Ala Ala Arg Ala His Thr Asn Ile Ala Leu Ile
1               5                   10                  15

Lys Tyr Trp Gly Lys Lys Asp Thr Glu Leu Ile Leu Pro Met Asn Asn
                20                  25                  30

Ser Leu Ser Leu Thr Leu Asp His Phe Tyr Thr Asp Thr Ser Val Thr
            35                  40                  45

Phe Asp Ser Ser Tyr Thr Lys Asp Thr Phe Ile Leu Asn Gly Lys Glu
        50                  55                  60

Ile Pro Asn Glu Asn Val His Lys Phe Leu Asn Ile Val Arg Glu Lys
65                  70                  75                  80

Ala Gly Ile Ser Glu Phe Ala Lys Val Asn Ser Thr Asn His Val Pro
                85                  90                  95

Thr Thr Ala Gly Leu Ala Ser Ser Ala Ser Ala Phe Ala Ala Leu Ala
            100                 105                 110

Ala Ala Ala Ser Lys Ala Ser Gly Met Asn Leu Ser Arg Arg Asp Leu
        115                 120                 125

Ser Arg Leu Ala Arg Arg Gly Ser Gly Ser Ala Thr Arg Ser Ile Tyr
    130                 135                 140
```

```
Gly Gly Phe Val Glu Trp Gln Ala Gly Asp Asn Asp Leu Asn Ser Tyr
145                 150                 155                 160

Ala Val Pro Phe Ile Glu Asn Val Ser Trp Asp Ile Lys Met Ile Ala
                165                 170                 175

Val Val Ile Asn Ser Lys Pro Lys Ile Thr Ser Arg Ala Gly Met
            180                 185                 190

Gln Thr Val Val Asn Thr Ser Pro Tyr Tyr Asn Ser Trp Ile Lys Glu
        195                 200                 205

Ala Asn Arg Ser Ile Pro Leu Met Lys Glu Ala Ile Ser Lys Gln Asp
    210                 215                 220

Phe Thr Thr Met Gly Glu Leu Ala Glu Asn Ala Met Lys Met His
225                 230                 235                 240

Ala Leu Asn Leu Ser Ala His Pro His Phe Ser Tyr Phe Ser Pro Glu
                245                 250                 255

Ser Ile Gln Val Met Asn Leu Val Glu Glu Leu Arg Ser Met Gly Ile
                260                 265                 270

Glu Cys Tyr Tyr Thr Met Asp Ala Gly Pro Asn Val Lys Ile Ile Cys
                275                 280                 285

Leu Gly Lys Asp Thr Ala Ser Ile Thr Ser Phe Leu Gln Lys Asn Leu
    290                 295                 300

Pro Asn Thr Glu Val Leu Val Ser Ser Ala Gly Pro Gly Val Gln Tyr
305                 310                 315                 320

Leu Asp

<210> SEQ ID NO 10
<211> LENGTH: 314
<212> TYPE: PRT
<213> ORGANISM: Oenococcus oeni
<220> FEATURE:
<221> NAME/KEY: misc_feature
<223> OTHER INFORMATION: Strain BAA-331 / PSU-1

<400> SEQUENCE: 10

Met Ala Lys Val Arg Ala Tyr Thr Asn Ile Ala Leu Ile Lys Tyr Trp
1               5                   10                  15

Gly Lys Ser Asp Leu Asn Trp Asn Leu Pro Thr Ser Ser Ile Gly
            20                  25                  30

Leu Thr Leu Asp Arg Phe Tyr Thr Asp Thr Ser Val Glu Ile Asp Gln
        35                  40                  45

Phe Ser Lys Lys Asp Phe Phe Gln Leu Asn Gly Gln Gln Ile Glu Gly
    50                  55                  60

Pro Lys Ile Ser Lys Ile Ile Asn Phe Ile Arg Asn Ser Cys Gly Asn
65                  70                  75                  80

Lys Asn Phe Val Lys Val Ile Ser Glu Asn His Val Pro Thr Ser Ala
                85                  90                  95

Gly Leu Ala Ser Ser Ala Ser Ala Phe Ala Ala Leu Thr Lys Ala Ala
                100                 105                 110

Asn Gln Ala Phe Gly Leu Glu Leu Asp Asn Arg Glu Leu Ser Lys Ile
            115                 120                 125

Ala Arg Ile Gly Ser Gly Ser Ala Ser Arg Ser Ile Phe Gly Gly Phe
    130                 135                 140

Ser Ile Trp His Lys Gly Gln Asn Lys Asp Asp Ser Phe Ala Glu Ser
145                 150                 155                 160

Ile Leu Asp Pro Val Asp Phe Asp Ile Arg Val Ile Asp Ile Leu Ala
                165                 170                 175
```

```
Asp Lys Arg Val Lys Lys Ile Ser Ser Ser Gln Gly Met Gln Leu Ala
            180                 185                 190

Gln Thr Ser Pro Asn Tyr Asp Ser Trp Leu Lys Lys Asn Asp Arg Gln
        195                 200                 205

Ile Asp Glu Met Leu Lys Ala Ile Ser Asp His Asp Leu Glu Lys Ile
    210                 215                 220

Gly Leu Ile Ala Glu Thr Asn Ser Ala Ser Met His Glu Leu Asn Arg
225                 230                 235                 240

Thr Ala Lys Val Pro Phe Asp Tyr Phe Thr Glu Asn Thr Arg Glu Ile
                245                 250                 255

Ile Ala Glu Val Asp Gln Leu Tyr Lys Lys Gly Ile Leu Ala Phe Ala
            260                 265                 270

Thr Val Asp Ala Gly Pro Asn Val Lys Val Ile Thr Asn Ser Glu Tyr
        275                 280                 285

Gln Glu Lys Ile Ile Asn Val Leu Lys Glu Tyr Gly Glu Ile Leu Val
    290                 295                 300

Gln Lys Pro Gly Arg Gly Val Ala Asn Val
305                 310
```

<210> SEQ ID NO 11
<211> LENGTH: 327
<212> TYPE: PRT
<213> ORGANISM: Pediococcus pentosaceus
<220> FEATURE:
<221> NAME/KEY: misc_feature
<223> OTHER INFORMATION: ATCC 25745

<400> SEQUENCE: 11

```
Met Asn Glu Lys His Gly Phe Ala Arg Ala His Thr Asn Ile Ala Leu
1               5                   10                  15

Leu Lys Tyr Trp Gly Lys Ile Asn Ser Asp Leu Ile Leu Pro Ala Asn
            20                  25                  30

Asp Ser Ile Ser Leu Thr Leu Asp Lys Phe Tyr Thr Asp Thr Glu Val
        35                  40                  45

Thr Phe Ser Asp Glu Tyr Thr Ser Asn Leu Phe Tyr Leu Asn His Gln
    50                  55                  60

Leu Ile Asp Val Lys Lys Met Gln Arg Ile Asn Arg Val Leu Glu Ala
65                  70                  75                  80

Val Lys Ser Glu Phe Gly Tyr Gln Gly Phe Ala Lys Ile Glu Ser Glu
                85                  90                  95

Asn His Val Pro Thr Ala Ala Gly Leu Ala Ser Ser Ala Ser Gly Met
            100                 105                 110

Ala Ala Leu Ala Gly Ala Ala Val Ser Ala Leu Gly Ser His Thr Asp
        115                 120                 125

Leu Thr Asn Leu Ser Arg Leu Ala Arg Leu Gly Ser Gly Ser Ala Ser
    130                 135                 140

Arg Ser Val Phe Gly Gly Ile Val His Trp His Arg Gly Tyr Asp His
145                 150                 155                 160

Gln Ser Ser Phe Ala Glu Gln Ile Val Ser Glu Asp Gln Ile Asp Leu
                165                 170                 175

Asn Met Val Thr Ile Val Ile Asp Arg Arg Gln Lys Lys Val Lys Ser
            180                 185                 190

Thr Leu Gly Met Gln His Thr Ala Ser Thr Ser Pro Phe Tyr Pro Ala
        195                 200                 205

Trp Val Glu Ala Thr Asn Gln Ala Ile Pro Glu Met Ile Ser Ala Val
    210                 215                 220
```

```
Gln Asn Asn Asp Phe Thr Lys Ile Gly Glu Leu Ala Glu His Ser Ala
225                 230                 235                 240

Ala Met Met His Ala Thr Thr Leu Ser Ser Lys Pro Ala Phe Thr Tyr
                245                 250                 255

Phe Ala Pro Glu Thr Ile Gln Ala Ile Lys Leu Val Glu Gln Leu Arg
            260                 265                 270

Glu Ser Gly Ile Glu Cys Tyr Tyr Thr Ile Asp Ala Gly Pro Asn Val
        275                 280                 285

Lys Val Leu Cys Gln Ser Lys Asn Ile Thr Arg Val Lys Arg Phe Phe
    290                 295                 300

Ala Ser Tyr Phe Asp Gln Asp Gln Leu Val Val Ala Lys Pro Gly Ser
305                 310                 315                 320

Gly Ile Lys Phe Thr Lys Asn
                325

<210> SEQ ID NO 12
<211> LENGTH: 315
<212> TYPE: PRT
<213> ORGANISM: Streptococcus gordonii

<400> SEQUENCE: 12

Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
                20                  25                  30

Ser Ser Ile Ser Leu Thr Leu Glu Asn Met Tyr Thr Gly Thr Gln Leu
            35                  40                  45

Ser Pro Leu Pro Asp Thr Ala Thr Gly Asp Glu Phe Tyr Ile Asp Gly
        50                  55                  60

Gln Leu Gln Ser Pro Ala Glu His Ala Lys Ile Ser Lys Ile Ile Asp
65                  70                  75                  80

Arg Phe Arg Ser Pro Glu Asp Gly Phe Val Arg Val Asp Thr Ser Asn
                85                  90                  95

Asn Met Pro Thr Ala Ala Gly Leu Ser Ser Ser Ser Ser Gly Leu Ser
            100                 105                 110

Ala Leu Val Lys Ala Cys Asn Ala Tyr Phe Gln Thr Gly Tyr Gln Thr
        115                 120                 125

Glu Glu Leu Ala Gln Leu Ala Lys Phe Ala Ser Gly Ser Ser Ala Arg
    130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Ala Gln Ser Ala Leu
        195                 200                 205

Asp Tyr Gln Ala Met Leu Gly Tyr Leu Gln Asp Asn Asp Phe Ala Lys
    210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255

Ala Met Asp Ala Val Arg Lys Leu Arg Glu Gln Gly Glu Arg Cys Tyr
```

```
                260                 265                 270
Phe Thr Met Asp Ala Gly Pro Asn Val Lys Val Leu Cys Leu Glu Glu
        275                 280                 285

Asp Leu Asp His Leu Ala Ala Ile Phe Glu Lys Asp Tyr Arg Leu Ile
        290                 295                 300

Val Ser Lys Thr Lys Asp Leu Ser Asp Glu Ser
305                 310                 315

<210> SEQ ID NO 13
<211> LENGTH: 328
<212> TYPE: PRT
<213> ORGANISM: Dichelobacter nodosus
<220> FEATURE:
<221> NAME/KEY: misc_feature
<223> OTHER INFORMATION: VCS1703A

<400> SEQUENCE: 13

Met His Ser Ala Thr Ala Phe Ala Pro Ala Asn Ile Ala Leu Ala Lys
1               5                   10                  15

Tyr Trp Gly Lys Arg Asp Ala Gln Leu Asn Leu Pro Thr Asn Gly Ser
            20                  25                  30

Leu Ser Ile Ser Leu Ala His Leu Gly Thr Thr Thr Thr Ile Ser Ala
        35                  40                  45

Gly Glu Arg Asp Gln Leu Tyr Cys Asp His Arg Leu Leu Pro Pro Asp
    50                  55                  60

Thr Ala Phe Val Gln Lys Val Trp His Phe Ile Asp Phe Cys Gln Pro
65                  70                  75                  80

Lys Arg Pro Pro Leu Val Ile His Thr Gln Asn Asn Ile Pro Thr Ala
                85                  90                  95

Ala Gly Leu Ala Ser Ser Ala Ser Gly Phe Ala Ala Leu Thr Leu Ala
            100                 105                 110

Leu Asn Asp Phe Phe Gln Trp Ser Leu Ser Arg Glu Gln Leu Ser Gln
        115                 120                 125

Ile Ala Arg Arg Gly Ser Gly Ser Ala Cys Arg Ser Leu Trp Gln Gly
    130                 135                 140

Phe Val Tyr Trp Gln Lys Gly Glu Lys Ala Asp Gly Ser Asp Cys Tyr
145                 150                 155                 160

Ala Arg Pro Ile Ala Ser Asp Trp Gln Asp Leu Arg Leu Gly Ile Ile
                165                 170                 175

Thr Ile Asp Ala Ala Ala Lys Lys Ile Ser Ser Arg Gln Ala Met Asn
            180                 185                 190

His Thr Ala Ala Ser Ser Pro Leu Phe Ser Ser Trp Thr Gln Ala Ala
        195                 200                 205

Glu Ala Asp Leu Lys Val Ile Tyr Gln Ala Val Leu Asp Arg Asp Phe
    210                 215                 220

Leu Thr Leu Ala Gln Thr Ala Glu Ala Asn Ala Leu Met Met His Ala
225                 230                 235                 240

Ser Leu Leu Ala Ala Arg Pro Ala Ile Phe Tyr Trp Gln Pro Gln Thr
                245                 250                 255

Leu Ala Met Leu Gln Cys Ile Trp Gln Ala Arg Ala Glu Gly Leu Ala
            260                 265                 270

Val Tyr Ala Thr Leu Asp Ala Gly Ala Asn Val Lys Leu Leu Tyr Arg
        275                 280                 285

Ala Gln Asp Glu Ala Glu Ile Ala Ser Met Phe Pro Gln Ala Gln Leu
    290                 295                 300
```

Ile Asn Pro Phe Gln Thr Val Thr Ser Ser Ala Arg His Thr Gly Glu
305                 310                 315                 320

Asp Ala Gln Lys Pro Ser Leu Lys
            325

<210> SEQ ID NO 14
<211> LENGTH: 317
<212> TYPE: PRT
<213> ORGANISM: Streptococcus pneumoniae
<220> FEATURE:
<221> NAME/KEY: misc_feature
<223> OTHER INFORMATION: CDC0288-04

<400> SEQUENCE: 14

Met Asp Arg Glu Pro Val Thr Val Arg Ser Tyr Ala Asn Ile Ala Ile
1               5                   10                  15

Ile Lys Tyr Trp Gly Lys Lys Glu Lys Glu Met Val Pro Ala Thr
            20                  25                  30

Ser Ser Ile Ser Leu Thr Leu Glu Asn Met Tyr Thr Glu Thr Thr Leu
            35                  40                  45

Ser Pro Leu Pro Ala Asn Val Thr Ala Asp Glu Phe Tyr Ile Asn Gly
    50                  55                  60

Gln Leu Gln Asn Glu Val Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Gly Leu Ser
                100                 105                 110

Ala Leu Val Lys Ala Cys Asn Ala Tyr Phe Lys Leu Gly Leu Asp Arg
            115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Ile Tyr Leu Lys Glu Asn Asp Phe Ala Lys
    210                 215                 220

Ile Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Ala Phe Val Arg Gln Leu Arg Glu Lys Gly Glu Ala Cys Tyr
            260                 265                 270

Phe Thr Met Asp Ala Gly Pro Asn Val Lys Val Phe Cys Gln Glu Lys
        275                 280                 285

Asp Leu Glu His Leu Ser Glu Ile Phe Gly Gln Arg Tyr Arg Leu Ile
    290                 295                 300

Val Ser Lys Thr Lys Asp Leu Ser Gln Asp Asp Cys Cys
305                 310                 315

<210> SEQ ID NO 15

```
<211> LENGTH: 314
<212> TYPE: PRT
<213> ORGANISM: Streptococcus pyogenes
<220> FEATURE:
<221> NAME/KEY: misc_feature
<223> OTHER INFORMATION: Serotype M6 (ATCC BAA-946 / MGAS10394)

<400> SEQUENCE: 15
```

Met Asp Pro Asn Val Ile Thr Val Thr Ser Tyr Ala Asn Ile Ala Ile
1               5                   10                  15

Ile Lys Tyr Trp Gly Lys Glu Asn Gln Ala Lys Met Ile Pro Ser Thr
            20                  25                  30

Ser Ser Ile Ser Leu Thr Leu Glu Asn Met Phe Thr Thr Thr Ser Val
        35                  40                  45

Ser Phe Leu Pro Asp Thr Ala Thr Ser Asp Gln Phe Tyr Ile Asn Gly
    50                  55                  60

Val Leu Gln Asn Asp Glu Glu His Thr Lys Ile Ser Ala Ile Ile Asp
65                  70                  75                  80

Gln Phe Arg Gln Pro Gly Gln Ala Phe Val Lys Met Glu Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asp Gln Leu Phe Asn Thr Gln Leu Asp Gln
        115                 120                 125

Lys Ala Leu Ala Gln Lys Ala Lys Phe Ala Ser Gly Ser Ser Ser Arg
    130                 135                 140

Ser Phe Phe Gly Pro Val Ala Ala Trp Asp Lys Asp Ser Gly Ala Ile
145                 150                 155                 160

Tyr Lys Val Glu Thr Asp Leu Lys Met Ala Met Ile Met Leu Val Leu
                165                 170                 175

Asn Ala Ala Lys Lys Pro Ile Ser Ser Arg Glu Gly Met Lys Leu Cys
            180                 185                 190

Arg Asp Thr Ser Thr Thr Phe Asp Glu Trp Val Glu Gln Ser Ala Ile
        195                 200                 205

Asp Tyr Gln His Met Leu Thr Tyr Leu Lys Thr Asn Asn Phe Glu Lys
    210                 215                 220

Val Gly Gln Leu Thr Glu Ala Asn Ala Leu Ala Met His Ala Thr Thr
225                 230                 235                 240

Lys Thr Ala Asn Pro Pro Phe Ser Tyr Leu Thr Lys Glu Ser Tyr Gln
                245                 250                 255

Ala Met Glu Ala Val Lys Glu Leu Arg Gln Glu Gly Phe Ala Cys Tyr
            260                 265                 270

Phe Thr Met Asp Ala Gly Pro Asn Val Lys Val Leu Cys Leu Glu Lys
        275                 280                 285

Asp Leu Ala Gln Leu Ala Glu Arg Leu Gly Lys Asn Tyr Arg Ile Ile
    290                 295                 300

Val Ser Lys Thr Lys Asp Leu Pro Asp Val
305                 310

```
<210> SEQ ID NO 16
<211> LENGTH: 324
<212> TYPE: PRT
<213> ORGANISM: Picrophilus torridus
<220> FEATURE:
<221> NAME/KEY: misc_feature
<223> OTHER INFORMATION: DSM 9790

<400> SEQUENCE: 16
```

```
Met Glu Asn Tyr Asn Val Lys Thr Arg Ala Phe Pro Thr Ile Gly Ile
1               5                   10                  15

Ile Leu Leu Gly Gly Ile Ser Asp Lys Lys Asn Arg Ile Pro Leu His
            20                  25                  30

Thr Thr Ala Gly Ile Ala Tyr Thr Gly Ile Asn Asn Asp Val Tyr Thr
        35                  40                  45

Glu Thr Lys Leu Tyr Val Ser Lys Asp Glu Lys Cys Tyr Ile Asp Gly
    50                  55                  60

Lys Glu Ile Asp Leu Asn Ser Asp Arg Ser Pro Ser Lys Val Ile Asp
65                  70                  75                  80

Lys Phe Lys His Glu Ile Leu Met Arg Val Asn Leu Asp Glu Asn
            85                  90                  95

Asn Leu Ser Ile Asp Ser Arg Asn Phe Asn Ile Leu Ser Gly Ser Ser
            100                 105                 110

Asp Ser Gly Ala Ala Ala Leu Gly Glu Cys Ile Glu Ser Ile Phe Glu
        115                 120                 125

Tyr Asn Ile Asn Ile Phe Thr Phe Glu Asn Asp Leu Gln Arg Ile Ser
    130                 135                 140

Glu Ser Val Gly Arg Ser Leu Tyr Gly Gly Leu Thr Val Asn Tyr Ala
145                 150                 155                 160

Asn Gly Arg Glu Ser Leu Thr Glu Pro Leu Leu Glu Pro Glu Ala Phe
            165                 170                 175

Asn Asn Phe Thr Ile Ile Gly Ala His Phe Asn Ile Asp Arg Lys Pro
            180                 185                 190

Ser Asn Glu Ile His Glu Asn Ile Lys His Glu Asn Tyr Arg Glu
            195                 200                 205

Arg Ile Lys Ser Ala Glu Arg Lys Ala Lys Lys Leu Glu Glu Leu Ser
210                 215                 220

Arg Asn Ala Asn Ile Lys Gly Ile Phe Glu Leu Ala Glu Ser Asp Thr
225                 230                 235                 240

Val Glu Tyr His Lys Met Leu His Asp Val Gly Val Asp Ile Ile Asn
            245                 250                 255

Asp Arg Met Glu Asn Leu Ile Glu Arg Val Lys Glu Met Lys Asn Asn
            260                 265                 270

Phe Trp Asn Ser Tyr Ile Val Thr Gly Gly Pro Asn Val Phe Val Ile
            275                 280                 285

Thr Glu Lys Lys Asp Val Asp Lys Ala Met Glu Gly Leu Asn Asp Leu
            290                 295                 300

Cys Asp Asp Ile Arg Leu Leu Lys Val Ala Gly Lys Pro Gln Val Ile
305                 310                 315                 320

Ser Lys Asn Phe

<210> SEQ ID NO 17
<211> LENGTH: 320
<212> TYPE: PRT
<213> ORGANISM: Thermoplasma volcanium

<400> SEQUENCE: 17

Met Ser Asn Ser Ser Ile Thr Ser Val Ala Tyr Pro Thr Ile Gly Val
1               5                   10                  15

Val Leu Leu Gly Gly Ile Ala Asn Glu Lys Thr Arg Thr Pro Leu His
            20                  25                  30

Thr Ser Ala Gly Ile Ala Tyr Thr Asp Ser Cys Gly Ser Ile Arg Thr
        35                  40                  45
```

-continued

Glu Ser Thr Ile Tyr Gly Asp Ser Glu Met His Ile Tyr Phe Asn Gly
    50                  55                  60

Thr Glu Ser Lys Asp Glu Asn Arg Ser Val Lys Ser Val Leu Glu Arg
65                  70                  75                  80

Tyr Arg Asn Glu Leu Gln Ser Phe Phe Gly Lys Lys Asp Val Ser Tyr
                85                  90                  95

Ser Ser Leu Asn Tyr Gly Ile Leu Ser Gly Ser Ser Asp Ala Gly Ala
            100                 105                 110

Ala Ser Ile Gly Ala Ile Leu Ser Phe Ile Asp Lys Lys Asn Asp Ile
        115                 120                 125

His Asp Ile Glu Asn Asp Ile Arg Met Ile Ser Glu Ser Ala Gly Arg
    130                 135                 140

Ser Leu His Gly Gly Leu Thr Ile Thr Trp Ser Asp Gly Tyr Ser Ala
145                 150                 155                 160

Tyr Thr Glu Arg Val Leu Gly Pro Glu His Phe Asn Asn Tyr Ala Ile
                165                 170                 175

Val Gly Phe Ser Phe Asp Tyr Pro Arg Asn Pro Ser Asp Thr Ile His
            180                 185                 190

Gln Asn Ile Ile Lys Ser Lys Arg Tyr Lys Gln Arg Thr Ile Asp Ala
        195                 200                 205

Asp Glu His Ala His Glu Ile Lys Glu Met Ala Arg Thr Asp Asp Ile
    210                 215                 220

Glu Gly Ile Phe Glu Lys Ala Glu Asp Thr Glu Glu Tyr His Ser
225                 230                 235                 240

Ile Leu Arg Glu Val Gly Val Leu Val Ile Arg Glu Asn Met Gln Lys
                245                 250                 255

Leu Ile Glu Phe Ile Lys Ile Leu Arg Lys Glu Phe Trp Asn Ser Tyr
            260                 265                 270

Ile Val Thr Gly Gly Ser Asn Val Tyr Val Ile Val Arg Arg Asp Asp
        275                 280                 285

Leu Glu Arg Leu Ile His Ile Lys Asn Thr Phe Gly Ser Lys Pro Lys
    290                 295                 300

Ile Leu Asn Val Ala Gly Pro Ala Trp Ile Lys Lys Val Glu Ser Asp
305                 310                 315                 320

<210> SEQ ID NO 18
<211> LENGTH: 318
<212> TYPE: PRT
<213> ORGANISM: Thermoplasma acidophilum

<400> SEQUENCE: 18

Met Thr Tyr Arg Ser Ile Gly Ser Thr Ala Tyr Pro Thr Ile Gly Val
1               5                   10                  15

Val Leu Leu Gly Gly Ile Ala Asn Pro Val Thr Arg Thr Pro Leu His
            20                  25                  30

Thr Ser Ala Gly Ile Ala Tyr Ser Asp Ser Cys Gly Ser Ile Arg Ser
        35                  40                  45

Glu Thr Arg Ile Tyr Ala Asp Glu Ala Thr His Ile Tyr Phe Asn Gly
    50                  55                  60

Thr Glu Ser Thr Asp Asp Asn Arg Ser Val Arg Val Leu Asp Arg
65                  70                  75                  80

Tyr Ser Ser Val Phe Glu Glu Ala Phe Gly Thr Lys Thr Val Ser Tyr
                85                  90                  95

Ser Ser Gln Asn Phe Gly Ile Leu Ser Gly Ser Ser Asp Ala Gly Ala

```
            100                 105                 110
Ala Ser Ile Gly Ala Ala Ile Leu Gly Leu Lys Pro Asp Leu Asp Pro
        115                 120                 125

His Asp Val Glu Asn Asp Leu Arg Ala Val Ser Glu Ser Ala Gly Arg
130                 135                 140

Ser Leu Phe Gly Gly Leu Thr Ile Thr Trp Ser Asp Gly Phe His Ala
145                 150                 155                 160

Tyr Thr Glu Lys Ile Leu Asp Pro Glu Ala Phe Ser Gly Tyr Ser Ile
                165                 170                 175

Val Ala Phe Ala Phe Asp Tyr Gln Arg Asn Pro Ser Asp Val Ile His
            180                 185                 190

Gln Asn Ile Val Arg Ser Asp Leu Tyr Pro Ala Arg Lys Lys His Ala
        195                 200                 205

Asp Glu His Ala His Met Ile Lys Glu Tyr Ala Lys Thr Asn Asp Ile
    210                 215                 220

Lys Gly Ile Phe Asp Leu Ala Gln Glu Asp Thr Glu Glu Tyr His Ser
225                 230                 235                 240

Ile Leu Arg Gly Val Gly Val Asn Val Ile Arg Glu Asn Met Gln Lys
                245                 250                 255

Leu Ile Ser Tyr Leu Lys Leu Ile Arg Lys Asp Tyr Trp Asn Ala Tyr
            260                 265                 270

Ile Val Thr Gly Gly Ser Asn Val Tyr Val Ala Val Glu Ser Glu Asn
        275                 280                 285

Ala Asp Arg Leu Phe Ser Ile Glu Asn Thr Phe Gly Ser Lys Lys Lys
    290                 295                 300

Met Leu Arg Ile Val Gly Gly Ala Trp His Arg Arg Pro Glu
305                 310                 315

<210> SEQ ID NO 19
<211> LENGTH: 322
<212> TYPE: PRT
<213> ORGANISM: Ferroplasma acidarmanus
<220> FEATURE:
<221> NAME/KEY: misc_feature
<223> OTHER INFORMATION: fer1

<400> SEQUENCE: 19

Met Glu Lys Tyr Tyr Val Glu Val Lys Ala Tyr Pro Thr Ile Gly Ile
1               5                   10                  15

Leu Leu Leu Gly Gly Val Ser Asp Asn Lys Lys Arg Leu Pro Arg His
            20                  25                  30

Thr Thr Ala Gly Ile Ala Tyr Thr Gly Leu Asp Asp Ile Tyr Val
        35                  40                  45

Lys Thr Asp Leu Tyr Leu Ser Asn Gln Lys Ser Gly Ile Ile Asn Gly
50                  55                  60

Lys Glu Val Ser Pro Asp Ser Pro Arg Ser Phe Val Val Ile Asp
65                  70                  75                  80

Lys Tyr Arg His Glu Ile Leu Met Arg His Pro Glu Tyr Ser Glu Val
                85                  90                  95

Ser Phe Val Ser Glu Asn Lys Asn Val Ile Ser Gly Ser Ser Asp Ala
            100                 105                 110

Gly Ala Ala Ala Ile Gly Glu Cys Ile Gln Ser Ile Phe Glu Tyr Asn
        115                 120                 125

Ile Asn Ile Phe Asn Phe Glu Asn Asp Leu Gln Gln Ile Ser Glu Ser
    130                 135                 140
```

Ala Gly Arg Ser Met Phe Gly Gly Phe Thr Ile Asn His Ala Asn Gly
145                 150                 155                 160

Lys Glu Ser Leu Thr Asp Glu Ile Leu Gly Pro Glu Asp Phe Glu Asp
                165                 170                 175

Phe Val Ile Val Ala Cys Lys Phe Ser Glu Asp Arg Lys Pro Ser Asp
            180                 185                 190

Thr Ile His Ser Asn Ile Ile Asn His Glu Lys Tyr Ala Glu Arg Val
        195                 200                 205

Lys Asn Ser Glu Leu Arg Ala Lys Glu Leu Glu Lys Met Ala Asp Ser
    210                 215                 220

Gly Asp Ile Lys Gly Ile Phe Glu Ala Gly Lys Asp Thr Gln Glu
225                 230                 235                 240

Tyr His Ser Met Leu Arg Glu Val Gly Val Ser Ile Ile Thr Asp Glu
                245                 250                 255

Met Gln Arg Leu Ile Glu Lys Val Glu Glu Leu Lys Ala Glu Phe Trp
            260                 265                 270

Asn Ala Tyr Ile Val Thr Gly Gly Thr Asn Val Phe Val Ala Val Glu
        275                 280                 285

Arg Lys Asn Met Glu Lys Met Lys Asn Ala Ala Met Glu Phe Lys Cys
    290                 295                 300

Thr Pro Val Tyr Leu Lys Val Ala Gly Lys Pro Asp Val Ile Ser Lys
305                 310                 315                 320

Asn Phe

<210> SEQ ID NO 20
<211> LENGTH: 993
<212> TYPE: DNA
<213> ORGANISM: P. torridus
<220> FEATURE:
<221> NAME/KEY: misc_feature
<223> OTHER INFORMATION: AAT43941 (including a His Tag)

<400> SEQUENCE: 20

```
atgcatcatc accatcacca tgaaaattac aatgttaaga caagggcgtt cccaacaata      60
ggcataatac tgcttggtgg gatctcggat aaaaagaaca ggataccgct gcatacaacg     120
gcaggcatag catatactgg tataaacaat gatgtttaca ctgagacaaa gctttatgta     180
tcaaaagatg aaaaatgcta tattgatgga aaggaaattg atttaaattc agatagatca     240
ccatcgaagg ttattgataa attcaagcat gaaatactta tgagagtaaa tcttgatgat     300
gaaaataacc tttcaattga ttcaaggaac tttaatatat taagtggcag ctcagattct     360
ggggccgctg cactgggaga gtgcatagaa tcatttttg aatacaatat aaatatattt     420
acatttgaaa acgatcttca gaggatatca gaaagtgttg aagaagcct ttacggtggt     480 ttaacagtaa actatgccaa tggcagggaa tcattaacag agccattact tgagcctgag     540
gcatttaata actttacaat aattggtgca cattttaaca ttgatagaaa accatcaaat     600
gagattcatg aaaatatcat aaaacatgaa attacagggg aaagaataaa aagtgctgag     660
agaaaggcga aaaacttga ggagctatca aggaatgcaa acataaaggg tatctttgaa     720
cttgcagaat ccgatacagt ggaataccat aaaatgctcc atgatgttgg cgttgacata     780
ataaatgata gaatggagaa cctcattgaa agggtaaaag aaatgaaaaa taacttctgg     840
aattcataca tagttaccgg cggcccgaac gttttttgtaa taacagagaa aaaggacgtt     900
gataaggcaa tggaaggatt aaatgatctg tgcgatgata taagattatt aaaagttgca     960
ggaaagccac aggtcatttc aaaaaactt taa                                    993
```

<210> SEQ ID NO 21
<211> LENGTH: 996
<212> TYPE: DNA
<213> ORGANISM: P. torridus
<220> FEATURE:
<221> NAME/KEY: misc_feature
<223> OTHER INFORMATION: Codon optimised sequence of P. torridus
      (AAT43941) (including a His Tag)

<400> SEQUENCE: 21

```
atgcatcatc atcatcacca cgagaactat aatgttaaaa cccgtgcatt tccgaccatt      60
ggtattattc tgctgggtgg cattagcgac aaaaaaaacc gtattccgct gcataccacc     120
gcaggtattg catataccgg catcaataac gatgtgtaca ccgaaaccaa actgtatgtg     180
agcaaagacg aaaaatgcta tatcgatggc aaagaaatcg atctgaatag cgatcgtagc     240
ccgagcaaag tgatcgataa attcaaacat gaaatcctga tgcgtgtgaa tctggatgat     300
gaaaacaacc tgagcattga tagccgcaat tttaacattc tgagcggtag cagcgatagc     360
ggtgcagcag cactgggtga atgcattgaa agcatcttcg agtacaacat caacatcttc     420
acctttgaaa atgatctgca gcgtattagc gaaagcgttg gtcgtagcct gtatggtggt     480
ctgaccgtta attatgcaaa tggtcgtgaa agcctgaccg aaccgctgct ggaaccggaa     540
gcatttaaca actttaccat catcggtgcc cattttaaca ttgatcgcaa accgagcaac     600
gaaatccacg aaaacatcat caaacatgag aactatcgcg aacgtattaa agcgcagag    660
cgcaaagcaa aaaactgga gaactgagc cgtaatgcca acattaaagg cattttgaa    720
ctggcagaaa gcgataccgt ggaatatcat aaaatgctgc atgatgtggg cgttgatatt     780
atcaatgacc gcatggaaaa tctgattgaa cgcgtgaaag atgaaaaaa caacttctgg     840
aacagctata ttgttaccgg tggtccgaat gttttttgtga tcaccgagaa aaaagatgtg     900
gataaagcca tggaaggtct gaatgatctg tgtgatgata ttcgtctgct gaaagttgca     960
ggtaaaccgc aggttatcag caaaaacttc taatga                              996
```

<210> SEQ ID NO 22
<211> LENGTH: 315
<212> TYPE: PRT
<213> ORGANISM: Streptococcus gordonii
<220> FEATURE:
<221> NAME/KEY: misc_feature
<223> OTHER INFORMATION: str. Challis substr. CH1

<400> SEQUENCE: 22

Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
            20                  25                  30

Ser Ser Ile Ser Leu Thr Leu Glu Asn Met Tyr Thr Glu Thr Gln Leu
        35                  40                  45

Ser Pro Leu Pro Asp Thr Ala Thr Gly Asp Glu Phe Tyr Ile Asp Gly
    50                  55                  60

Gln Leu Gln Ser Pro Ala Glu His Ala Lys Ile Ser Lys Ile Ile Asp
65                  70                  75                  80

Arg Phe Arg Ser Pro Glu Asp Gly Phe Val Arg Val Asp Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Thr Gly Tyr Gln Thr
            115                 120                 125

Glu Glu Leu Ala Gln Leu Ala Lys Phe Ala Ser Gly Ser Ser Ala Arg
    130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Ala Gln Ser Ala Leu
        195                 200                 205

Asp Tyr Gln Ala Met Leu Gly Tyr Leu Gln Asp Asn Asp Phe Ala Lys
    210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255

Ala Met Asp Ala Val Arg Lys Leu Arg Glu Gln Gly Glu Arg Cys Tyr
            260                 265                 270

Phe Thr Met Asp Ala Gly Pro Asn Val Lys Val Leu Cys Leu Glu Glu
        275                 280                 285

Asp Leu Asp His Leu Ala Ala Ile Phe Glu Lys Asp Tyr Arg Leu Ile
    290                 295                 300

Val Ser Lys Thr Lys Asp Leu Ser Asp Glu Ser
305                 310                 315

<210> SEQ ID NO 23
<211> LENGTH: 311
<212> TYPE: PRT
<213> ORGANISM: Streptococcus infantarius
<220> FEATURE:
<221> NAME/KEY: misc_feature
<223> OTHER INFORMATION: subsp infantarius ATCC BAA-102

<400> SEQUENCE: 23

Met Asp Arg Lys Ile Val Thr Val Lys Ser Tyr Ala Asn Ile Ala Ile
1               5                   10                  15

Ile Lys Tyr Trp Gly Lys Ala Asp Ala Ala Lys Met Ile Pro Ala Thr
            20                  25                  30

Ser Ser Ile Ser Leu Thr Leu Glu Asn Met Phe Thr Thr Thr Ser Val
        35                  40                  45

Ser Phe Leu Pro Asp Ser Ala Ser His Asp Glu Phe Tyr Ile Asn Gly
    50                  55                  60

Val Leu Gln Asp Asp Lys Glu His Ala Lys Ile Ser Ala Ile Ile Asp
65                  70                  75                  80

Gln Tyr Arg Gly Gln Arg Ser Glu Tyr Val Lys Val Glu Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Glu Leu Phe Glu Thr Gly Leu Thr Arg
        115                 120                 125

Ala Glu Leu Ala Gln Lys Ala Lys Phe Ala Ser Gly Ser Ser Ser Arg
    130                 135                 140

Ser Phe Phe Gly Pro Leu Ala Ala Trp Asp Lys Asp Ser Gly Glu Val
145                 150                 155                 160

```
Tyr Pro Val Gln Thr Asp Leu Lys Leu Ala Met Ile Met Leu Val Leu
                165                 170                 175

Ser Asp Ser Lys Lys Ser Ile Ser Ser Arg Glu Gly Met Lys Arg Cys
            180                 185                 190

Val Glu Thr Ser Thr Thr Phe Ala Asp Trp Val Lys Gln Ser Glu Gln
        195                 200                 205

Asp Tyr Lys Asp Met Leu Gly Tyr Leu Lys Asn Asn Asp Phe Glu Arg
    210                 215                 220

Val Gly Glu Leu Thr Glu Arg Asn Ala Leu Ala Met His Asp Thr Asn
225                 230                 235                 240

Thr His Ala Asn Pro Pro Phe Asn Tyr Leu Thr Glu Glu Ser Tyr Lys
                245                 250                 255

Ala Met Glu Phe Val Lys Gln Leu Arg Ser Glu Gly Leu Lys Cys Tyr
            260                 265                 270

Phe Thr Met Asp Ala Gly Pro Asn Val Lys Val Leu Cys Leu Glu Glu
        275                 280                 285

Asp Leu Glu Arg Leu Thr Lys Arg Phe Glu Glu Asn Tyr Arg Val Ile
    290                 295                 300

Val Ser Arg Thr Lys Glu Leu
305                 310

<210> SEQ ID NO 24
<211> LENGTH: 317
<212> TYPE: PRT
<213> ORGANISM: Streptococcus mitis
<220> FEATURE:
<221> NAME/KEY: misc_feature
<223> OTHER INFORMATION: strain B6

<400> SEQUENCE: 24

Met Asp Arg Glu Pro Val Thr Val Arg Ser Tyr Ala Asn Ile Ala Ile
1               5                   10                  15

Ile Lys Tyr Trp Gly Lys Lys Lys Glu Lys Met Val Pro Ala Thr
            20                  25                  30

Ser Ser Ile Ser Leu Thr Leu Glu Asn Met Tyr Thr Glu Thr Thr Leu
        35                  40                  45

Ser Ser Leu Pro Thr Asp Ala Thr Ala Asp Ala Phe Tyr Ile Asn Gly
    50                  55                  60

Gln Leu Gln Asn Glu Ala Glu His Val Lys Met Ser Lys Ile Ile Asp
65                  70                  75                  80

Arg Tyr Arg Pro Asp Gly Asp Gly Phe Val Arg Ile Asp Thr Gln Asn
                85                  90                  95

Ser Met Pro Thr Ala Ala Gly Leu Ser Ser Ser Ser Gly Leu Ser
            100                 105                 110

Ala Leu Val Lys Ala Cys Asn Ala Tyr Phe Lys Leu Gly Leu Asn Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Gly Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
```

```
            195                 200                 205
Asp Tyr Gln Asp Met Leu Val Tyr Leu Lys Ala Asn Asp Phe Ala Lys
210                 215                 220

Val Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Asp Phe Val Arg Gln Leu Arg Glu Gln Gly Glu Ala Cys Tyr
                260                 265                 270

Phe Thr Met Asp Ala Gly Pro Asn Val Lys Val Leu Cys Gln Glu Lys
                275                 280                 285

Asp Leu Glu His Leu Ser Glu Ile Phe Gly Gln Arg Tyr Arg Leu Ile
            290                 295                 300

Val Ser Lys Thr Lys Asp Leu Ser Gln Asp Gly Cys Cys
305                 310                 315

<210> SEQ ID NO 25
<211> LENGTH: 316
<212> TYPE: PRT
<213> ORGANISM: Streptococcus gallolyticus
<220> FEATURE:
<221> NAME/KEY: misc_feature
<223> OTHER INFORMATION: UCN34

<400> SEQUENCE: 25

Met Asp Arg Lys Ile Val Thr Val Lys Ser Tyr Ala Asn Ile Ala Ile
1               5                   10                  15

Ile Lys Tyr Trp Gly Lys Ala Asp Ala Val Lys Met Ile Pro Ala Thr
                20                  25                  30

Ser Ser Ile Ser Leu Thr Leu Glu Asn Met Phe Thr Thr Thr Thr Val
            35                  40                  45

Ser Phe Leu Pro Gln Ser Val Gly His Asp Glu Phe Tyr Ile Asn Gly
        50                  55                  60

Val Leu Gln Asp Glu Lys Glu His Ala Lys Ile Ser Ala Ile Ile Asp
65                  70                  75                  80

Gln Tyr Arg Gly Gly Arg Ser Glu Phe Val Lys Val Glu Thr Ser Asn
                85                  90                  95

Asn Met Pro Thr Ala Ala Gly Leu Ser Ser Ser Ser Gly Leu Ser
                100                 105                 110

Ala Leu Val Lys Ala Cys Asn Glu Leu Phe Glu Thr Gly Leu Asn Gln
            115                 120                 125

Ser Glu Leu Ala Gln Lys Ala Lys Phe Ala Ser Gly Ser Ser Ser Arg
        130                 135                 140

Ser Phe Phe Gly Pro Ile Ala Ala Trp Asp Lys Asp Ser Gly Asp Ile
145                 150                 155                 160

Tyr Pro Val Gln Thr Asp Leu Lys Leu Ala Met Ile Met Leu Val Leu
                165                 170                 175

Ser Asp Ser Lys Lys Pro Ile Ser Ser Arg Glu Gly Met Lys Arg Cys
                180                 185                 190

Ala Glu Thr Ser Thr Thr Phe Ala Asp Trp Val Lys Gln Ser Glu Gln
            195                 200                 205

Asp Tyr Lys Asp Met Leu Ala Tyr Leu Lys Ala Asn Asp Phe Glu Lys
        210                 215                 220

Val Gly Glu Leu Thr Glu Arg Asn Ala Leu Ala Met His Asp Thr Asn
225                 230                 235                 240
```

```
Thr His Ala Asn Pro Pro Phe Asn Tyr Leu Thr Asp Glu Thr Tyr Ala
                245                 250                 255

Ala Met Asp Phe Val Lys Ser Leu Arg Thr Gln Gly Glu Lys Cys Tyr
            260                 265                 270

Phe Thr Met Asp Ala Gly Pro Asn Val Lys Val Leu Cys Leu Glu Glu
        275                 280                 285

Asp Leu Glu Cys Leu Thr Lys Arg Phe Glu Glu Asn Tyr Arg Val Ile
    290                 295                 300

Ala Ser Arg Thr Lys Val Leu Pro Asp Glu Asn Asp
305                 310                 315

<210> SEQ ID NO 26
<211> LENGTH: 315
<212> TYPE: PRT
<213> ORGANISM: Streptococcus sanguinis
<220> FEATURE:
<221> NAME/KEY: misc_feature
<223> OTHER INFORMATION: SK36

<400> SEQUENCE: 26

Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
            20                  25                  30

Ser Ser Ile Ser Leu Thr Leu Glu Asn Met Tyr Thr Glu Thr Gln Leu
        35                  40                  45

Ser Pro Leu Pro Asp Thr Ala Thr Gly Asp Glu Phe Tyr Ile Asp Ser
    50                  55                  60

Gln Leu Gln Ser Pro Ala Glu His Ala Lys Ile Ser Lys Ile Ile Asp
65                  70                  75                  80

Arg Phe Arg Ser Pro Glu Asp Gly Phe Val Arg Val Asp Thr Ser Asn
                85                  90                  95

Asn Met Pro Thr Ala Ala Gly Leu Ser Ser Ser Ser Ser Gly Leu Ser
            100                 105                 110

Ala Leu Val Lys Ala Cys Asn Ala Tyr Phe Gln Thr Gly Tyr Gln Thr
        115                 120                 125

Gln Glu Leu Ala Gln Leu Ala Lys Phe Ala Ser Gly Ser Ser Ala Arg
    130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Ala Gln Ser Ala Leu
        195                 200                 205

Asp Tyr Lys Ala Met Leu Ser Tyr Leu Gln Asp Asn Asp Phe Ala Lys
    210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255

Ala Met Asp Ala Val Arg Lys Leu Arg Glu Gln Gly Glu Arg Cys Tyr
            260                 265                 270

Phe Thr Met Asp Ala Gly Pro Asn Val Lys Val Leu Cys Leu Glu Glu
        275                 280                 285
```

```
Asp Leu Asp His Leu Val Ala Ile Phe Glu Lys Asp Tyr Arg Leu Ile
        290                 295                 300

Val Ser Lys Thr Lys Asp Leu Ser Asp Glu Asp
305                 310                 315

<210> SEQ ID NO 27
<211> LENGTH: 317
<212> TYPE: PRT
<213> ORGANISM: Streptococcus
<220> FEATURE:
<221> NAME/KEY: misc_feature
<223> OTHER INFORMATION: sp. M143

<400> SEQUENCE: 27

Met Asp Arg Lys Pro Val Thr Val Arg Ser Tyr Ala Asn Ile Ala Ile
1               5                   10                  15

Ile Lys Tyr Trp Gly Lys Lys Glu Lys Glu Met Val Pro Ala Thr
            20                  25                  30

Ser Ser Ile Ser Leu Thr Leu Glu Asn Met Tyr Thr Glu Thr Thr Leu
        35                  40                  45

Ser Pro Leu Pro Thr Asp Ala Thr Ala Asp Ala Phe Tyr Ile Asn Gly
50                  55                  60

Gln Leu Gln Ser Glu Ala His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Leu Gly Leu Asn Arg
            115                 120                 125

Ser Gln Leu Ala Gln Glu Ala Lys Phe Ala Ser Gly Ser Ser Ser Arg
130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Leu Tyr Leu Lys Glu Asn Asp Phe Ala Lys
210                 215                 220

Val Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Asp Phe Val Arg Gln Leu Arg Glu Gln Gly Ser Cys Tyr
            260                 265                 270

Phe Thr Met Asp Ala Gly Pro Asn Val Lys Val Leu Cys Gln Glu Glu
        275                 280                 285

Asp Leu Glu His Leu Ser Glu Ile Phe Gly Gln Arg Tyr Arg Leu Ile
290                 295                 300

Val Ser Lys Thr Lys Asp Leu Ser Gln Asp Asp Cys Cys
305                 310                 315
```

<210> SEQ ID NO 28
<211> LENGTH: 341
<212> TYPE: PRT
<213> ORGANISM: Streptococcus suis
<220> FEATURE:
<221> NAME/KEY: misc_feature
<223> OTHER INFORMATION: 89/1591

<400> SEQUENCE: 28

```
Met Thr Lys Gln Ile Gly Ile Ala Arg Ala His Thr Asn Ile Ala Leu
1               5                   10                  15

Ile Lys Tyr Trp Gly Lys Arg Asp Lys Glu Leu Phe Leu Pro Met Asn
            20                  25                  30

Ser Ser Leu Ser Leu Thr Leu Asp Ala Phe Tyr Thr Asp Thr Lys Val
        35                  40                  45

Val Phe Asp Pro Glu Leu Thr Ala Asp Glu Phe Tyr Leu Asn Gly Met
    50                  55                  60

Leu Gln Lys Glu Lys Glu Ile Leu Lys Ile Ser Arg Phe Leu Asp Leu
65                  70                  75                  80

Phe Cys Glu Tyr Ile Gly Glu Arg Ala Phe Ala Arg Val Glu Ser Leu
                85                  90                  95

Asn Phe Val Pro Thr Ala Ala Gly Leu Ala Ser Ser Ala Ser Ala Phe
            100                 105                 110

Ala Ala Leu Ala Leu Ala Thr Ala Thr Ala Leu Asp Leu Asp Leu Ser
        115                 120                 125

Pro Ala Thr Leu Ser Thr Leu Ala Arg Arg Gly Ser Gly Ser Ser Thr
    130                 135                 140

Arg Ser Leu Phe Gly Gly Phe Val Glu Trp Asp Met Gly Thr Gly Ser
145                 150                 155                 160

Glu Asp Ser Met Ala His Pro Ile Asp Asp Ala Asp Trp Asp Ile Gly
                165                 170                 175

Met Val Val Leu Ala Val Asn Thr Gly Pro Lys Lys Ile Ala Ser Arg
            180                 185                 190

Glu Gly Met Asp His Thr Val Ala Thr Ser Pro Phe Tyr Ser Ala Trp
        195                 200                 205

Val Asp Thr Ala Lys Gln Asp Leu Ala Asp Ile Lys Ala Ala Ile Ala
    210                 215                 220

Gly Arg Asp Phe Glu Lys Leu Gly Gln Ile Thr Glu His Asn Gly Met
225                 230                 235                 240

Lys Met His Ala Thr Thr Leu Ser Ala Asn Pro Pro Phe Thr Tyr Trp
                245                 250                 255

Ser Ala Asp Ser Leu Val Ala Gln Glu Ala Val Arg Gln Val Arg Glu
            260                 265                 270

Ala Thr Gly Leu Ser Ala Tyr Met Thr Met Asp Ala Gly Pro Asn Val
        275                 280                 285

Lys Val Leu Cys Arg Ala Ser Gln Met Asp Glu Leu Val Ala Glu Leu
    290                 295                 300

Ala Lys Val Phe Pro Arg Glu Lys Ile Ile Thr Ser Lys Pro Gly Pro
305                 310                 315                 320

Ala Ala Tyr Val Leu Ser Glu Asp Glu Trp Gln Thr Ser Gln Ala Ala
                325                 330                 335

Phe Glu Lys Gly Leu
            340
```

<210> SEQ ID NO 29
<211> LENGTH: 314

<212> TYPE: PRT
<213> ORGANISM: Streptococcus salivarius
<220> FEATURE:
<221> NAME/KEY: misc_feature
<223> OTHER INFORMATION: SK126

<400> SEQUENCE: 29

Met Asp Arg Lys Pro Val Ser Val Lys Ser Tyr Ala Asn Ile Ala Ile
1               5                   10                  15

Val Lys Tyr Trp Gly Lys Ala Asp Ala Glu Arg Met Ile Pro Ser Thr
            20                  25                  30

Ser Ser Ile Ser Leu Thr Leu Glu Asn Met Tyr Thr Glu Thr Lys Leu
        35                  40                  45

Ser Phe Leu Pro Glu Asp Ala Thr Gly Asp Val Met Tyr Ile Asp Asp
    50                  55                  60

Glu Leu Gln Gly Lys Glu Thr Thr Lys Ala Ser Lys Val Leu Asp
65                  70                  75                  80

Leu Phe Arg Asn Asn Ser Asn Gln His Val Lys Ile Glu Thr Trp Asn
                85                  90                  95

Asn Met Pro Thr Ala Ala Gly Leu Ser Ser Ser Ser Gly Leu Ser
            100                 105                 110

Ala Leu Val Lys Ala Ala Asn Glu Leu Phe Gln Val Gly Lys Thr Gln
        115                 120                 125

Ser Glu Leu Ala Gln Ile Ala Lys Phe Ala Ser Gly Ser Ser Ser Arg
    130                 135                 140

Ser Phe Phe Gly Pro Leu Ala Ala Trp Asp Lys Asp Ser Gly Glu Val
145                 150                 155                 160

Tyr Pro Val Glu Thr Asp Leu Lys Leu Ala Met Ile Met Leu Val Leu
                165                 170                 175

Thr Asp Gln Lys Lys Pro Val Ser Ser Arg Asp Gly Met Lys Leu Cys
            180                 185                 190

Thr Glu Thr Ser Thr Ser Phe Pro Glu Trp Ile Lys Gln Ser Glu Leu
        195                 200                 205

Asp Tyr Lys Asp Met Leu Ala Tyr Leu Lys Ala Asn Asp Phe Gln Ala
    210                 215                 220

Val Gly Glu Leu Thr Glu Ala Asn Ala Leu Arg Met His Gln Thr Thr
225                 230                 235                 240

Ser Thr Ala Asn Pro Pro Phe Ser Tyr Leu Thr Glu Ala Ser Tyr Gln
                245                 250                 255

Ala Met Asp Lys Val Lys Ala Leu Arg Ala Ser Gly Glu Gln Cys Tyr
            260                 265                 270

Phe Thr Met Asp Ala Gly Pro Asn Val Lys Val Leu Cys Leu Glu Glu
        275                 280                 285

Asp Leu Asp Arg Leu Ala Glu His Phe Arg Lys Asp Tyr Gln Val Ile
    290                 295                 300

Val Ser Arg Thr Lys Glu Leu Pro Asp Ala
305                 310

<210> SEQ ID NO 30
<211> LENGTH: 564
<212> TYPE: PRT
<213> ORGANISM: Pueraria montana
<220> FEATURE:
<221> NAME/KEY: misc_feature
<223> OTHER INFORMATION: var. lobata

<400> SEQUENCE: 30

-continued

```
Met Cys Ala Thr Ser Ser Gln Phe Thr Gln Ile Thr Glu His Asn Ser
1               5                   10                  15

Arg Arg Ser Ala Asn Tyr Gln Pro Asn Leu Trp Asn Phe Glu Phe Leu
            20                  25                  30

Gln Ser Leu Glu Asn Asp Leu Lys Val Glu Lys Leu Glu Glu Lys Ala
        35                  40                  45

Thr Lys Leu Glu Glu Glu Val Arg Cys Met Ile Asn Arg Val Asp Thr
    50                  55                  60

Gln Pro Leu Ser Leu Leu Glu Leu Ile Asp Val Gln Arg Leu Gly
65                  70                  75                  80

Leu Thr Tyr Lys Phe Glu Lys Asp Ile Ile Lys Ala Leu Glu Asn Ile
                85                  90                  95

Val Leu Leu Asp Glu Asn Lys Lys Asn Lys Ser Asp Leu His Ala Thr
            100                 105                 110

Ala Leu Ser Phe Arg Leu Leu Arg Gln His Gly Phe Glu Val Ser Gln
            115                 120                 125

Asp Val Phe Glu Arg Phe Lys Asp Lys Glu Gly Phe Ser Gly Glu
        130                 135                 140

Leu Lys Gly Asp Val Gln Gly Leu Leu Ser Leu Tyr Glu Ala Ser Tyr
145                 150                 155                 160

Leu Gly Phe Glu Gly Glu Asn Leu Leu Glu Glu Ala Arg Thr Phe Ser
                165                 170                 175

Ile Thr His Leu Lys Asn Asn Leu Lys Glu Gly Ile Asn Thr Lys Val
                180                 185                 190

Ala Glu Gln Val Ser His Ala Leu Glu Leu Pro Tyr His Gln Arg Leu
            195                 200                 205

His Arg Leu Glu Ala Arg Trp Phe Leu Asp Lys Tyr Glu Pro Lys Glu
        210                 215                 220

Pro His His Gln Leu Leu Leu Glu Leu Ala Lys Leu Asp Phe Asn Met
225                 230                 235                 240

Val Gln Thr Leu His Gln Lys Glu Leu Gln Asp Leu Ser Arg Trp Trp
                245                 250                 255

Thr Glu Met Gly Leu Ala Ser Lys Leu Asp Phe Val Arg Asp Arg Leu
                260                 265                 270

Met Glu Val Tyr Phe Trp Ala Leu Gly Met Ala Pro Asp Pro Gln Phe
            275                 280                 285

Gly Glu Cys Arg Lys Ala Val Thr Lys Met Phe Gly Leu Val Thr Ile
        290                 295                 300

Ile Asp Asp Val Tyr Asp Val Tyr Gly Thr Leu Asp Glu Leu Gln Leu
305                 310                 315                 320

Phe Thr Asp Ala Val Glu Arg Trp Asp Val Asn Ala Ile Asn Thr Leu
                325                 330                 335

Pro Asp Tyr Met Lys Leu Cys Phe Leu Ala Leu Tyr Asn Thr Val Asn
            340                 345                 350

Asp Thr Ser Tyr Ser Ile Leu Lys Glu Lys Gly His Asn Asn Leu Ser
        355                 360                 365

Tyr Leu Thr Lys Ser Trp Arg Glu Leu Cys Lys Ala Phe Leu Gln Glu
    370                 375                 380

Ala Lys Trp Ser Asn Asn Lys Ile Ile Pro Ala Phe Ser Lys Tyr Leu
385                 390                 395                 400

Glu Asn Ala Ser Val Ser Ser Gly Val Ala Leu Leu Ala Pro Ser
                405                 410                 415

Tyr Phe Ser Val Cys Gln Gln Gln Glu Asp Ile Ser Asp His Ala Leu
```

-continued

```
                420                 425                 430
Arg Ser Leu Thr Asp Phe His Gly Leu Val Arg Ser Ser Cys Val Ile
        435                 440                 445

Phe Arg Leu Cys Asn Asp Leu Ala Thr Ser Ala Ala Glu Leu Glu Arg
        450                 455                 460

Gly Glu Thr Thr Asn Ser Ile Ile Ser Tyr Met His Glu Asn Asp Gly
465                 470                 475                 480

Thr Ser Glu Glu Gln Ala Arg Glu Glu Leu Arg Lys Leu Ile Asp Ala
                485                 490                 495

Glu Trp Lys Lys Met Asn Arg Glu Arg Val Ser Asp Ser Thr Leu Leu
                500                 505                 510

Pro Lys Ala Phe Met Glu Ile Ala Val Asn Met Ala Arg Val Ser His
        515                 520                 525

Cys Thr Tyr Gln Tyr Gly Asp Gly Leu Gly Arg Pro Asp Tyr Ala Thr
        530                 535                 540

Glu Asn Arg Ile Lys Leu Leu Leu Ile Asp Pro Phe Pro Ile Asn Gln
545                 550                 555                 560

Leu Met Tyr Val
```

PRODUCTION OF 1,3-DIENES BY ENZYMATIC CONVERSION OF 3-HYDROXYALK 4-ENOATES AND/OR 3-PHOSPHONOXYALK-4-ENOATES

This Application is a 371 National Phase filing of EP 2012075921 filed Dec. 18, 2012, which is a continuation of EP 11 194 704 which was filed on Dec. 20, 2011 and a nonprovisional of U.S. Ser. No. 61/578,058 filed Dec. 20, 2011, which are all incorporated by reference in their entirety.

The present invention relates to a method for generating 1,3-dienes through a biological process. More specifically, the invention relates to a method for producing 1,3-dienes (for example 1,3-butadiene or 2-methyl-1,3-butadiene (isoprene)) from molecules of the 3-hydroxyalk-4-enoate type or from 3-phosphonoxyalk-4-enoates.

1,3-dienes such as 1,3-butadiene or 2-methyl-1,3-butadiene (isoprene) are important molecules for the industry. Isoprene, for example, is a key compound for the tire industry, and also has many applications in the adhesives. It is produced chemically using several routes:
  Extractive distillation from oil (C5 cut)
  Dehydrogenation of iso-amylene
  Double dehydrogenation of isopentane
  Reaction of isobutene and formaldehyde
  Reaction of acetone and acetylene
  Propylene dimerization WO 2009/076676 reports a metabolic pathway to isoprene. The pathway is based on the dephosphorylation-dehydration of downstream intermediates in the mevalonate pathway, i.e. isoprenyl-pyrophosphate or prenyl-pyrophosphate. This process has the drawback of requiring going through the whole mevalonate pathway: double phosphorylation of mevalonate, followed by a decarboxylation-dehydration into isoprenyl-pyrophosphate, further isomerised into prenyl-pyrophosphate, and finally double dephosphorylation/dehydration into isoprene.

Butadiene (1,3-butadiene) is a conjugated diene with the formula $C_4H_6$. It is an important industrial chemical used as a monomer in the production of synthetic rubber, nylon, ABS (Acrylonitrile-butadiene-styrene), plastics, latex. There exist different possibilities to produce butadiene. Butadiene is, for example, produced as a by product of the steam cracking process used to produce ethylene and other olefins. In this process butadiene occurs in the C4 stream and is normally isolated from other byproducts by extraction into a polar aprotic solvent, such as acetonitrile, from which it is then stripped. Butadiene can also be produced by the catalytic dehydrogenation of normal butane or it can be produced from ethanol. In the latter case, two different processes are in use. In a single-step process, ethanol is converted to butadiene, hydrogen and water at 400-450° C. over a metal oxide catalyst (Kirshenbaum, I. (1978), Butadiene. In M. Grayson (Ed.), *Encyclopedia of Chemical Technology*, 3rd ed., vol. 4, pp. 313-337. New York: John Wiley & Sons). In a two-step process, ethanol is oxidized to acetaldehyde which reacts with additional ethanol over a tantalum-promoted porous silica catalyst at 325-350° C. to yield butadiene (Kirshenbaum, I. (1978), loc cit.). Butadiene can also be produced by catalytic dehydrogenation of normal butenes. WO2012/018624 (US2012/0021478) proposed on a theoretical level various pathways for the enzymatic production of 1,3-butadiene including a pathway involving the decarboxylation of 3-hydroxypent-4-enoate.

For the past two decades, genetic engineering technologies have made possible the modification of the metabolism of micro-organisms, and hence their use to produce key substances which they would otherwise produce at a low yield. By enhancing naturally occurring metabolic pathways, these technologies open up new ways to bio-produce numerous compounds of industrial relevance. Several industrial compounds such as amino-acids for animal feed, bio-degradable plastics or textile fibres are now routinely produced using genetically modified organisms.

There is still a need to provide environmentally friendly, cost efficient and simple methods for producing the above-mentioned compounds.

The present application addresses this need by the provision of the embodiments as specified in the claims.

The present invention is based on the design of a novel synthetic pathway for the synthesis of 1,3-diene compounds based on the conversion of 3-hydroxyalk-4-enoates and 3-phosphonoxyalk-4-enoates. The invention is based on the demonstration that said conversion can be carried out biologically, by using an enzyme catalyzing a decarboxylase reaction. The invention can be implemented in vitro, in cell-free systems, or by using organisms, in particular microorganisms. The invention also relates to the production of 1,3-diene compounds from a carbon source, and particularly a carbohydrate (in particular glucose), a polyol (in particular glycerol), a biodegradable polymer (in particular starch, cellulose, poly-3-hydroxyalkenoate) the carbon source being converted by a microorganism to a metabolic intermediate belonging to the 3-hydroxyalk-4-enoate family, which is then converted to 1,3-diene compound.

More specifically, the invention relates to a method for producing a 1,3-diene compound characterized in that it comprises a step of converting a 3-hydroxyalk-4-enoate in the presence of an enzyme having decarboxylase activity into a 1,3-diene compound. Thus, the method comprises the enzymatically catalyzed decarboxylation of a 3-hydroxyalk-4-enoate.

The term "3-hydroxyalk-4-enoate", as used herein, denotes a molecule which responds to the following general formula:

with 3<n<7, and comprising 3-hydroxypent-4-enoate as common motif (FIG. 1B) and optionally a methyl substitution on carbon 3 and carbon 4.

In a preferred embodiment, "3-hydroxyalk-4-enoate", as used herein, denotes a molecule responding to the following structural formula:

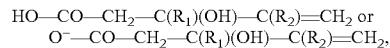

wherein $R_1$ and $R_2$ are selected, independently, from the group consisting of a hydrogen atom and a methyl group.

Carbon 3 is a chiral (stereogenic) center. The present definition encompasses the two chiral forms, even if one of the two forms, for example the R form, is the main form produced naturally. The suffix "oate", as used herein, can interchangeably denote either the carboxylate ion (COO—) or carboxylic acid (COOH). It is not used to denote an ester.

The term "diene" (or diolefin) as used herein denotes a hydrocarbon that contains two conjugated carbon double bonds, with a general formula of $C_nH_{2n-2}$, where n is an integer with 3<n<7, i.e. n can be 4, 5 or 6.

The term "1,3-diene", as used herein, denotes a molecule responding to the following structural formula $H_2C=C(R_1)-C(R_2)=CH_2$, wherein $R_1$ and $R_2$ are selected, independently, from the group consisting of a hydrogen atom and a methyl group.

In one particular embodiment the 3-hydroxyalk-4-enoate converted according to the method of the present invention is 3-hydroxypent-4-enoate and the resulting 1,3-diene compound is 1,3-butadiene.

In another embodiment the 3-hydroxyalk-4-enoate converted according to the method of the present invention is 3-hydroxy-4-methylpent-4-enoate or 3-hydroxy-3-methylpent-4-enoate and the resulting 1,3-diene compound is isoprene.

The term "enzyme having a decarboxylase activity" in the context of the present invention refers to an enzyme which is capable of decarboxylating a 3-hydroxyalk-4-enoate so as to lead to a 1,3-diene compound.

In one embodiment the enzyme having the activity of a decarboxylase is an enzyme which can be or is classified as a diphosphomevalonate decarboxylase or is an enzyme which is derived from such an enzyme and which has the capacity to decarboxylate a 3-hydroxyalk-4-enoate so as to produce a 1,3-diene compound. Diphosphomevalonate decarboxylase is classified with the EC number EC 4.1.1.33. A diphosphomevalonate decarboxylase is naturally able to catalyze the decarboxylation of mevalonate diphosphate. In this reaction ATP and 5-diphosphomevalonate are converted into ADP, phosphate, isopentenyl diphosphate and $CO_2$. The reaction catalyzed by a diphosphomevalonate decarboxylase is shown in FIG. 1A. The activity of a diphosphomevalonate decarboxylase can be measured according to methods known in the art, e.g. in Reardon et al. (Biochemistry 26 (1987), 4717-4722). Preferably, the activity is measured by the spectrophotometric assay as described in Cardemil and Jabalquinto (Methods Enzymol. 110 (1985), 86-92). In this case, the reaction mixture (1 ml final volume) contains 0.1 M Tris-HCl buffer, pH 7.0, 0.1 M KCl, 5 mM ATP, 6 mM $MgCl_2$, 0.5 mM phosphoenolpyruvate, 0.23 mM NADH, 6.5 units of pyruvate kinase, 11.8 units of lactate dehydrogenase, mevalonate 5-diphosphate decarboxylase, and 0.15 mM mevalonate 5-pyrophosphate is added to start the reaction. The assay is performed at 30° C. in a thermostatted spectrophotometer.

It has been reported that at least in some cases the reaction catalyzed by diphosphomevalonate decarboxylase is divalent cation-dependent (see, e.g., Krepkiy et al., Protein Science 13 (2004), 1875-1881; Michihara et al., Biol. Pharm. Bull. 25 (2002), 302-306).

Diphosphomevalonate decarboxylase is an enzyme which, in its natural function, is part of the mevalonate pathway for isoprenoid synthesis in bacteria and of the sterol biosynthesis pathway in eukaryotes. It has been identified and isolated from various organisms such as animals, fungi, yeasts and bacteria. It is also expressed by certain plants.

The three-dimensional structure of several diphosphomevalonate decarboxylases has already been determined (see, e.g., Byres et al. (J. Mol. Biol. 371 (2007), 540-553); Bonanno et al. (Proc. Natl Acad. Sci. USA 98 (2001), 12896-12901); Voynova et al., Archives of Biochemistry and Biophysics 480 (2008), 58-67)) and considerable knowledge is available about its active site, amino acid residues crucial for the catalytic reaction and the actual enzymatic reaction (see, e.g. Byres et al. (J. Mol. Biol. 371 (2007), 540-553); Bonanno et al. (Proc. Natl Acad. Sci. USA 98 (2001), 12896-12901)). In most cases the enzyme is composed of about 300 to 400 amino acids and uses ATP as co-substrate which is converted during the decarboxylation reaction into ADP and inorganic phosphate.

Diphosphomevalonate decarboxylases have been described for various organisms and also amino acid and nucleotide sequences encoding them are available for numerous sources.

In principle any diphosphomevalonate decarboxylase can be used in the context of the present invention, in particular from prokaryotic or eukaryotic organisms. Eukaryotic diphosphomevalonate decarboxylases are described, for example, for animals such as Rattus norvegicus, Gallus gallus, Homo sapiens, Mus musculus, Sus scrofa, D. melanogaster, C. elegans and Trypanosoma brucei, for plants such as Arabidopsis thaliana, Ginko biloba, Oryza sativa, Pisum sativum, for yeasts, such as Saccharomyces cerevisiae and Candida albicans. Also numerous prokaryotic diphosphomevalonate decarboxylases have been described, e.g. for Helicobacter, Staphylococcus aureus, Streptococcus pneumoniae, Enterococcus faecium, Listeria monocytgenes, Leuconostoc citreum, Lactobacillus reuteri, to name just some. Table 1 provides a list of sequences of diphosphomevalonate decarboxylases from different organisms indicating the accession numbers under which they can be retrieved from the respective databases.

TABLE 1

| Organism | Uniprot Accession number |
|---|---|
| Bombyx mori | A5A7A2 |
| Saccharomyces cerevisiae strain YJM7 | A6ZSB7 |
| Solanum lycopersicum | A8WBX7 |
| Hevea brasiliensis | A9ZN03 |
| Nicotiana langsdorffii × Nicotiana sanderae | B3F8H5 |
| Saccharomyces cerevisiae (strain RM11-1a) | B3LPK0 |
| Phaeodactylum tricornutum CCAP 1055 | B7S422 |
| Candida dubliniensis | B9W6G7 |
| Pichia pastoris | C4QX63 |
| Ashbya gossypii | Q751D8 |
| Bos taurus | Q0P570 |
| Danio rerio | Q5U403 |
| Debaryomyces hanseni | Q6BY07 |
| Dictyostelium discoideum | Q54YQ9 |
| Homo sapiens | P53602 |
| Mus musculus | Q99JF5 |
| Rattus norvegicus | Q62967 |
| Schizosaccharomyces pombe | O13963 |
| Saccharomyces cerevisiae | P32377 |
| Arnebia euchroma | Q09RL4 |
| Aspergillus oryzae | Q2UGF4 |
| Mus musculus | Q3UYC1 |
| Ginkgo biloba | Q5UCT8 |
| Rattus norvegicus | Q642E5 |
| Oryza sativa subsp. japonica | Q6ETS8 |
| Arabidopsis thaliana | Q8LB37 |
| Encephalitozoon cuniculi | Q8SRR7 |
| Hevea brasiliensis | Q944G0 |

The sequences mentioned in Table 1 are those available in UniProt Release 2011_12 (from uniprot.org/downloads).

Examples of diphosphomevalonate decarboxylases from different organisms are given in SEQ ID NO: 1 to 19 and 22 to 29. In a preferred embodiment of the present invention the diphosphomevalonate decarboxylase is an enzyme comprising an amino acid sequence selected from the group consisting of SEQ ID NO: 1 to 19 and 22 to 29 or a sequence which is at least n % identical to any of SEQ ID NO: 1 to 19 or 22 to 29 and having the activity of a diphosphomevalonate decarboxylase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. Particularly preferred are sequences from bacteria of the genus Thermoplasma, Picrophilus, Ferroplasma or Streptococcus, and most preferred are sequences of the species

*Thermoplasma acidophilum* (see, e.g., SEQ ID NO: 18), *Thermoplasma volcanicum* (see, e.g., SEQ ID NO: 17), *Picrophilus torridus* (e.g. strain DSM 9790; see, for example, SEQ ID NOs: 6, 16, 20 and 21), *Ferroplasma acidarmanus* (e.g. *F. acidarmanus* fer1; see, for example, SEQ ID NO: 19), *Streptococcus mitis* (e.g. strain B6; see, for example, SEQ ID NO: 24), *Streptococcus infantarius* (e.g. *S. infantarius* subsp *infantarius* ATCC BA-201; see, for example, SEQ ID NO:23), *S. gallolyticus* (see, e.g., SEQ ID NO:25), *Streptococcus* sp. M134 (see, e.g., SEQ ID NO: 27), *S. salivarius* (e.g. SK126; see, for example, SEQ ID NO:29), *S. suis* (e.g. *S. suis* 89/1591; see, for example, SEQ ID NO: 28), *S. sanguinis* (e.g., SK36; see, for example, SEQ ID NO: 26) or *S. gordonii* (see, e.g., SEQ ID NO:12).

Preferably, the degree of identity is determined by comparing the respective sequence with the amino acid sequence of any one of the above-mentioned SEQ ID NOs. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of identity is calculated over the complete length of the sequence.

Moreover, if the term "homology" is used in the context of the present invention, this term preferably means "sequence identity".

In a preferred embodiment the decarboxylase employed in the method according to the invention is a diphosphomevalonate decarboxylase from *Picrophilus torridus* or an organism which is evolutionary closely related to *Picrophilus torridus*. In a further preferred embodiment the decarboxylase originates from an organism of the genus *Picrophilus, Thermoplasma* or *Ferroplasma*, more preferably of the species *Picrophilus torridus, Picrophilus oshimae, Thermoplasma volcanicum, Thermoplasma acidophilum, Ferroplasma acidarmanus* or *Ferroplasma cupricumulans*. In another embodiment the decarboxylase originates from an organism of the genus *Streptococcus*, preferably of the species *Streptococcus mitis, Streptococcus infantarius, S. gallolyticus, Streptococcus* sp. M134, *S. salivarius, S. suis, S. sanguinis* or *S. gordonii*.

Particularly preferred are decarboxylases from *Thermoplasma acidophilum* and from *Streptococcus mitis*.

In a particularly preferred embodiment the decarboxylase employed in the method according to the invention is a diphosphomevalonate decarboxylase which comprises the amino acid sequence as depicted in SEQ ID NO: 6, 16, 17, 18 or 19 or which comprises an amino acid sequence which is at least n % identical to any of SEQ ID NO: 6, 16, 17, 18 or 19 and which has the activity of a diphosphomevalonate decarboxylase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. The enzyme showing the amino acid sequence as shown in SEQ ID NOs:6 and 16 originates from *Picrophilus torridus*. Further preferred decarboxylases to be employed in the method according to the present invention are diphosphomevalonate decarboxylases which originate from organisms which are phylogenetically closely related to *Picrophilus torridus*, such as other bacteria of the genus *Picrophilus*, such as *Picrophilus oshimae*, bacteria of the genus *Ferroplasma*, e.g. *Ferroplasma acidarmanus* (SEQ ID NO:19), or of the genus *Thermoplasma*, such as *Thermoplasma acidophilum* (SEQ ID NO:18) and *Thermoplasma volcanium* (SEQ ID NO:17). The diphosphomevalonate decarboxylase of *Thermoplasma acidophilum* (AC number Q9HIN1) shows a homology of 38% to SEQ ID NO:6 and that of *Thermoplasma volcanium* (AC number Q97BY2) shows a homology of about 42% to SEQ ID NO:6.

The sequence shown in SEQ ID NO: 18 represents an enzyme identified in *Thermoplasma acidophilum*. In Genbank this enzyme is classified as a mevalonate diphosphate decarboxylase. However, it is known from Chen and Poulter (Biochemistry 49 (2010), 207-217) that in *Th. acidophilum* there exists an alternative mevalonate pathway which involves the action of a mevalonate-5-monophosphate decarboxylase. Thus, it is possible that the enzyme represented by SEQ ID NO: 18 actually represents a mevalonate-5-monophosphate decarboxylase.

The same may hold true for other archae bacteria. Therefore, in another preferred embodiment the decarboxylase employed in method according to the present invention is a mevalonate-5-monophosphate decarboxylase. Such an enzyme is capable of converting mevalonate-5-monophosphate into isopentenyl monophosphate. This activity can be measured in the same manner as the activity of a mevalonate diphosphate decarboxylase described above with the exception that mevalonate-5-monophosphate is used as a substrate.

In a further particularly preferred embodiment the decarboxylase employed in the method according to the invention is a diphosphomevalonate decarboxylase which is encoded by a nucleotide sequence as shown in SEQ ID NO: 20 or 21 or by a nucleotide sequence which is at least n % identical to any of SEQ ID NO: 20 or 21 and which encodes an enzyme having the activity of a diphosphomevalonate decarboxylase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 20 is the native nucleotide sequence encoding the MDP decarboxylase from *P. torridus* including at the N-terminus a His-tag. SEQ ID NO: 21 is a codon optimized sequence coding for the MDP decarboxylase from *P. torridus* including at the N-terminus a His-tag.

The decarboxylase, preferably diphosphomevalonate decarboxylase or mevalonate-5-monophosphate decarboxylase, employed in the process according to the invention can be a naturally occurring decarboxylase or it can be a decarboxylase which is derived from a naturally occurring decarboxylase, e.g. by the introduction of mutations or other alterations which, e.g., alter or improve the enzymatic activity, the stability, etc.

The term "decarboxylase", "diphosphomevalonate decarboxylase", "mevalonate-5-monophosphate decarboxylase", "a protein/enzyme having the activity of a decarboxylase" or "a protein/enzyme having the activity of a diphosphomevalonate decarboxylase" in the context of the present application also covers enzymes which are derived from a decarboxylase, preferably a diphosphomevalonate decarboxylase or a mevalonate-5-monophosphate decarboxylase, which are capable of catalyzing the decarboxylation of a 3-hydroxyalk-4-enoate but which only have a low affinity to their natural substrate, e.g. mevalonate diphosphate or a mevalonate-5-monophosphate, or do no longer accept their natural substrate. Such a modification of the preferred substrate allows to improve the conversion of a 3-hydroxyalk-4-enoate into a 1,3-diene compound and to reduce the production of the possibly occurring by-product isoprenyl pyrophosphate. Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution", DNA shuffling or in vivo evolution.

For example, for genetic engineering in prokaryotic cells, a nucleic acid molecule encoding a decarboxylase can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting decarboxylase variants are then tested for their enzymatic activity and in particular for their capacity to prefer a 3-hydroxy-4-enoate as a substrate rather than, e.g. mevalonate diphosphate or a mevalonate-5-monophosphate.

Such methods for identifying variants with improved enzymatic properties as regards the production of a 1,3-diene compound may also be carried out in the presence of a cofactor which allows for a steric and/or electronic complementation in the catalytic site of the enzyme due to the fact that the a 3-hydroxyalk-4-enoate substrate may be shorter than the natural substrate, e.g. mevalonate diphosphate in the case of diphosphomevalonate decarboxylase. Examples for such a cofactor would be phosphono-phosphate or phosphonamido-phosphate or orthophosphate.

The modified version of the decarboxylase accepting or preferring a 3-hydroxyalk-4-enoate as a substrate but having a low affinity to its natural substrate or no longer accepting its natural substrate may be derived from a naturally occurring decarboxylase or from an already modified, optimized or synthetically synthesized decarboxylase.

It is known that the conversion of mevalonate diphosphate into an isopentenyl diphosphate by a mevalonate diphosphate (MDP) decarboxylase (E.C. 4.1.1.33) takes place by the conversion of MDP into the corresponding 3-phosphonoxy compound which is then decarboxylated to lead to isopentenyl diphosphate. The reaction carried out by MDP decarboxylase using MDP as a substrate is depicted in FIG. 1A.

FIG. 1 B shows a scheme showing the conversion of a 3-hydroxyalk-4-enoate into a 1,3-diene compound using a mevalonate diphosphate decarboxylase. The intermediate in this case is a 3-phosphonoxyalk-4-enoate. FIG. 2 shows the conversion of 3-hydroxypent-4-enoate into 1,3-butadiene using a mevalonate diphosphate decarboxylase. The intermediate in this case is 3-phosphonoxypent-4-enoate. FIG. 3 shows the conversion of 3-hydroxy-4-methylpent-4-enoate and 3-hydroxy-4-methylpent-4-enoate into isoprene using a mevalonate diphosphate decarboxylase. The intermediate in this case is 3-phosphonoxy-4-methylpent-4-enoate or 3-phosphonoxy-3-methylpent-4-enoate, respectively.

It has been found that different decarboxylases, in particular mevalonate diphosphate decarboxylases, catalyze the two above mentioned steps with different efficiencies, i.e. that some decarboxylases catalyze the first step with a higher efficiency than other decarboxylases and that some decarboxylases show a preference for the second step, i.e. the decarboxylation step, and that therefore the efficiency of the whole reaction can be significantly increased by combining corresponding enzymes.

Thus, in another embodiment, the method according to the invention is characterized in that two types of enzymes are combined in order to increase the efficiency of the production rate. More specifically, the present invention relates to a method for producing a 1,3-diene compound, characterized in that it comprises the conversion of a 3-hydroxyalk-4-enoate into said 1,3-diene compound by
(i) a first enzyme having an activity of converting the 3-hydroxyalk-4-enoate into the corresponding 3-phosphonoxyalk-4-enoate; and
(ii) a second enzyme being different from the first enzyme and having an activity of converting said 3-phosphonoxyalk-4-enoate into said 1,3-diene compound by a decarboxylation reaction.

The term "3-hydroxyalk-4-enoate", as used herein, refers to a compound as defined herein-above.

The term "3-phosphonoxyalk-4-enoate" denotes a molecule which responds to the following general formula:

The term "3-phosphonoxyalk-4-enoate" denotes a molecule which responds to the following general formula:

$C_{n+1}H_{2n+1}O_6P$, with $3<n<7$, and comprising 3-phosphonoxypent-4-enoate as common motif (FIG. 1B) and optionally a methyl substitution on carbon 3 and carbon 4.

In preferred embodiment, "3-phosphonoxyalk-4-enoate", as used herein, denotes a molecule responding to the following structural formula:

HO—CO—CH$_2$—C(R$_1$)(O—PO$_3$H$_2$)—C(R$_2$)=CH$_2$
or O$^-$—CO—CH$_2$—C(R$_1$)(O—PO$_3$H$_2$)—C(R$_2$)=CH$_2$, wherein R$_1$ and R$_2$ are selected, independently, from the group consisting of a hydrogen atom and a methyl group.

A 3-phosphonoxyalk-4-enoate corresponds to the phosphate ester of the alcohol group in 3-hydroxyalk-4-enoate, as previously described. This phosphate group can be fully protonated or bear one or two negative charges as in the formulas:

HO—CO—CH$_2$—C(R$_1$)(O—PO$_3$H$_2$)—C(R$_2$)=CH$_2$

HO—CO—CH$_2$—C(R$_1$)(O—PO$_3$H$^-$)—C(R$_2$)=CH$_2$

HO—CO—CH$_2$—C(R$_1$)(O—PO$_3^{2-}$)—C(R$_2$)=CH$_2$

O$^-$—CO—CH$_2$—C(R$_1$)(O—PO$_3$H$_2$)—C(R$_2$)=CH$_2$

O$^-$—CO—CH$_2$—C(R$_1$)(O—PO$_3$H$^-$)—C(R$_2$)=CH$_2$

O$^-$—CO—CH$_2$—C(R$_1$)(O—PO$_3^{2-}$)—C(R$_2$)=CH$_2$

Carbon 3 is a chiral (stereogenic) center. The present definition encompasses the two chiral forms, even if one of the two forms, for example the R form, is the main form produced naturally. The suffix "oate", as used herein, can interchangeably denote either the carboxylate ion (COO—) or carboxylic acid (COOH). It is not used to denote an ester.

The term "1,3-diene", as used herein, refers to a compound as defined herein-above.

The term "an enzyme having an activity of converting the 3-hydroxyalk-4-enoate into the corresponding 3-phosphonoxyalk-4-enoate" means an enzyme which can phosphorylate a 3-hydroxyalk-4-enoate into the corresponding 3-phosphonoxyalk-4-enoate. The phosphate group comes preferably from an ATP molecule.

This activity can, e.g., be measured as described in the attached Examples, in particular Examples 2, 3, 7 and 8. One possibility is, for example, to incubate the respective enzyme with the 3-hydroxyalk-4-enoate and ATP and to measure the production of ADP (which reflects the production of the corresponding 3-phosphonoxyalk-4-enoate). Assays for measuring the production of ADP are known to the person skilled in the art. One of these methods is the well known pyruvate kinase/lactate dehydrogenase assay. In this case the assay measures the rate of NADH absorbance decrease at 340 nm which is proportional to the ADP quantity. In a preferred embodiment the term "an enzyme having an activity of converting the 3-hydroxyalk-4-enoate into the corresponding 3-phosphonoxyalk-4-enoate" means an enzyme which can convert 3-hydroxypent-4-enoate and ATP into 3-phosphonoxypent-4-enoate and ADP or an enzyme which can convert 3-hydroxy-4-methylpent-4-enoate or 3-hydroxy-4-methylpent-4-enoate and ATP into 3-phosphonoxy-4-methylpent-4-enoate or 3-phosphonoxy-3-methylpent-4-enoate, respectively, and ADP. Even more preferably such an enzyme can catalyze the reaction of converting the 3-hydroxyalk-4-enoate into the corresponding 3-phosphonoxyalk-4-enoate with a $K_M$ of 10 mM or lower, e.g. with a $K_M$ of 5 mM or lower, preferably of 1 mM or lower and even more preferably of 0.1 mM or lower. In a particularly preferred embodiment such an enzyme can catalyze the reaction of converting the 3-hydroxyalk-4-enoate into the corresponding 3-phosphonoxyalk-4-enoate with a $k_{cat}$ of at least 0.05 $s^{-1}$, preferably with a $k_{cat}$ of at least 0.09 $s^{-1}$, particularly preferred with a $k_{cat}$ of at least 0.1 $s^{-1}$, more preferred of at least 0.2 $s^{-1}$ and even more preferred with a $k_{cat}$ of at least 1.0 $s^{-1}$.

In a particularly preferred embodiment the capacity to convert a 3-hydroxyalk-4-enoate into the corresponding 3-phosphonoxyalk-4-enoate, e.g. 3-hydroxypent-4-enoate and ATP into 3-phosphonoxyalk-4-enoate and ADP, is measured in an assay as described in Examples 2, 3, 7 or 8.

The term "an enzyme having an activity of converting said 3-phosphonoxyalk-4-enoate into said 1,3-diene compound by a decarboxylation reaction" means an enzyme which can catalyze a reaction by which there is a decarboxylation and dephosporylation of the 3-phosphonoxyalk-4-enoate thereby leading to the corresponding 1,3-diene compound.

This activity can, e.g., be measured as described in the appended Examples, in particular in Examples 6 and 11. One possibility is thus to incubate the respective enzyme with the corresponding 3-phosphonoxyalk-4-enoate under conditions which in principle allow the decarboxylation and the dephosphorylation and to detect the production of the corresponding 1,3-diene compound, e.g. by gas chromatography. In a preferred embodiment the term "an enzyme having an activity of converting said 3-phosphonoxyalk-4-enoate into said 1,3-diene compound" means an enzyme which can convert 3-phosphonoxypent-4-enoate into 1,3-butadiene or an enzyme which can convert 3-phosphonoxy-4-methylpent-4-enoate or 3-phosphonoxy-3-methylpent-4-enoate into isoprene, preferably under the conditions described in Example 6 in which 3-phosphonoxy-4-methylpent-4-enoate or 3-phosphonoxy-3-methylpent-4-enoate is used instead of 3-phosphonoxypent-4-enoate in case of the synthesis of isoprene. Even more preferably such an enzyme can catalyze the reaction of converting the 3-phosphonoxyalk-4-enoate into the corresponding 1,3-diene compound (via decarboxylation and dephosphorylation) with a $K_M$ of 100 mM or lower, e.g. with a $K_M$ of 75 mM or lower, or with a $K_M$ of 50 mM or lower, preferably of 10 mM or lower or 5 mM or lower or 1 mM or lower, and even more preferably of 0.1 mM or lower. In a particularly preferred embodiment such an enzyme can catalyze the reaction of converting the 3-phosphonoxyalk-4-enoate into the corresponding 1,3-diene compound with a $k_{cat}$ of at least $10^{-6}$ $s^{-1}$, preferably with a $k_{cat}$ of at least $10^{-4}$ $s^{-1}$, e.g. with a $k_{cat}$ of at least $10^{-3}$ $s^{-1}$ or with a $k_{cat}$ of at least $10^{-2}$ $s^{-1}$, such as with a $k_{cat}$ of at least $10^{-1}$ $s^{-1}$, for example with a $k_{cat}$ of at least 0.2 $s^{-1}$, preferably with a $k_{cat}$ of at least 0.5 $s^{-1}$, particularly preferred with a $k_{cat}$ of at least 1.0 $s^{-1}$, more preferred of at least 2.0 $s^{-1}$ and even more preferred with a $k_{cat}$ of at least 5.0 $s^{-1}$. In a particularly preferred embodiment the capacity to convert a 3-phosphonoxyalk-4-enoate into a 1,3-diene compound is measured in an assay as described in Example 6 or in Example 11.

In one preferred embodiment an enzyme mentioned in (i) and (ii), above, is an enzyme which is considered by NCBI or an equivalent engine as having a COG3407 domain.

In a preferred embodiment of the method according to the invention the first enzyme (i) having an activity of converting the 3-hydroxyalk-4-enoate into the corresponding 3-phosphonoxyalk-4-enoate is selected from the group consisting of (A) a protein comprising the amino acid sequence as shown in SEQ ID NO: 16 or a protein comprising an amino acid sequence which is at least 15% identical to the amino acid sequence shown in SEQ ID NO: 16 and showing an activity of converting the 3-hydroxyalk-4-enoate into the corresponding 3-phosphonoxyalk-4-enoate which is at least as high as the corresponding activity of the protein having the amino acid sequence shown in SEQ ID NO: 16;

(B) a protein comprising the amino acid sequence as shown in SEQ ID NO: 17 or a protein comprising an amino acid sequence which is at least 15% identical to the amino acid sequence shown in SEQ ID NO: 17 and showing an activity of converting the 3-hydroxyalk-4-enoate into the corresponding 3-phosphonoxyalk-4-enoate which is at least as high as the corresponding activity of the protein having the amino acid sequence shown in SEQ ID NO: 17;

(C) a protein comprising the amino acid sequence as shown in SEQ ID NO: 18 or a protein comprising an amino acid sequence which is at least 15% identical to the amino acid sequence shown in SEQ ID NO: 18 and showing an activity of converting the 3-hydroxyalk-4-enoate into the corresponding 3-phosphonoxyalk-4-enoate which is at least as high as the corresponding activity of the protein having the amino acid sequence shown in SEQ ID NO: 18; and (D) a protein comprising the amino acid sequence as shown in SEQ ID NO: 19 or a protein comprising an amino acid sequence which is at least 15% identical to the amino acid sequence shown in SEQ ID NO: 19 and showing an activity of converting the 3-hydroxyalk-4-enoate into the corresponding 3-phosphonoxyalk-4-enoate which is at least as high as the corresponding activity of the protein having the amino acid sequence shown in SEQ ID NO: 19.

SEQ ID NO: 16 shows the amino acid sequence of an enzyme from *Picrophilus torridus* DSM 9790 (GenBank accession number AAT43941; Swissprot/TrEMBL accession number Q6KZB1).

SEQ ID NO: 17 shows the amino acid sequence of an enzyme from *Thermoplasma* volcanium (GenBank accession number BAB59465; Swissprot/TrEMBL accession number Q97BY2).

SEQ ID NO: 18 shows the amino acid sequence of an enzyme from *Thermoplasma acidophilum* (GenBank accession number CAC12426; Swissprot/TrEMBL accession number Q9HIN1).

SEQ ID NO: 19 shows the amino acid sequence of an enzyme from *Ferroplasma acidarmanus* fer1 (GenBank accession number ZP_05571615).

In a further preferred embodiment of the method according to the invention the second enzyme (ii) having an activity of converting said 3-phosphonoxyalk-4-enoate into said 1,3-diene compound is selected from the group consisting of (a) a protein comprising the amino acid sequence as shown in SEQ ID NO: 12 or a protein comprising an amino acid sequence which is at least 15% identical to the amino acid sequence shown in SEQ ID NO: 12 and showing an activity of converting said 3-phosphonoxyalk-4-enoate into said 1,3-diene compound which is at least as high as the corresponding activity of the protein having the amino acid sequence shown in SEQ ID NO: 12;

(b) a protein comprising the amino acid sequence as shown in SEQ ID NO: 22 or a protein comprising an amino acid sequence which is at least 15% identical to the amino acid sequence shown in SEQ ID NO: 22 and showing an activity of converting said 3-phosphonoxyalk-4-enoate into said 1,3-diene compound which is at least as high as the corresponding activity of the protein having the amino acid sequence shown in SEQ ID NO: 22;

(c) a protein comprising the amino acid sequence as shown in SEQ ID NO: 23 or a protein comprising an amino acid sequence which is at least 15% identical to the amino acid sequence shown in SEQ ID NO: 23 and showing an activity of converting said 3-phosphonoxyalk-4-enoate into said 1,3-diene compound which is at least as high as the corresponding activity of the protein having the amino acid sequence shown in SEQ ID NO: 23;

(d) a protein comprising the amino acid sequence as shown in SEQ ID NO: 1 or a protein comprising an amino acid sequence which is at least 15% identical to the amino acid sequence shown in SEQ ID NO: 1 and showing an activity of converting said 3-phosphonoxyalk-4-enoate into said 1,3-diene compound which is at least as high as the corresponding activity of the protein having the amino acid sequence shown in SEQ ID NO: 1;

(e) a protein comprising the amino acid sequence as shown in SEQ ID NO: 7 or a protein comprising an amino acid sequence which is at least 15% identical to the amino acid sequence shown in SEQ ID NO: 7 and showing an activity of converting said 3-phosphonoxyalk-4-enoate into said 1,3-diene compound which is at least as high as the corresponding activity of the protein having the amino acid sequence shown in SEQ ID NO: 7;

(f) a protein comprising the amino acid sequence as shown in SEQ ID NO: 24 or a protein comprising an amino acid sequence which is at least 15% identical to the amino acid sequence shown in SEQ ID NO: 24 and showing an activity of converting said 3-phosphonoxyalk-4-enoate into said 1,3-diene compound which is at least as high as the corresponding activity of the protein having the amino acid sequence shown in SEQ ID NO: 24;

(g) a protein comprising the amino acid sequence as shown in SEQ ID NO: 25 or a protein comprising an amino acid sequence which is at least 15% identical to the amino acid sequence shown in SEQ ID NO: 25 and showing an activity of converting said 3-phosphonoxyalk-4-enoate into said 1,3-diene compound which is at least as high as the corresponding activity of the protein having the amino acid sequence shown in SEQ ID NO: 25;

(h) a protein comprising the amino acid sequence as shown in SEQ ID NO: 26 or a protein comprising an amino acid sequence which is at least 15% identical to the amino acid sequence shown in SEQ ID NO: 26 and showing an activity of converting said 3-phosphonoxyalk-4-enoate into said 1,3-diene compound which is at least as high as the corresponding activity of the protein having the amino acid sequence shown in SEQ ID NO: 26;

(i) a protein comprising the amino acid sequence as shown in SEQ ID NO: 27 or a protein comprising an amino acid sequence which is at least 15% identical to the amino acid sequence shown in SEQ ID NO: 27 and showing an activity of converting said 3-phosphonoxyalk-4-enoate into said 1,3-diene compound which is at least as high as the corresponding activity of the protein having the amino acid sequence shown in SEQ ID NO: 27;

(j) a protein comprising the amino acid sequence as shown in SEQ ID NO: 28 or a protein comprising an amino acid sequence which is at least 15% identical to the amino acid sequence shown in SEQ ID NO: 28 and showing an activity of converting said 3-phosphonoxyalk-4-enoate into said 1,3-diene compound which is at least as high as the corresponding activity of the protein having the amino acid sequence shown in SEQ ID NO: 28; and (k) a protein comprising the amino acid sequence as shown in SEQ ID NO: 29 or a protein comprising an amino acid sequence which is at least 15% identical to the amino acid sequence shown in SEQ ID NO: 29 and showing an activity of converting said 3-phosphonoxyalk-4-enoate into said 1,3-diene compound which is at least as high as the corresponding activity of the protein having the amino acid sequence shown in SEQ ID NO: 29.

SEQ ID NO: 12 shows the amino acid sequence of an enzyme cloned from *Streptococcus gordonii*. SEQ ID NO: 22 shows the amino acid sequence of an enzyme from *Streptococcus gordonii* str. Challis substr. CH1 (GenBank accession number AAT43941; Swissprot/TrEMBL accession number A8UU9). SEQ ID NO: 23 shows the amino acid sequence of an enzyme from *Streptococcus* infantarius subsp infantarius ATCC BAA-102 (GenBank accession number EDT48420.1; Swissprot/TrEMBL accession number B1SCG0). SEQ ID NO: 1 shows the amino acid sequence of an enzyme from *Homo sapiens* (GenBank accession number AAC50440.1; Swissprot/TrEMBL accession number P53602.1). SEQ ID NO: 7 shows the amino acid sequence of an enzyme from *Lactobacillus delbrueckii* (GenBank accession number CAI97800.1; Swissprot/TrEMBL accession number Q1GAB2). SEQ ID NO: 24 shows the amino acid sequence of an enzyme from *Streptococcus mitis* (strain B6) (GenBank accession number CBJ22986.1). SEQ ID NO: 25 shows the amino acid sequence of an enzyme from *Streptococcus gallolyticus* UCN34 (GenBank accession number CBI13757.1). SEQ ID NO: 26 shows the amino acid sequence of an enzyme from *Streptococcus sanguinis* SK36 (GenBank accession number ABN43791.1). SEQ ID NO: 27 shows the amino acid sequence of an enzyme from *Streptococcus* sp. M143 (GenBank accession number EFA24040.1). SEQ ID NO: 28 shows the amino acid sequence of an enzyme from *Streptococcus suis* 89/1591 (GenBank accession number EEF63672.1). SEQ ID NO: 29 shows the amino acid sequence of an enzyme from *Streptococcus salivarius* SK126 (GenBank accession number EEK09252).

In a preferred embodiment of the method according to the invention the first enzyme (i) is as defined in (A) above and the second enzyme (ii) is as defined in (a) or (b) mentioned above, even more preferably the second enzyme is as defined in (f), (g), (h), (i), (j) or (k) mentioned above.

In another preferred embodiment of the method according to the invention the second enzyme (ii) having an activity of converting said 3-phosphonoxyalk-4-enoate into said 1,3-diene compound is selected from any one of the proteins listed in the following Table or from a protein comprising an amino acid sequence which is at least 15% identical to the amino acid sequence of such a protein and showing an activity of converting said 3-phosphonoxyalk-4-enoate into said 1,3-diene compound which is at least as high as the corresponding activity of said protein.

TABLE 2

| Organism | Ref sequence GenBank |
| --- | --- |
| *Methanosarcina mazei* | AAM31457.1 |
| *Methanocaldococcus jannaschii* | AAB98390.1 |
| *Staphylococcus saprophyticus* | BAE19266.1 |
| *Streptococcus agalactiae* | EAO73731.1 |
| *Enterococcus faecalis* | AAO80711.1 |
| *Flavobacterium johnsoniae* | ABQ04421.1 |
| *Bdellovibrio bacteriovorus* | CAE79505.1 |
| *Chloroflexus aurantiacus* | A9WEU8.1 |
| *Legionella pneumophila* | CAH13175.1 |
| *Listeria monocytogenes* | EAL09343.1 |
| *Metallosphaera sedula* | ABP95731.1 |
| *Staphylococcus epidermidis* | AAO03959.1 |
| *Streptococcus thermophilus* | AAV60266.1 |
| *Bacillus coagulans* | EAY45229.1 |
| *Chloroflexus aggregans* | EAV09355.1 |
| *Lactobacillus brevis* | ABJ64001.1 |
| *Lactobacillus fermentum* | BAG27529.1 |
| *Lactobacillus plantarum* | CAD64155.1 |
| *Lactobacillus salivarius* | ABD99494.1 |
| *Lactococcus lactis* sp. *lactis* | AAK04503.1 |
| *Dichelobacter nodosus* | ABQ14154.1 |
| *Flavobacterium psychrophilum* | CAL42423.1 |
| *Streptococcus pneumoniae* | EDT95457.1 |
| *Streptococcus pyogenes* | AAT86835.1 |
| *Streptococcus suis* | ABP91444.1 |
| *Staphylococcus haemolyticus* | BAE05710.1 |
| *Streptococcus equi* | ACG62435.1 |
| *Arabidopsis thaliana* | AAC67348.1 |
| *Borrelia afzelii* | ABH01961.1 |
| *Encephalitozoon cuniculi* | CAD25409.1 |
| *Streptomyces sp.* | BAB07791.1 |
| *Streptococcus agalactiae* | EAO73731.1 |
| *Streptococcus uberis* | CAR41735.1 |
| *Gallus gallus* | XP_423130 |
| *Salmo salmar* | ACI34234 |
| *Natromonas pharaonis* | CAI48881.1 |
| *Haloarcula marismortui* | AAV46412.1 |
| *Haloquadratum walsbyi* | CAJ51653.1 |

The sequences mentioned in Table 2 are those available in: Genetic Sequence Data Bank, Dec. 15, 2011, NCBI-GenBank Flat File Release 187.0, Distribution Release Notes 146413798 loci, 135117731375 bases, from 146413798 reported sequences (see ncbi.nih.gov/genbank/gbrel.txt).

As mentioned above, not only the proteins having the specifically mentioned amino acid sequences listed in the respective SEQ ID NOs or in Table 2 can be used, but also proteins which are considered by NCBI or an equivalent engine as having a COG3407 domain and, more preferred, proteins the amino acid sequence of which shows a homology of at least 15% to the specifically mentioned amino acid sequence and which have a respective enzymatic activity at least as high as the activity of a protein having the specifically mentioned amino acid sequence. Preferred enzymes advantageously have at least x % homology, wherein x is selected from the group consisting of 20, 25, 20, 35, 40, 45, 50, 55 and 60. In a further preferred embodiment the enzyme has at least 65% sequence homology, preferably at least 70%, more preferably at least 75%, even more preferably, at least 80, 85, 90, 95, 96, 97, 98 or 99% homology to one of the sequences shown in any one of SEQ ID NO: 1 to 19 and 22 to 29, in particular, SEQ ID NOs: 1, 7, 12, 16, 17, 18, 19, 22, 23, 24, 25, 26, 27, 28 or 29 or to one of the sequences shown in Table 1. The percent of sequence homology can be determined by different methods and by means of software programs known to one of skill in the art, such as for example the CLUSTAL method or BLAST and derived software, or by using a sequence comparison algorithm such as that described by Needleman and Wunsch (J. Mol. Biol., 1970, 48:443) or Smith and Waterman (J. Mol. Biol., 1981, 147:195).

Such proteins showing the indicated degree of homology can, e.g., be other enzymes which occur naturally or which have been prepared synthetically. They include in particular enzymes which can be selected for their ability to produce alkenes according to the invention. Thus, a selection test comprises contacting the purified enzyme, or a microorganism producing the enzyme, with the substrate of the reaction and measuring the production of the respective compound, i.e. the 3-phosphonoxyalk-4-enoate or the 1,3-diene compound. Such selection tests can also be used to screen for enzymes with an optimized enzymatic activity for the substrate to be converted into the 3-phosphonoxyalk-4-enoate or the 1,3-diene compound, i.e. having an optimized activity with respect to one or more 3-hydroxyalk-4-enoates or 3-phosphonoxyalk-4-enoates.

Such screening methods are well-known in the art and include, e.g. protein engineering techniques such as random mutagenesis, massive mutagenesis, site-directed mutagenesis, DNA shuffling, synthetic shuffling, in vivo evolution, or complete synthesis of genes and subsequent screening for the desired enzymatic activity.

The enzyme used in the invention can thus be natural or synthetic, and produced by chemical, biological or genetic means. It can also be chemically modified, for example in order to improve its activity, resistance, specificity, purification, or to immobilize it on a support.

Enzymes which are able to catalyze the above described reactions for converting a 3-hydroxyalk-4-enoate into a 1,3-diene compound via a 3-phosphonoxyalk-4-enoate are often enzymes which can be classified in the phylogenetic superfamily of mevalonate diphosphate (MDP) decarboxylases (enzyme nomenclature EC 4.1.1.33).

Accordingly, in a preferred embodiment, the enzyme defined in (i) or (ii) above, is a MDP decarboxylase. In the context of the present invention a MDP decarboxylase is defined as an enzyme which can at least catalyze the conversion of 5-diphospho-3-phosphomevalonate into isopentenyl-5-diphosphate and $CO_2$ or which can at least catalyze the reaction of converting mevalonate diphosphate and ATP into 5-diphospho-3-phosphomevalonate and ADP. Preferably, such an enzyme can catalyze both reactions.

In another preferred embodiment the enzyme defined in (i) above, is an enzyme as defined in (i) (C). The sequence shown in SEQ ID NO: 18 represents an enzyme identified in *Thermoplasma acidophilum*. In Genbank this enzyme is classified as a mevalonate diphosphate decarboxylase. However, it is known from Chen and Poulter (Biochemistry 49 (2010), 207-217) that in *Th. acidophilum* there exists an alternative mevalonate pathway which involves the action of a mevalonate-5-monophosphate decarboxylase. Thus, it is possible that the enzyme represented by SEQ ID NO: 18 actually represents a mevalonate-5-monophosphate decarboxylase. The same may hold true for other archae bacteria. Therefore, in another preferred embodiment the enzyme defined in (i) or (ii) above, is a mevalonate-5-monophosphate decarboxylase. Such an enzyme is capable of converting mevalonate-5-monophosphate into isopentenylmonophosphate.

In a further embodiment, the enzyme as defined in (ii) of any of the previously described embodiments is an enzyme which can be classified as a terpene synthase. The inventors were able to show that surprisingly a terpene synthase is able to catalyze the conversion of a 3-phosphonoxyalk-4-enoate into a 1,3-diene, in particular the conversion of 3-phosphonoxypent-4-enoate into 1,3-butadiene (see Example 11 and FIG. 8).

The terpene synthases constitute an enzyme family which comprises enzymes catalyzing the formation of numerous natural products always composed of carbon and hydrogen (terpenes) and sometimes also of oxygen or other elements (terpenoids). Terpenoids are structurally diverse and widely distributed molecules corresponding to well over 30000 defined natural compounds that have been identified from all kingdoms of life. In plants, the members of the terpene synthase family are responsible for the synthesis of the various terpene molecules from two isomeric 5-carbon precursor "building blocks", isoprenyl diphosphate and prenyl diphosphate, leading to 5-carbon isoprene, 10-carbon monoterpene, 15-carbon sesquiterpene and 20-carbon diterpenes" (Chen et al.; The Plant Journal 66 (2011), 212-229).

The ability of terpene synthases to convert a prenyl diphosphate containing substrate to diverse products during different reaction cycles is one of the most unique traits of this enzyme class. The common key step for the biosynthesis of all terpenes is the reaction of terpene synthase on corresponding diphosphate esters. The general mechanism of this enzyme class induces the removal of the diphosphate group and the generation of an intermediate with carbocation as the first step. In the various terpene synthases, such intermediates further rearrange to generate the high number of terpene skeletons observed in nature. In particular, the resulting cationic intermediate undergoes a series of cyclizations, hydride shifts or other rearrangements until the reaction is terminated by proton loss or the addition of a nucleophile, in particular water for forming terpenoid alcohols (Degenhardt et al., Phytochemistry 70 (2009), 1621-1637).

The terpene synthases show a common catalytic mechanism which involves the formation of an allylic carbocation by the removal of a pyrophosphate leaving group, which evolves then towards various products (see the following scheme; Croteau, Chem. Rev. 87 (1987), 929-954; Croteau, Topics Curr. Chem. 209 (2000).

The different terpene synthases also share various structural features. These include a highly conserved C-terminal domain, which contains their catalytic site and an aspartate-rich DDXXD motif essential for the divalent metal ion (typically Mg2+ or Mn2+) assisted substrate binding in these enzymes (Green et al. Journal of biological chemistry, 284, 13, 8661-8669). In principle, any known enzyme which can be classified as belonging to the EC 4.2.3 enzyme superfamily can be employed.

In one embodiment of the present invention an isoprene synthase (EC 4.2.3.27) is used for the direct enzymatic conversion of a 3-phosphonoxyalk-4-enoate into a 1,3-diene. Isoprene synthase is an enzyme which catalyzes the following reaction:

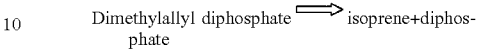

Dimethylallyl diphosphate ⇌ isoprene+diphosphate

This enzyme occurs in a number of organisms, in particular in plants and some bacteria. The occurrence of this enzyme has, e.g., been described for *Arabidopsis thaliana*, a number of *Populus* species like *P. alba* (UniProt accession numbers Q50L36, A9Q7C9, D8UY75 and D8UY76), *P. nigra* (UniProt accession number AOPFK2), *P. canescence* (UniProt accession number Q9AR86; see also Köksal et al., J. Mol. Biol. 402 (2010), 363-373), *P. tremuloides*, *P. trichocarpa*, in *Quercus petraea*, *Quercus robur*, *Salix discolour*, *Pueraria montana* (UniProt accession number Q6EJ97), *Pueraria montana* var. *lobata* (SEQ ID NO:30), *Mucuna pruriens*, *Vitis vinifera*, *Embryophyta* and *Bacillus subtilis*. In principle, any known isoprene synthase can be employed in the method according to the invention. In a preferred embodiment, the isoprene synthase employed in a method according to the present invention is an isoprene synthase from a plant of the genus *Populus*, more preferably from *Populus trichocarpa* or *Populus alba*. In another preferred embodiment the isoprene synthase employed in a method according to the present invention is an isoprene synthase from *Pueraria montana*, preferably from *Pueraria montana* var. *lobata* (UNIPROT: Q6EJ97), or from *Vitis vinifera*. Preferred isoprene synthases to be used in the context of the present invention are the isoprene synthase of *Populus alba* (Sasaki et al.; FEBS Letters 579 (2005), 2514-2518) or the isoprene synthases from *Populus trichocarpa* and *Populus tremuloides* which show very high sequence homology to the isoprene synthase from *Populus alba*. Another preferred isoprene synthase is the isoprene synthase from *Pueraria montana* var. *lobata* (kudzu) (Sharkey et al.; Plant Physiol. 137 (2005), 700-712; UNIPROT: Q6EJ97; SEQ ID NO:30).

In a preferred embodiment of the present invention the isoprene synthase is an enzyme comprising the amino acid sequence shown in SEQ ID NO: 30 or a sequence which is at least n % identical to SEQ ID NO: 30 and having the activity of an isoprene synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99.

The activity of an isoprene synthase can be measured according to methods known in the art, e.g. as described in Silver and Fall (Plant Physiol (1991) 97, 1588-1591). In a typical assay, the enzyme is incubated with dimethylallyl diphosphate in the presence of the required co-factors, $Mg^{2+}$ or $Mn^{2+}$ and $K^+$ in sealed vials. At appropriate time volatiles compound in the headspace are collected with a gas-tight syringe and analyzed for isoprene production by gas chromatography (GC).

Moreover, it is not only possible to use an isoprene synthase for converting a 3-phosphonoxyalk-4-enoate into a 1,3-diene according to the above shown scheme, but it is also possible to use other enzymes from the family of monoterpene synthases. Monoterpene synthases comprise a number of families to which specific EC numbers are allocated. However, they also include also a number of enzymes which are simply referred to as monoterpene synthases and which are not classified into a specific EC number. To the latter group belong, e.g., the monoterpene synthases of *Eucalyptus globulus* (UniProt accession number Q0PCI4) and of *Melaleuca alternifolia* described in Shelton et al. (Plant Physiol. Biochem. 42 (2004), 875-882). In particularly preferred embodiments of the present invention use is made of a monoterpene synthase of *Eucalyptus globulus* or of *Melaleuca alternifolia*.

In other preferred embodiments of the method according to the invention the conversion of a 3-phosphonoxyalk-4-enoate into a 1,3-diene according to the above shown scheme is achieved by a terpene synthase belonging to one of the following families: alpha-farnesene synthases (EC 4.2.3.46), beta-farnesene synthases (EC 4.2.3.47), myrcene/(E)-beta-ocimene synthases (EC 4.2.3.15) and pinene synthase (EC 4.2.3.14).

Farnesene synthases are generally classified into two different groups, i.e. alpha-farnesene synthases (EC 4.2.3.46) and beta farnesene synthases (EC 4.2.3.47). Alpha-farnesene synthases (EC 4.2.3.46) naturally catalyze the following reaction:

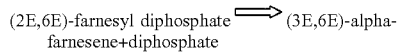
(2E,6E)-farnesyl diphosphate ⇌ (3E,6E)-alpha-farnesene+diphosphate

This enzyme occurs in a number of organisms, in particular in plants, for example in *Malus×domestica* (UniProt accession numbers Q84LB2, B2ZZ11, Q6Q2J2, Q6QWJ1 and Q32WI2), *Populus trichocarpa, Arabidopsis thaliana* (UniProt accession numbers A4FVP2 and P0CJ43), *Cucumis melo* (UniProt accession number B2KSJ5) and *Actinidia deliciosa* (UniProt accession number C7SHN9). In principle, any known alpha-farnesene synthase can be employed in the method according to the invention. In a preferred embodiment, the alpha-farnesene synthase employed in a method according to the present invention is an alpha-farnesene synthase from *Malus×domestica* (e.g. Seq ID NO:8), UniProt accession numbers Q84LB2, B2ZZ11, Q6Q2J2, Q6QWJ1 and Q32WI2; see also Green et al.; Photochemistry 68 (2007), 176-188).

Beta-farnesene synthases (EC 4.2.3.47) naturally catalyze the following reaction:

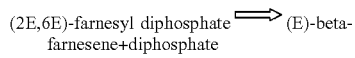
(2E,6E)-farnesyl diphosphate ⇌ (E)-beta-farnesene+diphosphate

This enzyme occurs in a number of organisms, in particular in plants and in bacteria, for example in *Artemisia annua* (UniProt accession number Q4VM12), *Citrus junos* (UniProt accession number Q94JS8), *Oryza sativa* (UniProt accession number Q0J7R9), *Pinus sylvestris* (UniProt accession number D7PCH9), *Zea diploperennis* (UniProt accession number C7E5V9), *Zea mays* (UniProt accession numbers Q2NM15, C7E5V8 and C7E5V7), *Zea perennis* (UniProt accession number C7E5W0) and *Streptococcus coelicolor* (Zhao et al., J. Biol. Chem. 284 (2009), 36711-36719). In principle, any known beta-farnesene synthase can be employed in the method according to the invention. In a preferred embodiment, the beta-farnesene synthase employed in a method according to the present invention is a beta-farnesene synthase from *Mentha piperita* (Crock et al.; Proc. Natl. Acad. Sci. USA 94 (1997), 12833-12838).

Methods for the determination of farnesene synthase activity are known in the art and are described, for example, in Green et al. (Phytochemistry 68 (2007), 176-188). In a typical assay farnesene synthase is added to an assay buffer containing 50 mM BisTrisPropane (BTP) (pH 7.5), 10% (v/v) glycerol, 5 mM DTT. Tritiated farnesyl diphosphate and metal ions are added. Assays containing the protein are overlaid with 0.5 ml pentane and incubated for 1 h at 30° C. with gentle shaking. Following addition of 20 mM EDTA (final concentration) to stop enzymatic activity an aliquot of the pentane is removed for scintillation analysis. The olefin products are also analyzed by GC-MS.

Myrcene/(E)-beta-ocimene synthases (EC 4.2.3.15) are enzymes which naturally catalyze the following reaction:

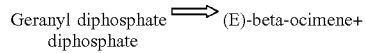
Geranyl diphosphate ⇌ (E)-beta-ocimene+diphosphate or

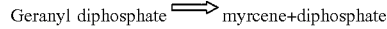
Geranyl diphosphate ⇌ myrcene+diphosphate

These enzymes occur in a number of organisms, in particular in plants and animals, for example in *Lotus japanicus* (Arimura et al.; Plant Physiol. 135 (2004), 1976-1983), *Phaseolus lunatus* (UniProt accession number B1P189), *Abies grandis, Arabidopsis thaliana* (UniProt accession number Q9ZUH4), *Actinidia chinensis, Vitis vinifera* (E5GAG5), *Perilla fructescens, Ochtodes secundiramea* and in *Ips pini* (UniProt accession number Q58GE8). In principle, any known myrcene/ocimene synthase can be employed in the method according to the invention. In a preferred embodiment, the myrcene/ocimene synthase employed in a method according to the present invention is an (E)-beta-ocimene synthase from *Vitis vinifera*.

The activity of an ocimene/myrcene synthase can be measured as described, for example, in Arimura et al. (Plant Physiology 135 (2004), 1976-1983). In a typical assay for determining the activity, the enzyme is placed in screw-capped glass test tube containing divalent metal ions, e.g. $Mg^{2+}$ and/or $Mn^{2+}$, and substrate, i.e. geranyl diphosphate. The aqueous layer is overlaid with pentane to trap volatile compounds. After incubation, the assay mixture is extracted with pentane a second time, both pentane fractions are pooled, concentrated and analyzed by gas chromatography to quantify ocimene/myrcene production.

Pinene synthase (EC 4.2.3.14) is an enzyme which naturally catalyzes the following reaction:

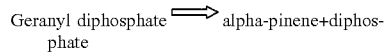
Geranyl diphosphate ⇌ alpha-pinene+diphosphate

This enzyme occurs in a number of organisms, in particular in plants, for example in *Abies grandis* (UniProt accession number O244475), *Artemisia annua, Chamaecyparis formosensis* (UniProt accession number C3RSF5), *Salvia officinalis* and *Picea sitchensis* (UniProt accession number Q6XDB5).

For the enzyme from *Abies grandis* a particular reaction was also observed (Schwab et al., Arch. Biochem. Biophys. 392 (2001), 123-136), namely the following:

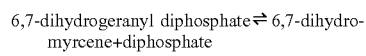
6,7-dihydrogeranyl diphosphate ⇌ 6,7-dihydromyrcene+diphosphate

In principle, any known pinene synthase can be employed in the method according to the invention. In a preferred embodiment, the pinene synthase employed in a method according to the present invention is a pinene synthase from *Abies grandis* (UniProt accession number O244475; Schwab et al., Arch. Biochem. Biophys. 392 (2001), 123-136).

Methods for the determination of pinene synthase activity are known in the art and are described, for example, in Schwab et al. (Archives of Biochemistry and Biophysics 392 (2001), 123-136). In a typical assay, the assay mixture for pinene synthase consists of 2 ml assay buffer (50 mM Tris/HCl, pH 7.5, 500 mM KCl, 1 mM MnCl2, 5 mM dithiothreitol, 0.05% NaHSO3, and 10% glycerol) containing 1 mg of the purified protein. The reaction is initiated in a Teflon-sealed screw-capped vial by the addition of 300 mM substrate. Following incubation at 25° C. for variable periods (0.5-24 h), the mixture is extracted with 1 ml of diethyl ether. The biphasic mixture is vigorously mixed and then centrifuged to separate the phases. The organic extract is dried (MgSO4) and subjected to GC-MS and MDGC analysis.

According to the present invention it is also possible to employ in the present invention an enzyme which has been constructed by physically combining an enzyme as defined in (i), above, which is particularly efficient in catalyzing the conversion of the 3-hydroxyalk-4-enoate into the corresponding 3-phosphonoxyalk-4-enoate, with an enzyme as defined in (ii), above, which is particularly efficient in catalyzing the conversion of said 3-phosphonoxyalk-4-enoate into said 1,3-diene compound by a decarboxylation reaction. This can be achieved, e.g., by fusing corresponding nucleic acids encoding the respective enzymes so as to produce a fusion protein or by mutating one enzyme so that it acquires a high efficiency for both catalytic activities.

The present invention also relates to the use of at least two enzymes, wherein one enzyme is selected from (i) as specified above and the other enzyme is selected from (ii) as specified above or of a microorganism producing said combination of enzymes, for producing a 1,3-diene compound from a 3-hydroxyalk-4-enoate.

The present invention also discloses organisms, preferably microorganisms, which produce at least two enzymes, wherein one enzyme is selected from (i) as specified above and the other enzyme is selected from (ii) as specified above.

The methods according to the invention can be carried out in vitro, in the presence of isolated enzymes (or enzyme systems additionally comprising one or more cofactors). In vitro preferably means in a cell-free system.

In one embodiment, the enzymes employed in the method are used in purified form to convert a 3-hydroxyalk-4-enoate or a 3-phosphonoxyalk-4-enoate to a 1,3-diene compound. However, such a method may be costly, since enzyme and substrate production and purification costs are high.

Thus, in another preferred embodiment, the enzymes employed in the method are present in the reaction as a non-purified extract, or else in the form of non-lysed bacteria, so as to economize on protein purification costs. However, the costs associated with such a method may still be quite high due to the costs of producing and purifying the substrates.

Accordingly, in one preferred embodiment, the enzymes, native or recombinant, purified or not, are used to convert a 3-hydroxyalk-4-enoate or a 3-phosphonoxyalk-4-enoate to a 1,3-diene compound. To do this, the enzymes are incubated in the presence of the substrate in physicochemical conditions allowing the enzymes to be active, and the incubation is allowed to proceed for a sufficient period of time. At the end of the incubation, one optionally measures the presence of the 1,3-diene compound by using any detection system known to one of skill in the art such as gas chromatography or colorimetric tests for measuring the formation of the 1,3-diene product, or of free phosphate, or else for measuring the disappearance of the 3-hydroxyalk-4-enoate substrate or of ATP or of the 3-phosphonoxyalk-4-enoate.

In a preferred embodiment, cofactors are added so as to best mimic the natural reaction or so as to provide steric or electronic complementation in the catalytic cleft. For example, if one of the enzymes used in the method according to the invention is an enzyme which naturally uses mevalonate disphosphate (MDP) as a substrate, the structure of 3-hydroxyalk-4-enoate leaves a large space in the catalytic cleft empty during enzyme-substrate binding since generally a 3-hydroxyalk-4-enoate corresponds to a fragment of MDP. Filling this space with a cofactor to replace the missing part of the substrate has the purpose of most closely mimicking the MDP molecule. As the cofactor is not modified during the reaction, it will therefore be added only in catalytic amounts. By chance, it may happen that the complementary cofactor of a reaction has a positive effect on the reaction of another substrate. Generally, the cofactor can be any molecule comprising a phosphoanhydride, and therefore having the general global formula R—$PO_2H$—O—$PO_3H_2$, in which R is in particular H, a linear, branched or cyclic alkyl group, preferably having from 1 to 10 or from 1 to 5 carbon atoms, or any other monovalent organic group. The analogous motifs corresponding to methylene diphosphonate monoesters, having the general formula R—O—$PO_2H$—$CH_2$—$PO_3H_2$ in which phosphyanhydride is replaced by a methylene bridge having the advantage of not being hydrolyzed, are also part of the invention. More generally, the cofactors can be monophosphate, or even phosphate-free, analogs of the previous molecules, or else any other molecule that can improve the reaction yield by providing steric or electronic complementation in the enzyme catalytic site. The cofactor is advantageously selected between pyrophosphate ion and methyl diphosphate.

In a preferred embodiment, the conversion occurs in the presence of a co-substrate, said co-substrate preferably being a compound containing a phosphoanhydride, and preferably being ATP, an rNTP, a dNTP or a mixture of several of these molecules, a polyphosphate, or pyrophosphate. The co-substrate is generally present in the host. However, in another particular embodiment, a co-substrate can be added to the reaction, preferably selected from the group consisting of ATP, an rNTP, a dNTP, a mixture of several rNTPs or dNTPs, a polyphosphate, and preferably pyrophosphate, or a compound containing a phosphoanhydride (represented by the general formula X—$PO_3H_2$).

Although the decarboxylation step, i.e. the reaction defined as (ii) herein-above, does not require ATP consumption, it could be shown that the presence of ATP in the reaction could be beneficial. It is assumed that ATP might have an effect on the folding of the protein by the binding of ATP to the ATP-binding site of the diphosphomevalonate decarboxylase. In fact, this can be observed by eye: the purified enzyme has a tendency to precipitate, and the addition of ATP prevents this effect. It is considered that not only ATP but also other similar compounds like dATP, ADP, AMP or other NTPs or dNTPs have this effect. Thus, in a preferred embodiment, the method according to the present invention is carried with ATP, dATP, ADP, AMP or an NTP other than ATP or a dNTP as co-substrate.

In another preferred embodiment the method according to the invention is carried out in culture, in the presence of an organism, preferably a microorganism, producing the enzymes. Thus, in such an embodiment of the invention, an organism, preferably a microorganism, that produces the respective enzyme(s) is used. In a preferred embodiment, the (micro)organism is recombinant in that the enzyme(s) produced by the host are heterologous relative to the production host. The method can thus be carried out directly in the culture medium, without the need to separate or purify the enzymes. In an especially advantageous manner, a (micro)organism is used having the natural or artificial property of endogenously producing one or more 3-hydroxyalk-4-enoates and/or a 3-phosphonoxyalk-4-enoate, and also expressing or overexpressing the enzyme(s) as specified above, natural or modified, so as to produce 1,3-diene compounds directly from a carbon source present in solution.

For example, the method according to the invention can be carried out by using microorganisms which produce one or more 3-hydroxyalk-4-enoates. It has been, e.g., been described in Ulmer et al. (Macromolecules 27 (1994), 1675-1679) that *Rhodospirillum rubrum* is capable of producing polymers consisting of 3-hydroxypent-4-enoate when grown on 4-pentenoic acid or on an equimolar mixture of 4-pentenoic acid and pentanoic acid.

Moreover, it has been reported by Rodrigues et al. (Appl. Micobiol. Biotechnol. 43 (1995), 880-886 and Appl. Microbiol. Biotechnol. 53 (2000), 453-460) that certain strains of *Burkholderia* sp. show the capacity of accumulating 3-hydroxypent-4-enoic acid when supplied with glucose or gluconate as the sole carbon and energy source. Thus, in one embodiment of the production of 1,3-butadiene according to the present invention it is preferred to use a microorganism which is capable of producing 3-hydroxy-pentenoic acid, such as *Rhodospirillum rubrum* or *Burkholderia* sp. and which has been genetically engineered such that they overexpress the decarboxylase enzyme(s), said enzyme(s) preferably originating from an organism different from the host microorganism. The genetic modification can consist, e.g. in integrating the corresponding gene(s) encoding the enzyme(s) into the chromosome, expressing the enzyme(s) from a plasmid containing a promoter upstream of the enzyme-coding sequence, the promoter and coding sequence preferably originating from different organisms, or any other method known to one of skill in the art. Alternatively, other bacteria or yeasts may have specific advantages and can be chosen. For instance, a yeast such as *Saccharomyces cerevisiae*, an extremophilic bacterium such as *Thermus thermophilus*, or anaerobic bacteria from the family Clostridiae, microalgae, or photosynthetic bacteria can be used.

It is also conceivable to isolate the genes encoding the proteins which are responsible for the synthesis of 3-hydroxypent-4-enoic acid from, e.g., *Rhodospirillum rubrum* or *Burkholderia* sp. and to introduce these genes into another organisms, in particular a microorganism, such as e.g. *E. coli* or *Saccharomyces*, an extremophilic bacterium such as *Thermus thermophilus*, or anaerobic bacteria from the family Clostridiae, microalgae, or photosynthetic bacteria.

The organisms used in the invention can be prokaryotes or eukaryotes, preferably, they are microorganisms such as bacteria, yeasts, fungi or molds, or plant cells or animal cells. In a particular embodiment, the microorganisms are bacteria, preferably of the genus *Escherichia*, even more preferably of the species *Escherichia coli*.

In another preferred embodiment, the microorganisms are recombinant bacteria of the genus *Escherichia*, preferably of the species *Escherichia coli*, having been modified so as to endogenously produce one or more 3-hydroxyalk-4-enoates, and converting them to 1,3-diene compounds.

In a further preferred embodiment the microorganism is a fungus, more preferably a fungus of the genus *Saccharomyces, Schizosaccharomyces, Aspergillus* or *Trichoderma* and even more preferably of the species *Saccharomyces cerevisiae, Schizosaccharomyces pombe, Aspergillus niger* or of the species *Trichoderma reesei*. In a particularly preferred embodiment the microorganism is a recombinant yeast producing 3-hydroxyalk-4-enoates and converting them to 1,3-diene compounds due to the expression of the enzymes specified above.

In another preferred embodiment, the method according to the invention makes use of a photosynthetic microorganism expressing the enzymes as specified above. Preferably, the microorganism is a photosynthetic bacterium, or a microalgae. Even more preferably such a microorganism has the natural or artificial property of endogenously producing one or more 3-hydroxyalk-4-enoates. In this case the microorganism would be capable of producing 1,3-diene compounds directly from $CO_2$ present in solution.

It is also conceivable to use in the method according to the invention one microorganism that produces an enzyme as defined in (i) above and another microorganism which produces an enzyme as defined in (ii) above. Moreover, in a further embodiment at least one of the microorganisms is capable of producing one or more 3-hydroxyalk-4-enoates or, in an alternative embodiment, a further microorganism is used in the method which is capable of producing one or more 3-hydroxyalk-4-enoates.

In another preferred embodiment the method according to the invention makes use of a multicellular organism expressing the enzymes as defined above. Examples for such organisms are plants or animals.

In a particular embodiment, the method involves culturing microorganisms in standard culture conditions (30-37° C. at 1 atm, in a fermenter allowing aerobic growth of the bacteria) or non-standard conditions (higher temperature to correspond to the culture conditions of thermophilic organisms, for example).

In a further preferred embodiment the method of the invention is carried out in microaerophilic conditions. This means that the quantity of injected air is limiting so as to minimize residual oxygen concentrations in the gaseous effluents containing the 1,3-diene compound.

In another preferred embodiment the method according to the invention furthermore comprises the step of collecting gaseous 1,3-diene compounds degassing out of the reaction, i.e. recovering the products which degas, e.g., out of the culture. Thus in a preferred embodiment, the method is carried out in the presence of a system for collecting the 1,3-diene compound under gaseous form during the reaction.

As a matter of fact, short 1,3-diene compounds, and particularly butadiene, adopt the gaseous state at room temperature and atmospheric pressure. The method according to the invention therefore does not require extraction of the product from the liquid culture medium, a step which is always very costly when performed at industrial scale. The evacuation and storage of the gaseous hydrocarbons and their possible subsequent physical separation and chemical conversion can be performed according to any method known to one of skill in the art.

In a particular embodiment, the method also comprises detecting the 1,3-diene compound (for example butadiene or isoprene) which is present in the gaseous phase. The presence of the compound to be produced in an environment of air or another gas, even in small amounts, can be detected by using various techniques and in particular by using gas chromatography systems with infrared or flame ionization detection, or by coupling with mass spectrometry.

The present invention also relates to a method for producing a 1,3-diene compound comprising the step of enzymatically converting a 3-phosphonoxyalk-4-enoate into the corresponding 1,3-diene compound by use of an enzyme which can catalyze the conversion via decarboxylation and dephosphorylation.

As regards the preferred enzyme to be used in such a method, the same applies as has been set forth above in connection with (ii) of the method according to the invention as described herein-above.

Moreover, also with respect to the other preferred embodiments described above for the method according to the invention, the same applies to the method for producing a 1,3-diene compound from a 3-phosphonoxyalk-4-enoate.

Thus, the present invention in particular also relates to a method for the production of a 1,3-diene compound characterized in that it comprises the step of converting a 3-phosphonoxyalk-4-enoate with an enzyme having the activity of a terpene synthase into a 1,3-diene compound.

As mentioned above, the inventors have surprisingly found that a terpene synthase is able to catalyze the conversion of a 3-phosphonoxyalk-4-enoate into a 1,3-diene compound (see Example 11 and FIG. 8). The terms "3-phosphonoxyalk-4-enoate" and "1,3-diene" have the same meaning as described herein above and the same applies here as has been described above in connection with preferred embodiments. Thus, in one preferred embodiment the 3-phosphonoxyalk-4-enoate is 3-phosphonoxypent-4-enoate and the produced 1,3-diene is 1,3-butadiene. In another preferred embodiment, the 3-phosphonoxyalk-4-enoate is 3-phosphonoxy-4-methylpent-4-enoate or 3-phosphonoxy-3-methylpent-4-enoate and the 1,3-diene is isoprene.

As regards the terpene synthase to be employed in such a method and the corresponding preferred embodiments, the same applies as has been described herein above.

The present invention also relates to the use of organisms, preferably microorganisms, which produce the above described enzymes, preferably at least two enzymes, wherein one enzyme is selected from (i) as specified above and the other enzyme is selected from (ii) as specified above, for the production of a 1,3-diene compound from a 3-hydroxyalk-4-enoate. In a preferred embodiment such an organism is a recombinant organism in the sense that it is genetically modified due to the introduction of at least one nucleic acid molecule encoding at least one of the above mentioned enzymes. Preferably such a nucleic acid molecule is heterologous with regard to the organism which means that it does not naturally occur in said organism.

In a preferred embodiment such an organism is an organism which produces one or more 3-hydroxyalk-4-enoates. Rhodospirillum rubrum is, for example, capable of producing polymers consisting of 3-hydroxypent-4-enoate when grown on 4-pentenoic acid or on an equimolar mixture of 4-pentenoic acid and pentanoic acid. Moreover, certain strains of Burkholderia sp. show the capacity of accumulating 3-hydroxypent-4-enoic acid when supplied with glucose or gluconate as the sole carbon and energy source.

Thus, in one embodiment a microorganism is used which is capable of producing 3-hydroxy-pentenoic acid, such as Rhodospirillum rubrum or Burkholderia sp. and which has been genetically engineered such that it overexpresses the decarboxylase enzyme(s), said enzyme(s) preferably originating from an organism different from the host microorganism. It is also conceivable to isolate the genes encoding the proteins which are responsible for the synthesis of 3-hydroxypent-4-enoic acid from, e.g., Rhodospirillum rubrum or Burkholderia sp. and to introduce these genes into another organisms, in particular a microorganism, such as e.g. E. coli or Saccharomyces, an extremophilic bacterium such as Thermus thermophilus, or anaerobic bacteria from the family Clostridiae, microalgae, or photosynthetic bacteria.

Thus, the present invention also relates to the use of such an organism, preferably a microorganism, which comprises a nucleic acid molecule coding for an enzyme as defined in (i) above and which comprises a nucleic acid molecule coding for an enzyme as defined in (ii) above, for the production of a 1,3-diene compound from a 3-hydroxyalk-4-enoate. In a preferred embodiment at least one of the nucleic acid molecules is heterologous to the organism which means that it does not naturally occur in said organism. The microorganism is preferably a bacterium, a yeast or a fungus. In another preferred embodiment the organism is a plant or non-human animal. In a further preferred embodiment, the organism is an organism which produces one or more 3-hydroxyalk-4-enoates. As regards other preferred embodiments, the same applies as has been set forth above in connection with the method according to the invention.

Moreover, the present invention also relates to a composition comprising a microorganism as defined herein above, a suitable culture medium and a 3-hydroxyalk-4-enoate compound or a carbon source that can be converted by the microorganism to a 3-hydroxyalk-4-enoate compound.

The present invention also relates to the use of an enzyme having decarboxylase activity as described herein-above or of a combination of at least two enzymes, wherein one enzyme is selected from the following (i) and the other enzyme is selected from the following (ii) or of an organism, preferably a microorganism, as described herein-above or of a composition according to the invention, for producing a 1,3-diene compound from a 3-phosphonoxyalk-4-enoate, wherein (i) and (ii) are as follows:

(i) a first enzyme having an activity of converting the 3-hydroxyalk-4-enoate into the corresponding 3-phosphonoxyalk-4-enoate; and (ii) a second enzyme being different from the first enzyme and having an activity of converting said 3-phosphonoxyalk-4-enoate into said 1,3-diene compound by a decarboxylation reaction.

As regards the preferred embodiments of the different components recited, the same applies as has been set forth above in connection with the method according to the invention.

The present invention also relates to the use of a terpene synthase for producing a 1,3-diene compound from a 3-phosponoxyalk-4-enoate by the dephosphorylation-decarboxylation of the 3-phosphonoxyalk-4-enoate.

Other aspects and advantages of the invention will be described in the following examples, which are given for purposes of illustration and not by way of limitation.

EXAMPLES

Example 1

Cloning, Expression and Purification of Enzymes

Cloning, Bacterial Cultures and Expression of Proteins.

The genes encoding studied enzymes were cloned in the pET 25b or pET 22b vectors (Novagen). A stretch of 6 histidine codons was inserted after the methionine initiation codon to provide an affinity tag for purification. Competent *E. coli* BL21(DE3) cells (Novagen) were transformed with these vectors according to the heat shock procedure. The transformed cells were grown with shaking (160 rpm) on ZYM-5052 auto-induction medium (Studier F W, *Prot. Exp. Pur.* 41, (2005), 207-234) for 6 hours at 37° C. and protein expression was continued at 28° C. overnight (approximately 16 hours). The cells were collected by centrifugation at 4° C., 10,000 rpm for 20 min and the pellets were frozen at −80° C.

Protein Purification and Concentration.

The pellets from 200 ml of culture cells were thawed on ice and resuspended in 5 ml of $Na_2HPO_4$ pH 8 containing 300 mM NaCl, 5 mM $MgCl_2$ and 1 mM DTT. Twenty microliters of lysonase (Novagen) were added. Cells were incubated 10 minutes at room temperature and then returned to ice for 20 minutes. Cell lysis was completed by sonication for 3×15 seconds. The bacterial extracts were then clarified by centrifugation at 4° C., 10,000 rpm for 20 min. The clarified bacterial lysates were loaded on PROTINO-1000 Ni-TED column (Macherey-Nagel) allowing adsorption of 6-His tagged proteins. Columns were washed and the enzymes of interest were eluted with 4 ml of 50 mM $Na_2HPO_4$ pH 8 containing 300 mM NaCl, 5 mM $MgCl_2$, 1 mM DTT, 250 mM imidazole. Eluates were then concentrated and desalted on Amicon Ultra-4 10 kDa filter unit (Millipore) and resuspended in 0.25 ml 50 mM Tris-HCl pH 7.5 containing 0.5 mM DTT and 5 mM $MgCl_2$. Protein concentrations were quantified by direct UV 280 nm measurement on the NanoDrop 1000 spectrophotometer (Thermo Scientific). The purity of proteins varied from 70% to 90%.

Example 2

Characterization of the 3-hydroxypent-4-enoate Phosphorylation Activity

Figure 1:
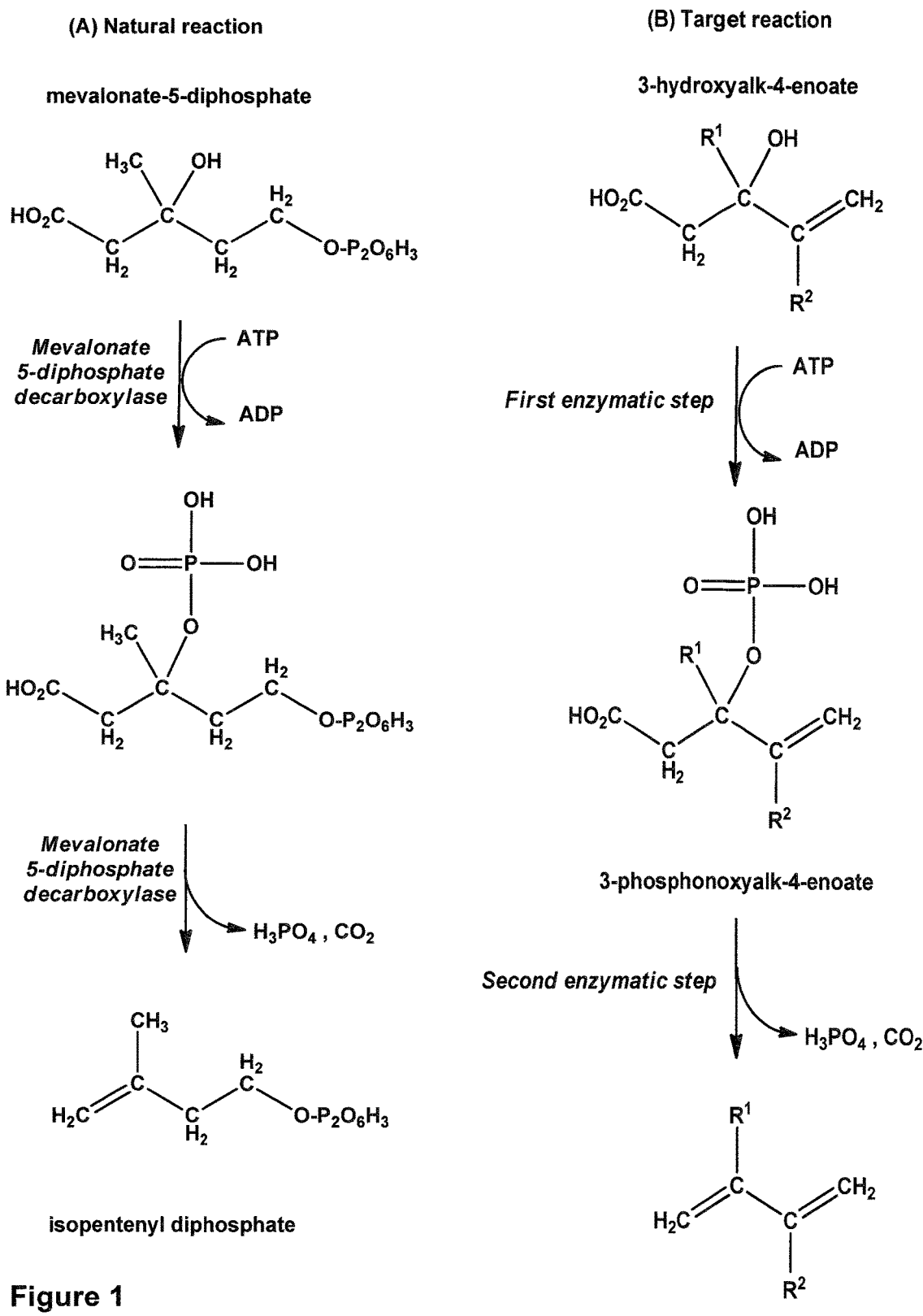
FIG. 1 shows the reaction catalyzed by a diphosphomevalonate decarboxylase using diphosphomevalonate (A) or using a 3-hydroxyalk-4-enoate (B) as a substrate.
Figure 2:
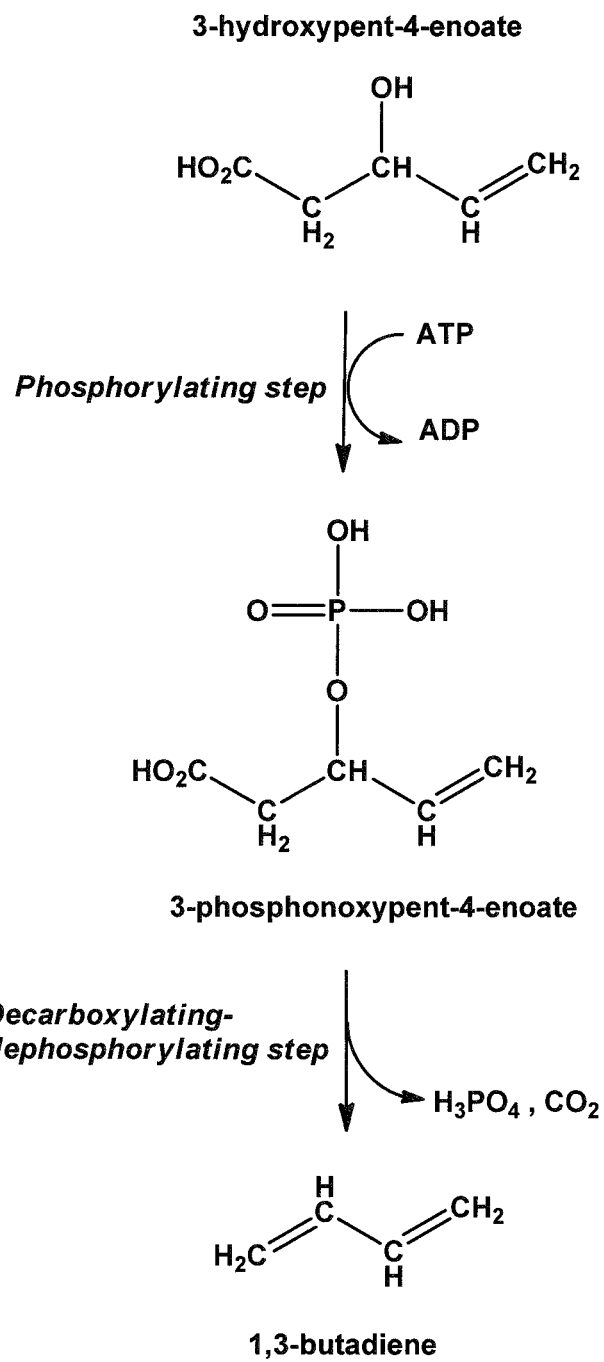
FIG. 2 shows the reaction catalyzed by a diphosphomevalonate decarboxylase using 3-hydroxypent-4-enoate as a substrate leading to the production of 1,3-butadiene.
Figure 3:
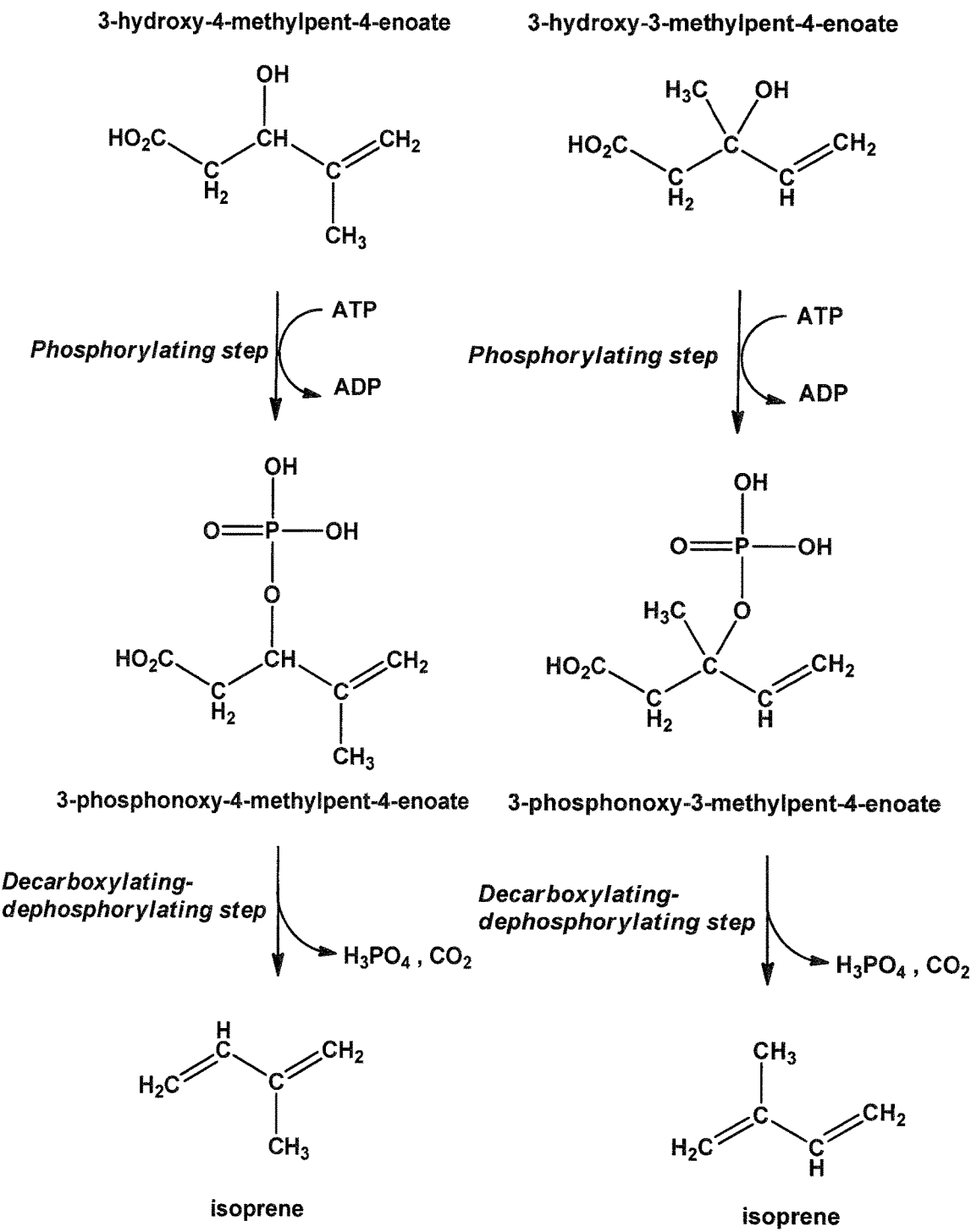
FIG. 3 shows the reaction catalyzed by a diphosphomevalonate decarboxylase using 3-hydroxy-4-methylpent-4-enoate or 3-hydroxy-3 methylpent-4-enoate as a substrate leading to the production of isoprene.
Figure 4:
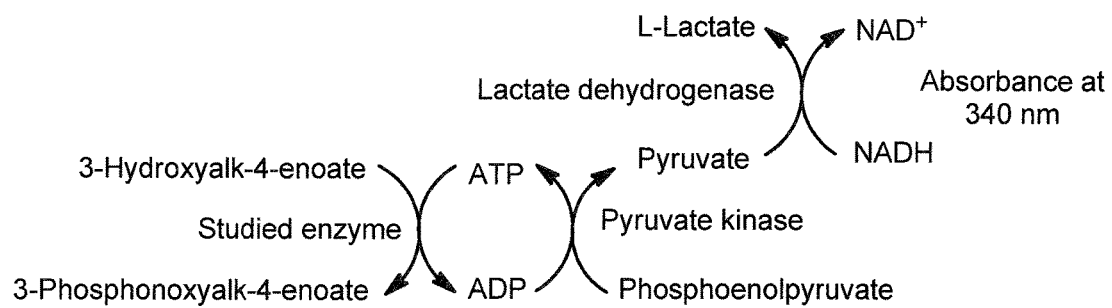
FIG. 4 shows a scheme of the ADP quantification assay, monitoring NADH consumption by the decrease of absorbance at 340 nm.

The release of ADP that is associated with 1,3-butadiene production from 3-hydroxypent-4-enoate, was quantified using the pyruvate kinase/lactate dehydrogenase coupled assay (FIG. 4). The purified mevalonate diphosphate decarboxylases from *Th. acidophilum, Th. volcanium* and *S. mitis* were evaluated for their ability to phosphorylate 3-hydroxypent-4-enoate releasing ADP.

The studied enzymatic reaction was carried out under the following conditions at 37° C.:
50 mM Tris-HCl pH 7.5
10 mM $MgCl_2$
100 mM KCl
5 mM ATP
0.4 mM NADH
1 mM Phosphoenolpyruvate
3 U/ml Lactate dehydrogenase
1.5 U/ml Pyruvate kinase
50 mM 3-Hydroxypent-4-enoate
The pH was adjusted to 7.5

Each assay was started by the addition of a particular enzyme (at a concentration from 0.05 to 1 mg/ml) and the disappearance of NADH was monitored by following the absorbance at 340 nm. Assays with mevalonate diphosphate (MDP) decarboxylases gave rise to a reproducible increase in ADP production in the presence of 3-hydroxypent-4-enoate. The enzymes from the *Thermoplasma phylum* displayed higher phosphotransferase activity than decarboxylase from *S. mitis* (Table 3).

TABLE 3

| Mevalonate diphosphate decarboxylase | Activity, nmol/min/mg protein |
|---|---|
| *Th. acidophilum* (mutant L200E) | 138 |
| *Th. volcanium* | 114 |
| *S. mitis* | 0.52 |

Mass spectrometry was then applied to confirm the formation of 3-phosphonoxypent-4-enoate in the assay with mutant L200E of MDP decarboxylase from *Th. acidophilum*.

Example 3

Mass Spectrometry Analysis of the Phosphorylation Reaction

The desired enzymatic reactions were carried out under the following conditions:
50 mM Tris-HCl pH 7.5
10 mM $MgCl_2$
10mM KCl
20 mM 3-hydroxypent-4-enoate
20 mM ATP
0.2 mg/ml purified MDP decarboxylase from *Th. acidophilum* (mutant L200E).

Figure 5:
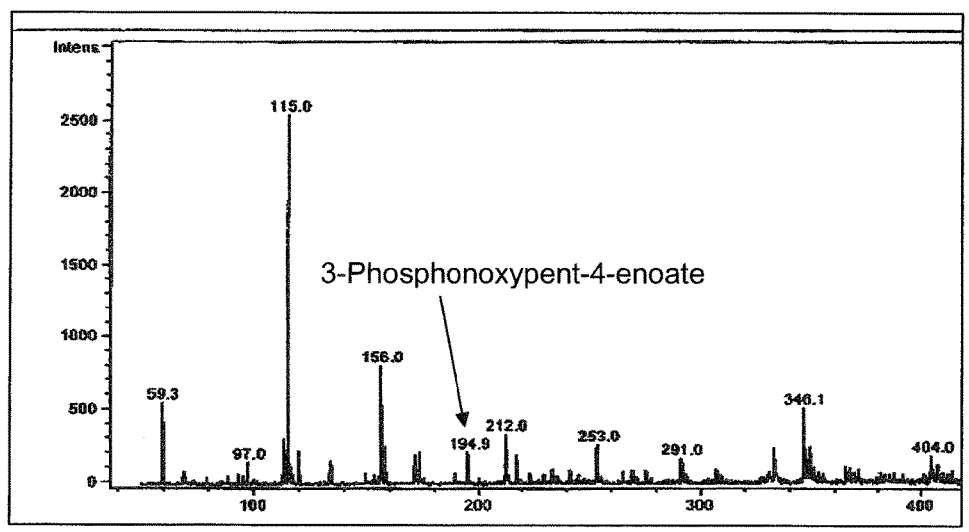
FIG. 5 shows a mass spectrum of the enzymatic assay for 3-hydroxypent-4-enoate phosphorylation.
Figure 6:
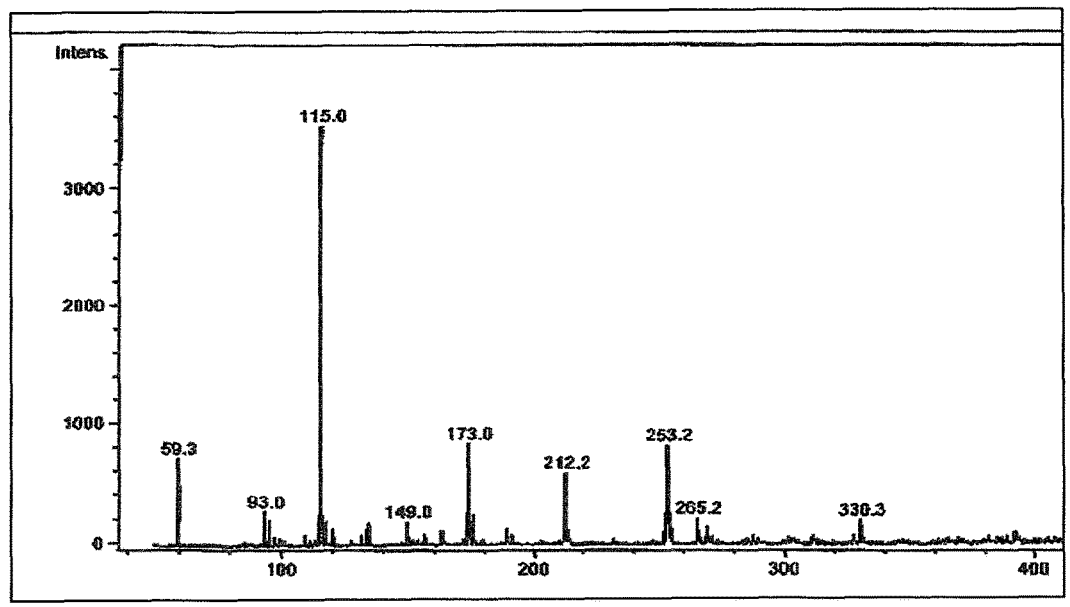
FIG. 6 shows a mass spectrum of the enzyme-free control assay for 3-hydroxypent-4-enoate phosphorylation.

The control reactions without enzyme, without substrate and without ATP were run in parallel. The assays were incubated overnight without shaking at 37° C. Typically, an aliquot of 200 µl reaction was removed, centrifuged and the supernatant was transferred into a clean vial. The MS spectra were obtained on Esquire 3000 (Bruker) Ion Trap Mass Spectrometer with Electrospray Ionization Interface in negative ion mode. The presence of 3-phosphonoxypent-4-enoate was evaluated. MS analysis showed an [M-H]⁻ ion at m/z 194.9 corresponding to 3-phosphonoxypent-4-enoate from the sample containing the enzyme but not from the negative controls (FIGS. 5, 6).

Example 4

Kinetic Parameters of Reaction of 3-hydroxypent-4-enoate Phosphorylation

Kinetic parameters were determined by varying substrate concentration between 0 and 30 mM under assay conditions, described in example 2.

Figure 7:
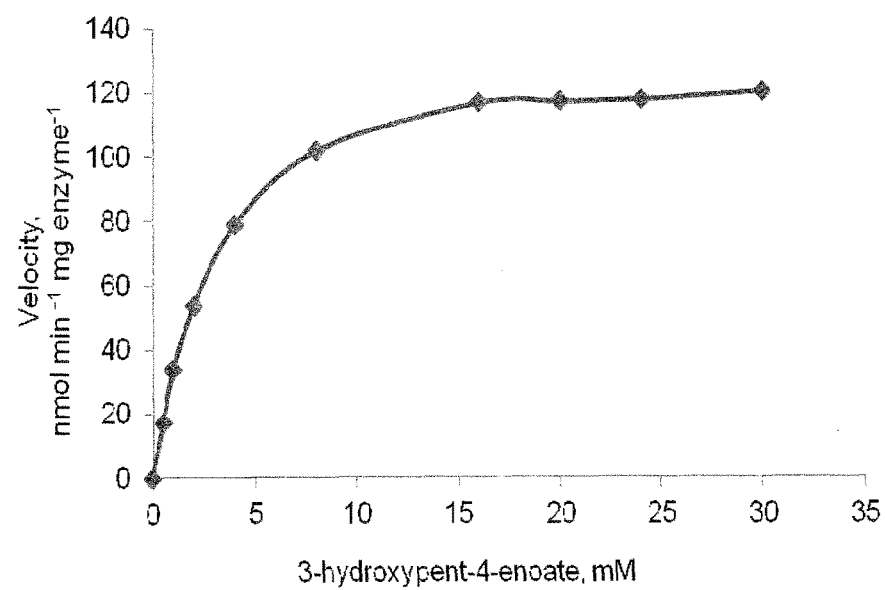
FIG. 7 shows the plot of the velocity as a function of substrate concentration for the phosphotransferase reaction catalyzed by the mutant L200E of MDP decarboxylase from Th. acidophilum. Initial rates were computed from the kinetics over the 30 first minutes of the reaction.

FIG. 7 shows an example of a Michaelis-Menten plot corresponding to the data collected for the mutant L200E of MDP decarboxylase from *Th. acidophilum*. This enzyme was found to have a $K_M$ of 3.7 mM and a $k_{cat}$ of 0.09 sec$^{-1}$.

Example 5

Butadiene production from 3-hydroxypent-4-enoate

The desired enzymatic reaction was carried out under the following conditions:
50 mM Tris HCl pH 7.5
10 mM MgCl$_2$
20 mM KCl
50 mM ATP
200 mM 3-hydroxypent-4-enoate
The pH was adjusted to 7.5

Each assay was started by the addition of a particular enzyme to 0.5 ml of reaction mixture. The assays were then incubated with shaking at 37° C. in a 2 ml sealed vial (Interchim). Control reactions were run in parallel. After 48 hours of incubation the reaction mixtures were analyzed as follows. To 0.5 mL of each sample, 0.125 ml of heptane were added and the sample was incubated at 25° C. for 1 hour with shaking. The upper heptane phase was analyzed by gas chromatography (GC) on a Varian 430-GC chromatograph equipped with a FID detector. A 1 μL sample was separated on the GC using an Rt-Alumina BOND/Na$_2$SO$_4$ column (Restek) and nitrogen carrier gas. The oven cycle for each sample was 130° C. for 10 minutes, increasing temperature at 20° C./minute to a temperature of 200° C., and a hold at 200° C. for 10 minutes. The total run time was 23.5 minutes The enzymatic reaction product was identified by comparison with commercial 1,3-butadiene (Sigma). The results of butadiene production are presented in Table 4.

TABLE 4

| Assay | 1,3-Butadiene peak area, arbitrary units |
| --- | --- |
| Without substrate | 0 |
| Without enzyme | 0.8 |
| With 11 mg/ml of purified S. mitis MDP decarboxylase | 1.0 |
| Combining assay with 1 mg/ml Th. acidophilum enzyme (mutant L200E) and 10 mg/ml S. mitis enzyme | 1.6 |

The formation of 1,3-butadiene observed in the assay without enzyme is probably due to the spontaneous decomposition of 3-hydroxypent-4-enoate. The addition of MDP decarboxylase from *S. mitis* led to a 1.25-fold increase of butadiene production after 48 h of incubation. The highest production of isobutene was observed in the assay combining the MDP decarboxylase from *Th. acidophilum* and the MDP decarboxylase from *S. mitis*. This indicated that the two enzymes present in the assay were performing complementarily the two steps of reaction producing butadiene from 3-hydroxypent-4-enoate: transfer of the terminal phosphoryl group from ATP to the C3-oxygen of 3-hydroxypent-4-enoate followed by combined dephosphorylation-decarboxylation of the intermediate 3-phosphonoxypent-4-enoate.

Example 6

Butadiene Production from 3-phosphonoxypent-4-enoate 3-phosphonoxypent-4-enoate is synthesized by company specialized in custom synthesis, Syntheval (France).

The studied enzymatic reactions are carried out under the following conditions at 37° C.:
50 mM Tris-HCl pH 7.5
10 mM MgCl$_2$
0-20 mM KCl
5 mM ATP
0-250 mM 3-phosphonoxypent-4-enoate
The pH is adjusted to 7.5

The reaction is initiated by the addition of a particular enzyme to 0.5 ml of reaction mixture. The free-enzyme control reactions are carried out in parallel. The assays are incubated with shaking at 37° C. in a 2 ml sealed vial (Interchim). The production of butadiene is measured by analyzing aliquots sampled over a 72 hour incubation period. Volatile compounds in the headspace of reaction mixture are collected and directly injected into a Varian 430-GC chromatograph equipped with a flame ionization detector and an Rt-Alumina BOND/Na$_2$SO$_4$ column (Restek). Additionally, 1,3-butadiene production is monitored by analysis of reaction mixture using gas chromatography as described in example 5. Commercial 1,3-butadiene is used as reference.

Example 7

Characterization of the 3-hydroxy-3-methylpent-4-enoate Activity

The release of ADP associated with isoprene production from 3-hydroxy-3-methylpent-4-enoate is quantified using the pyruvate kinase/lactate dehydrogenase coupled assay (FIG. 4). The purified mevalonate diphosphate decarboxylases are evaluated for their ability to phosphorylate this substrate releasing ADP.

The studied enzymatic reactions are carried out under the following conditions at 37° C.:
50 mM Tris-HCl pH 7.5
10 mM MgCl$_2$
100 mM KCl
5 mM ATP
0.4 mM NADH
1 mM Phosphoenolpyruvate
3 U/ml Lactate dehydrogenase
1.5 U/ml Pyruvate kinase
50 mM 3-Hydroxy-3-methylpent-4-enoate Each assay is started by the addition of a particular enzyme (at a concentration from 0.05 to 1 mg/ml) and the disappearance of NADH is monitored by following the absorbance at 340 nm.

Example 8

Characterization of the 3-hydroxy-4-methylpent-4-enoate Phosphorylation Activity The release of ADP associated with isoprene production from 3-hydroxy-4-methylpent-4-enoate is quantified using the pyruvate kinase/lactate dehydrogenase coupled assay (FIG. 4). The purified mevalonate diphosphate decarboxylases are evaluated for their ability to phosphorylate this substrate releasing ADP.

The studied enzymatic reactions are carried out under the following conditions at 37° C.:
50 mM Tris-HCl pH 7,5
10 mM MgCl$_2$
100 mM KCl 5 mM ATP
0.4 mM NADH
1 mM Phosphoenolpyruvate
3 U/ml Lactate dehydrogenase
1.5 U/ml Pyruvate kinase
50 mM 3-Hydroxy-4-methylpent-4-enoate Each assay is started by the addition of a particular enzyme (at a concentration from 0.05 to 1 mg/ml) and the disappearance of NADH is monitored by following the absorbance at 340 nm.

Example 9

Isoprene Production from 3-hydroxy-3-methylpent-4-enoate

The studied enzymatic reactions are carried out under the following conditions at 37° C.:
50 mM Tris-HCl pH 7.5
10 mM MgCl$_2$
20 mM KCl
5 mM ATP
0-200 mM 3-hydroxy-3-methylpent-4-enoate
The pH is adjusted to 7.5

The reaction is initiated by the addition of one or two particular enzyme(s) to 0.5 ml of reaction mixture. The enzyme-free control reactions are carried out in parallel. The assays are incubated with shaking at 37° C. in a 2 ml sealed vial (Interchim). The gas present in the headspace is collected and analyzed by gas chromatography coupled with a flame ionization detector. The enzymatic reaction product is identified by comparison with commercial isoprene (Sigma).

Example 10

Isoprene Production from 3-hydroxy-4-methylpent-4-enoate

The studied enzymatic reactions are carried out under the following conditions at 37° C.:
50 mM Tris-HCl pH 7.5
10 mM MgCl$_2$
20 mM KCl
5 mM ATP
0-200 mM 3-hydroxy-4-methylpent-4-enoate
The pH is adjusted to 7.5

The reaction is initiated by the addition of one or two particular enzymes to 0.5 ml of reaction mixture. The enzyme-free control reactions are carried out in parallel. The assays are incubated with shaking at 37° C. in a 2 ml sealed vial (Interchim). The gas present in the headspace is collected and analyzed by gas chromatography coupled with a flame ionization detector. The enzymatic reaction product is identified by comparison with commercial isoprene (Sigma).

Example 11

1,3-butadiene Production from 3-phosphonoxypent-4-enoate by Using a Terpene Synthase The sequence of the isoprene synthase inferred from the genome from *Pueraria montana* var. *lobata* (Uniprot Q6EJ97) was generated by oligonucleotide concatenation to fit the codon usage of *E. coli*. The amino acid sequence of the enzyme is shown in SEQ ID NO: 30. A stretch of 6 histidine codons was inserted after the methionine initiation codon to provide an affinity tag for purification. The gene thus synthesized was cloned in a pET 25b(+) expression vector (the vector was constructed by GeneArt AG). The corresponding enzyme was expressed in *E. coli* and purified as described in Example 1.

The reactions were performed in sealed vials. The total volume was 0.5 ml. Final concentrations were 5 mg/ml enzyme, 50 mM 3-phosphonoxypent-4-enoate, 4 mM DTT, 50 mM MgCl$_2$, 50 mM KCl, 50 mM Tris-HCl buffer pH 7.5. The incubation was carried out at 37° C. for 24 h. The control reactions without enzyme or without substrate were performed in parallel under the same conditions.

One ml of the gaseous phase of the reaction was collected and analyzed by Gas-Chromatography with Flame Ionization Detector (GC-FID) ((Brucker GC 450) using a RTX-alumina column (Varian), with an isocratic elution at 130° C. and nitrogen as carrier gas at flow rate of 1.5 ml/min. The retention of commercial 1,3-butadiene (Sigma) in these conditions was 7.4 min.

Figure 8:
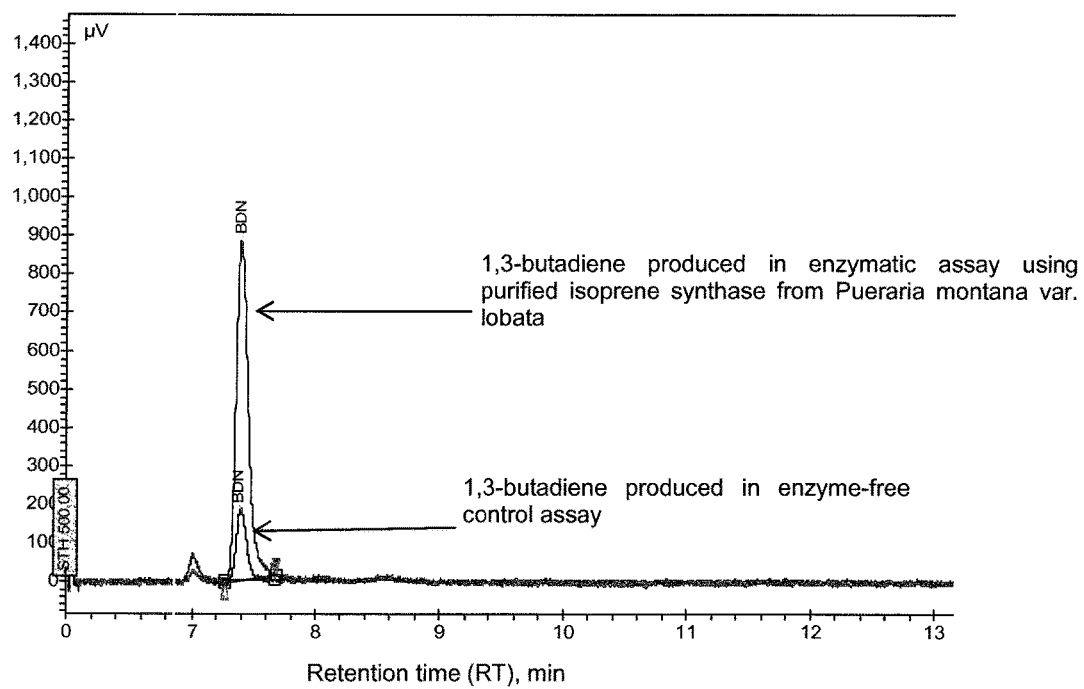
FIG. 8 shows the production of 1,3-butadiene from 3-phosphonoxypent-4-enoate in the absence and presence of isoprene synthase from *Pueraria montana* var. *lobata*.

Results: No formation of 1,3-butadiene was observed without substrate. The GC analysis of reactions without enzyme and with non-relevant enzyme showed only traces of butadiene resulted from the thermal decomposition of the 3-phosphonoxypent-4-enoate. The catalytic tests showed a significant increase of butadiene production in the presence of purified isoprene synthase from *Pueraria montana* var. *lobata*. The ratio of butadiene produced after 24 hours incubation in the presence of isoprene synthase versus butadiene produced in the absence of enzyme is about 5 fold judging from butadiene peak areas (FIG. 8). These results clearly indicate that a terpene synthase such as isoprene synthase catalyzes the conversion of a 3-phosphonoxyalk-4-enoate to a 1,3-diene, in particular 3-phosphonoxypent-4-enoate to 1,3-butadiene.

The invention claimed is:

1. A method for the production of a 1,3-diene compound that comprises converting a 3-hydroxyalk-4-enoate with a diphosphomevalonate decarboxylase (EC 4.1.1.33) into a 1,3-diene compound, wherein the 3-hydroxyalk-4-enoate has the general formula of $C_{n+1}H_{2n}O_3$ with $3<n<7$ and comprises a 3-hydroxypent-4-enoate as a common motif and optionally a methyl substitution on carbon 3 and carbon 4.

2. The method of claim 1 wherein the 3-hydroxyalk-4-enoate is 3-hydroxypent-4-enoate and the produced 1,3-diene compound is 1,3-butadiene.

3. The method of claim 1 wherein the 3-hydroxyalk-4-enoate is 3-hydroxy-4-methylpent-4-enoate or 3-hydroxy-3-methylpent-4-enoate and the produced 1,3-diene compound is isoprene.

4. The method of claim 1 wherein the diphosphomevalonate decarboxylase comprises the amino acid sequence of SEQ ID NOs: 1 to 19 or 22 to 29.

5. The method of claim 4 wherein the diphosphomevalonate decarboxylase comprises the amino acid sequence of SEQ ID NO: 6, 16, 17, 18 or 19.

6. The method of claim 1, wherein
   (i) a first diphosphomevalonate decarboxylase converts the 3-hydroxyalk-4-enoate into the corresponding 3-phosphonoxyalk-4-enoate; and
   (ii) a second diphosphomevalonate decarboxylase being different from the first diphosphomevalonate decarboxylase which converts said 3-phosphonoxyalk-4-enoate into said 1,3-diene compound by a decarboxylation reaction.

7. The method of claim 6 wherein the first diphosphomevalonate decarboxylase is a protein comprising the amino acid sequence as shown in SEQ ID NO: 18.

8. The method of claim 6 wherein the second diphosphomevalonate decarboxylase is a protein comprising the amino acid sequence as shown in SEQ ID NO: 24.

9. A method for the production of a 1,3-diene compound comprising:
   (i) converting a 3-hydroxyalk-4-enoate into a 3-phosphonoxyalk-4-enoate by a disphosphomevalonate decarboxylase (EC 4.1.1.33); and
   (ii) converting 3-phosphonoxyalk-4-enoate into a 1,3-diene compound by a terpene synthase; wherein 3-hydroxyalk-4-enoate has the general formula of $C_{n+1}H_{2n}O_3$ with $3<n<7$ and comprises a 3-hydroxypent-4-enoate as common motif and optionally a methyl substitution on carbon 3 and carbon 4.

10. The method of claim 9, wherein said terpene synthase is an isoprene synthase (EC 4.2.3.27).

11. A method for producing a 1,3-diene compound comprising enzymatically converting a 3-phosphonoxyalk-4-enoate into the corresponding 1,3-diene compound by a terpene synthase; wherein 3-hydroxyalk-4-enoate has the general formula of $C_{n+1}H_{2n}O_3$ with $3<n<7$ and comprises a 3-hydroxypent-4-enoate as common motif and optionally a methyl substitution on carbon 3 and carbon 4.

12. The method of claim 11, wherein said terpene synthase is an isoprene synthase (EC 4.2.3.27).

13. The method of claim 11 wherein the 3-phosphonoxyalk-4-enoate is 3-phosphonoxypent-4-enoate and the produced 1,3-diene is 1,3-butadiene.

14. The method of claim 11 wherein the 3-phosphonoxyalk-4-enoate is 3-phosphonoxy-4-methylpent-4-enoate or 3-phosphonoxy-3-methylpent-4-enoate and the produced 1,3-diene is isoprene.

15. The method of claim 1 which is carried out in vitro.

16. The method of claim 1 wherein a co-substrate is added.

17. The method of claim 16 wherein the co-substrate is ATP, a rNTP, a dNTP, a polyphosphate or pyrophosphate, or a mixture of any of these compounds.

18. The method of claim 1 wherein the method is carried out by making use of a microorganism producing said enzyme or said enzymes.

19. The method of claim 18, wherein the microorganism is capable of producing a 3-hydroxyalk-4-enoate and/or a 3-phosphonoxyalk-4-enoate.

20. The method of claim 6 wherein the first diphosphomevalonate decarboxylase is:
   (A) a protein comprising the amino acid sequence as shown in SEQ ID NO: 16;

(B) a protein comprising the amino acid sequence as shown in SEQ ID NO: 17; or
(C) a protein comprising the amino acid sequence as shown in SEQ ID NO: 19.

21. The method of claim 6 wherein the second diphosphomevalonate decarboxylase is:
(A) a protein comprising the amino acid sequence as shown in SEQ ID NO: 12;
(B) a protein comprising the amino acid sequence as shown in SEQ ID NO: 22;
(C) a protein comprising the amino acid sequence as shown in SEQ ID NO: 23;
(D) a protein comprising the amino acid sequence as shown in SEQ ID NO: 1;
(E) a protein comprising the amino acid sequence as shown in SEQ ID NO: 7;
(F) a protein comprising the amino acid sequence as shown in SEQ ID NO: 25;
(G) a protein comprising the amino acid sequence as shown in SEQ ID NO: 26;
(H) a protein comprising the amino acid sequence as shown in SEQ ID NO: 27;
(I) a protein comprising the amino acid sequence as shown in SEQ ID NO: 28; or
(J) a protein comprising the amino acid sequence as shown in SEQ ID NO: 29.

22. The method of claim 9, wherein said terpene synthase is a monoterpene synthase, an alpha-farnesene synthases (EC 4.2.3.46), a beta-farnesene synthase (EC 4.2.3.47), a myrcene/(E)-beta-ocimene synthase (EC 4.2.3.15) or a pinene synthase (EC 4.2.3.14).

23. The method of claim 11, wherein said terpene synthase is a monoterpene synthase, an alpha-farnesene synthases (EC 4.2.3.46), a beta-farnesene synthase (EC 4.2.3.47), a myrcene/(E)-beta-ocimene synthase (EC 4.2.3.15) or a pinene synthase (EC 4.2.3.14).

24. The method of claim 9 wherein the diphosphomevalonate decarboxylase comprises the amino acid sequence of SEQ ID NOs: 1 to 19 or 22 to 29.

* * * * *